US006949371B2

United States Patent
Merkulov et al.

(10) Patent No.: US 6,949,371 B2
(45) Date of Patent: Sep. 27, 2005

(54) ISOLATED HUMAN DRUG-METABOLIZING PROTEINS, NUCLEIC ACID MOLECULES ENCODING HUMAN DRUG-METABOLIZING PROTEINS, AND USES THEREOF

(75) Inventors: Gennady V. Merkulov, Baltimore, MD (US); Chunhua Yan, Boyds, MD (US); Valentina Di Francesco, Rockville, MD (US); Ellen M. Beasley, Darnestown, MD (US)

(73) Assignee: Applera Corporation, Norwalk, CT (US)

( * ) Notice: Subject to any disclaimer, the term of this patent is extended or adjusted under 35 U.S.C. 154(b) by 90 days.

(21) Appl. No.: 10/338,691

(22) Filed: Jan. 9, 2003

(65) Prior Publication Data

US 2003/0104592 A1 Jun. 5, 2003

Related U.S. Application Data

(60) Division of application No. 09/852,067, filed on May 10, 2001, now Pat. No. 6,531,297, which is a continuation-in-part of application No. 09/818,647, filed on Mar. 28, 2001, now abandoned.
(60) Provisional application No. 60/241,745, filed on Oct. 20, 2000.

(51) Int. Cl.[7] ................................................. C12N 9/00
(52) U.S. Cl. ........................................ 435/183; 424/94.1
(58) Field of Search ........................ 435/183; 424/94.1

(56) References Cited

FOREIGN PATENT DOCUMENTS

| WO | WO 95 30766 A | 11/1995 |
|---|---|---|
| WO | WO 01 40466 A | 6/2001 |
| WO | WO 01 51638 A | 7/2001 |
| WO | WO 01 77137 A | 10/2001 |
| WO | WO 02 16388 A | 2/2002 |

OTHER PUBLICATIONS

Matsubara et al. "Complementary DNA Cloning and Inducible Expression During Pregnancy of the Messenger RNA for Rabbit Pulmonary Prostaglandin Omega Hydroxylase Cytochrome P–450–P–2." Journal of Biological Chemistry, vol. 262, No. 27, 1987, pp. 13366–13371, XP002241281.
NCI–CGAP. "oh04f03.s1 NCI_CGAP_KID3 Homo Sapiens cDNA Clone Image:1456829 3' Similar to SW:CP48_RAT P24464 Cytochrome P450 IVA8; mRNA Sequence." Database EMBL 'Online! Mar. 15, 1998. Database accession No. AA863360. XP002241282.
NCI–CGAP. "n181a02.s1 NCI_CGAP–Br2 Homo Sapiens cDNA Clone Image:1057034 3' mRNA Sequence." Database EMBL 'Online! Sep. 11, 1997. Database accession No. AA557324. XP002241283.
Database GENSEQ 'Online! Dec. 17, 2001. Database accession No. AAS40801. XP002241284.
International Search report dated May 23, 2003.

Primary Examiner—Dave T. Nguyen
Assistant Examiner—Celine Qian
(74) Attorney, Agent, or Firm—Celera Genomics; Lin Sun-Hoffman

(57) ABSTRACT

The present invention provides amino acid sequences of peptides that are encoded by genes within the human genome, the drug-metabolizing enzyme peptides of the present invention. The present invention specifically provides isolated peptide and nucleic acid molecules, methods of identifying orthologs and paralogs of the drug-metabolizing enzyme peptides, and methods of identifying modulators of the drug-metabolizing enzyme peptides.

4 Claims, 27 Drawing Sheets

```
   1  CCCGCCTGCC TCCTCTCCCC AGGCCTGAGC TGCCCCTCCC ACTGCCTTTC
  51  CTTCTTCCCG CGAGTCAGAA GCTTCGCGAG GGCCCAGAGA GGCGGTGGGG
 101  TGGGCGACCC TACGCCAGCT CCGGGCGGGA GAAAGCCCAC CCTCTCCCGC
 151  GCCCCAGGAA ACCGCCGGCG TTCGGCGCTG CGCAGAGCCA TGGAATTCTC
 201  CTGGCTGGAG ACGCGCTGGG CGCGGCCCTT TTACCTGGCG TTCGTGTTCT
 251  GCCTGGCCCT GGGGCTGCTG CAGGCCATTA AGCTGTACCT GCGGAGGCAG
 301  CGGCTGCTGC GGGACCTGCG CCCCTTCCCA GCGCCCCCCA CCCACTGGTT
 351  CCTTGGGCAC CAGAAGTTTA TTCAGGATGA TAACATGGAG AAGCTTGAGG
 401  AAATTATTGA AAAATACCCT CGTGCCTTCC CTTTCTGGAT TGGGCCCTTT
 451  CAGGCATTTT TCTGTATCTA TGACCCAGAC TATGCAAAGA CACTTCTGAG
 501  CAGAACAGAT CCCAAGTCCC GGTACCTGCA GAAATTCTCA CCTCCACTTC
 551  TTGGAAAAGG ACTAGCGGCT CTAGACGGAC CCAAGTGGTT CCAGCATCGT
 601  CGCCTACTAA CTCCTGGATT CCATTTTAAC ATCCTGAAAG CATACATTGA
 651  GGTGATGGCT CATTCTGTGA AAATGATGCT GGATAAGTGG GAGAAGATTT
 701  GCAGCACTCA GGACACAAGC GTGGAGGTCT ATGAGCACAT CAACTCGATG
 751  TCTCTGGATA TAATCATGAA ATGCGCTTTC AGCAAGGAGA CCAACTGCCA
 801  GACAAACAGC ACCCATGATC CTTATGCAAA AGCCATATTT GAACTCAGCA
 851  AAATCATATT TCACCGCTTG TACAGTTTGT TGTATCACAG TGACATAATT
 901  TTCAAACTCA GCCCTCAGGG CTACCGCTTC AGAAGTTAA GCCGAGTGTT
 951  GAATCAGTAC ACAGATACAA TAATCCAGGA AAGAAAGAAA TCCCTCCAGG
1001  CTGGGGTAAA GCAGGATAAC ACTCCGAAGA GGAAGTACCA GGATTTTCTG
1051  GATATTGTCC TTTCTGCCAA GGATGAAAGT GGTAGCAGCT TCTCAGATAT
1101  TGATGTACAC TCTGAAGTGA GCACATTCCT GTTGGCAGGA CATGACACCT
1151  TGGCAGCAAG CATCTCCTGG ATCCTTTACT GCCTGGCTCT GAACCCTGAG
1201  CATCAAGAGA GATGCCGGGA GGAGGTCAGG GGCATCCTGG GGGATGGGTC
1251  TTCTATCACT TGGGACCAGC TGGGTGAGAT GTCGTACACC ACAATGTGCA
1301  TCAAGGAGAC GTGCCGATTG ATTCCTGCAG TCCCGTCCAT TTCCAGAGAT
1351  CTCAGCAAGC CACTTACCTT CCCAGATGGA TGCACATTGC CTGCAGGGAT
1401  CACCGTGGTT CTTAGTATTT GGGGTCTTCA CCACAACCCT GCTGCTGTCT
1451  GGAAAAACCC AAAGGTCTTT GACCCCTTGA GGTTCTCTCA GGAGAATTCT
1501  GATCAGAGAC ACCCCTATGC CTACTTACCA TTCTCAGCTG GATCAAGGAA
1551  CTGCATTGGG CAGGAGTTTG CCATGATTGA GTTAAAGGTA ACCATTGCCT
1601  TGATTCTGCT CCACTTCAGA GTGACTCCAG ACCCCACCAG GCCTCTTACT
1651  TTCCCCAACC ATTTTATCCT CAAGCCCAAG AATGGGATGT ATTTGCACCT
1701  GAAGAAACTC TCTGAATGTT AGATCTCAGG GTACAATGAT TAAACGTACT
1751  TTGTTTTTCG AAGTTAAATT TACAGCTAAT GATCCAAGCA GATAGAAAGG
1801  GATCAATGTA TGGTGGAGG ATTGGAGGTT GGTGGGATAG GGGTCTCTGT
1851  GAAGAGATCC AAAATCATTT CTAGGTACAC AGTGTGTCAG CTAGATCTGT
1901  TTCTATATAA CTTTGGGAGA TTTTCAGATC TTTTCTGTTA AACTTTCACT
1951  ACTATTAATG CTGTATACAC CAATAGACTT TCATATATTT TCTGTTGTTT
2001  TTAAAATAGT TTTCAGAATT ATGCAAGTAA TAAGTGCATG TATGCTCACT
2051  GTCAAAAATT CCCAACACTA GAAAATCATG TAGAATAAAA ATTTTAAATC
2101  TCACTTCACT TAGCCGACAT TCCATGCCCT GACCAATCCT ACTGCTTTTC
2151  CTAAAAACAG AATAATTTGG TGTGCATTCT TTCAGACTTT TTCCTATACA
2201  TTTTATATGT AGAAATGTAG CAATGTATTT GTATAGATGT GATCATTCCT
2251  ATATTGTTAT TGATTTTTTT CACTTAATAA AAATTCACCT TATTCCTTAA
2301  AAAAAAAAAA AAAAAAAAA AAAAAAA
(SEQ ID NO:1)
```

FEATURES:
5'UTR:        1-189
Start Codon:  190
Stop Codon:   1720
3'UTR:        1723-2327

FIGURE 1A

Homologous proteins:
Top 10 BLAST Hits

```
                                                                    Score    E
gi|2117369|pir||A29368 prostaglandin omega-hydroxylase (EC 1.14...   521   e-146
gi|117166|sp|P10611|CP44_RABIT CYTOCHROME P450 4A4 (CYPIVA4) (P...   520   e-146
gi|164981|gb|AAA31232.1| (J02818) cytochrome P-450p-2 [Oryctola...   520   e-146
gi|1656|emb|CAA40493.1| (X57209) omega-hydroxylase cytochrome ...    518   e-146
gi|89989|pir||A34260 laurate omega-hydroxylase (EC 1.14.15.3) c...   517   e-145
gi|117167|sp|P14579|CP45_RABIT CYTOCHROME P450 4A5 PRECURSOR (C...   516   e-145
gi|203787|gb|AAA41038.1| (M57718) cytochrome P-450 IVA1 [Rattus...   510   e-143
gi|89992|pir||B34160 cytochrome P450 4A7 - rabbit >gi|164985|gb...   510   e-143
gi|3738263|dbj|BAA33804.1| (AB018421) cytochrome P-450 [Mus mus...   509   e-143
gi|8393238|ref|NP_058695.1| cytochrome P450, subfamily IVB, pol...   508   e-143
```

BLAST to dbEST:

```
                                                                    Score    E
gb|AW812435|AW812435 CM1-ST0181-261099-026-a02 ST0181 Homo sapi...  1092   0.0
gb|R56515|R56515 yg94d06.r1 Soares infant brain 1NIB Homo sapie...   769   0.0
gb|AA337301|AA337301 EST42040 Endometrial tumor Homo sapiens cD...   640   0.0
gb|AA652746|AA652746 ns65c09.s1 NCI_CGAP_Pr22 Homo sapiens cDNA...   636   e-180
gb|AA863360|AA863360 oh04f03.s1 NCI_CGAP_Kid3 Homo sapiens cDNA...   599   e-168
gb|AA319338|AA319338 EST21550 Adrenal gland tumor Homo sapiens ...   555   e-155
gb|BF355963|BF355963 CM1-HT0878-060900-398-b08 HT0878 Homo sapi...   381   e-103
gb|BF445825|BF445825 nae41d04.x1 Lupski_sympathetic_trunk Homo ...   365   5e-98
gb|AA557324|AA557324 n181a02.s1 NCI_CGAP_Br2 Homo sapiens cDNA ...   357   1e-95
gb|AV683266|AV683266 AV683266 GKC Homo sapiens cDNA clone GKCDQ...   323   2e-85
gb|AW264444|AW264444 xr03d03.x1 NCI_CGAP_Brn53 Homo sapiens cDN...   242   5e-61
```

EXPRESSION INFORMATION FOR MODULATORY USE:
library source:
Expression information from BLAST dbEST hits:
gb|AW812435|Stomach
gb|R56515| Soares infant brain 1NIB
gb|AA337301| Endometrial tumor
gb|AA652746| normal prostate
gb|AA863360| kidney
gb|AA319338| Adrenal gland tumor
gb|BF355963|head neck
gb|BF445825| Lupski_sympathetic_trunk
gb|AA557324| breast
gb|AV683266| hepatocellular carcinoma
gb|AW264444| brain Expression information from PCR-based tissue screening panels:
Whole brain

FIGURE 1B

```
  1 MEFSWLETRW ARPFYLAFVF CLALGLLQAI KLYLRRQRLL RDLRPFPAPP
 51 THWFLGHQKF IQDDNMEKLE EIIEKYPRAF PFWIGPFQAF FCIYDPDYAK
101 TLLSRTDPKS RYLQKFSPPL LGKGLAALDG PKWFQHRRLL TPGFHFNILK
151 AYIEVMAHSV KMMLDKWEKI CSTQDTSVEV YEHINSMSLD IIMKCAFSKE
201 TNCQTNSTHD PYAKAIFELS KIIPHRLYSL LYHSDIIFKL SPQGYRFQKL
251 SRVLNQYTDT IIQERKKSLQ AGVKQDNTPK RKYQDFLDIV LSAKDESGSS
301 FSDIDVHSEV STFLLAGHDT LAASISWILY CLALNPEHQE RCREEVRGIL
351 GDGSSITWDQ LGEMSYTTMC IKETCRLIPA VPSISRDLSK PLTFPDGCTL
401 PAGITVVLSI WGLHHNPAAV WKNPKVFDPL RFSQENSDQR HPYAYLPFSA
451 GSRNCIGQEF AMIELKVTIA LILLHFRVTP DPTRPLTFPN HFILKPKNGM
501 YLHLKKLSEC
```

FEATURES:
Functional domains and key regions:
[1] PDOC00001 PS00001 ASN_GLYCOSYLATION
N-glycosylation site
   206-209 NSTH

[2] PDOC00004 PS00004 CAMP_PHOSPHO_SITE
cAMP- and cGMP-dependent protein kinase phosphorylation site
Number of matches: 2
  1 265-268 RKKS
  2 505-508 KKLS

[3] PDOC00005 PS00005 PKC_PHOSPHO_SITE
Protein kinase C phosphorylation site
Number of matches: 4
  1 159-161 SVK
  2 278-280 TPK
  3 292-294 SAK
  4 374-376 TCR

[4] PDOC00006 PS00006 CK2_PHOSPHO_SITE
Casein kinase II phosphorylation site
Number of matches: 9
  1  4-7 SWLE
  2 104-107 SRTD
  3 172-175 STQD
  4 176-179 TSVE
  5 207-210 STHD
  6 292-295 SAKD
  7 300-303 SFSD
  8 302-305 SDID
  9 393-396 TFPD

[5] PDOC00008 PS00008 MYRISTYL
N-myristoylation site
Number of matches: 5
  1  25-30 GLLQAI
  2 298-303 GSSFSD
  3 353-358 GSSITW
  4 451-456 GSRNCI
  5 457-462 GQEFAM

[6] PDOC00081 PS00086 CYTOCHROME_P450
Cytochrome P450 cysteine heme-iron ligand signature
   448-457 FSAGSRNCIG

FIGURE 2A

Membrane spanning structure and domains:

| Helix | Begin | End | Score | Certainty |
|-------|-------|-----|-------|-----------|
| 1 | 12 | 32 | 1.638 | Certain |
| 2 | 76 | 96 | 1.029 | Certain |
| 3 | 316 | 336 | 1.077 | Certain |
| 4 | 395 | 415 | 1.443 | Certain |

BLAST Alignment to Top Hit:
```
>gi|2117369|pir||A29368 prostaglandin omega-hydroxylase (EC 1.14.15.-)
         cytochrome P450 4A4 - rabbit
         Length = 510

Score = 521 bits (1328), Expect = e-146
Identities = 246/493 (49%), Positives = 355/493 (71%), Gaps = 1/493 (0%)
Frame = +1

Query: 235  LAFVFCLALGLLQAIKLYLRRQRLLRDLRPFPAPPTHWFLGHQKFIQDDN-MEKLEEIIE 411
            +A +  L  LL+A +LYL RQ LLR L+ FP PP HW LGH +  Q+D  +E++++ +E
Sbjct: 21   VAALLGLLLLLLKAAQLYLHRQWLLRALQQFPCPPFHWLLGHSREFQNDQELERIQKWVE 80

Query: 412  KYPRAFPFWIGPFQAFFCIYDPDYAKTLLSRTDPKSRYLQKFSPPLLGKGLAALDGPKWF 591
            K+P A P+W+   +A   +YDPDY K +L R+DPK+     K   P +G GL  LDG WF
Sbjct: 81   KFPGACPWWLSGNKARLLVYDPDYLKVILGRSDPKAPRNYKLMTPWIGYGLLLLDGQTWF 140

Query: 592  QHRRLLTPGFHFNILKAYIEVMAHSVKMMLDKWEKICSTQDTSVEVYEHINSMSLDIIMK 771
            QHRR+LTP FH++ILK Y+ +M  SV++MLD WE++ S QD+S+E+++H++ M+LD IMK
Sbjct: 141  QHRRMLTPAFHYDILKPYVGLMVDSVQIMLDRWEQLIS-QDSSLEIFQHVSLMTLDTIMK 199

Query: 772  CAFSKETNCQTNSTHDPYAKAIFELSKIIFHRLYSLLYHSDIIFKLSPQGYRFQKLSRVL 951
            CAFS + + Q +     Y +AI +L+ ++F+R  ++  + SD +++LSP+G  F +  ++
Sbjct: 200  CAFSYQGSVQLDRNSHSYIQAINDLNNLVFYRARNVFHQSDFLYRLSPEGRLFHRACQLA 259

Query: 952  NQYTDTIIQERKKSLQAGVKQDNTPKRKYQDFLDIVLSAKDESGSSFSDIDVHSEVSTFL 1131
            +++TD +IQ+RK  LQ  +  +      +++DFLD++L AK E+GSS SD D+ +EV TF+
Sbjct: 260  HEHTDRVIQQRKAQLQQEGELEKVRRKRRLDFLDVLLFAKMENGSSLSDQDLRAEVDTFM 319

Query: 1132 LAGHDTLAASISWILYCLALNPEHQERCREEVRGILGDGSSITWDQLGEMSYTTMCIKET 1311
              GHDT A+  +SWI Y LA +PEHQ RCREE++G+LGDG+SITW+ L +M YTTMCIKE
Sbjct: 320  FEGHDTTASGVSWIFYALATHPEHQHRCREEIQGLLGDGASITWEHLDQMPYTTMCIKEA 379

Query: 1312 CRLIPAVPSISRDLSKPLTFPDGCTLPAGITVVLSIWGLHHNPAAVWKNPKVFDPLRFSQ 1491
             RL P VPS++R LSKP+TFPDG +LP G+ + LSI+GLH+NP  VW+NP+VFDP RF+
Sbjct: 380  LRLYPPVPSVTRQLSKPVTFPDGRSLPKGVILFLSIYGLHYNP-KVWQNPEVFDPFRFAP 438

Query: 1492 ENSDQRHPYAYLPFSAGSRNCIGQEFAMIELKVTIALILLHFRVTPDPTRPLTFPNHFIL 1671
            +++   H +A+LPFS G+RNCIG++FAM ELKV +AL LL F + PDPTR         +L
Sbjct: 439  DSA--YHSHAFLPFSGGARNCIGKQFAMRELKVAVALTLLRFELLPDPTRVPIPIARVVL 496

Query: 1672 KPKNGMYLHLKKL 1710
            K KNG++L L+KL
Sbjct: 497  KSKNGIHLRLRKL 509
```

Hmmer search results (Pfam):

| Model | Description | Score | E-value | N |
|-------|-------------|-------|---------|---|
| PF00067 | Cytochrome P450 | 416.5 | 2.5e-121 | 1 |
| CE00363 | E00363 glycine_receptor_beta | 2.1 | 4.7 | 1 |

FIGURE 2B

```
Parsed for domains:
Model      Domain  seq-f seq-t    hmm-f hmm-t      score  E-value
CE00363    1/1      210   233  ..   481   504 .]     2.1      4.7
PF00067    1/1       46   504  ..     1   497 []   416.5 2.5e-121
```

FIGURE 2C

```
   1  CCAGCCTCTC TTAGGCTCCT AAATATAGTG CAAAAAGTTC CAGAGTTCCT
  51  TTGTTACCCA TGAAAGCACA TGGAACGGTG CTGGACAGGG GCAACTGGCC
 101  CTGGAGCAGA GGAGTAACTG CATAGAACTG TCCAAGCCTC AGAGGGAGTC
 151  ACACCACCAG CAAGAACCTG GGTGGGAGTA GGTGAGCCAA GGGGTTCCCA
 201  GGCTCTGACC CTGCCAAGAG AACTCATTAG AAGGTCACCA ACCACACATA
 251  CTATTCCTCG GTCTCATGAA GAACCCAGGG ACCGGACCAG GCAAGATATC
 301  ACAAAGCTGA AGTTTCAGCT CTGGGCAGA GCATGGATCT GAGGTCTTTG
 351  GCCCTACCAC CATGCGATCA TATGAGGGCC ATCATACAAC CATCATGATT
 401  TGGGGGAGGA ATAGGGCATA GAGGAATCAT ATGAAAAGCT GAAATGCCAT
 451  GAGTTACCCA GAAGAAGCTG TGTAAGCCAG AGGATTCTGA GACCCTGTCA
 501  AATAACAACA TCTAGTTGAA GGTTGGAGTT AGGTAGGAGG TAGGGAAGTC
 551  TGGGAAAGAA GGAGCTGAAA CACTTGCTGT GTGTGGCTTA ATGAACATG
 601  CAAGGGGCCA GGACGAACTT GGTCCAGATG AAGTCACCAC CCCCTGGGGC
 651  CTGTCTTTTT TTTTTTTTTT TTTTTTTTTT TGAGACGGAG TCTCACTCTG
 701  TCACCAGGCT GGAGTGCAGT GGCGCGATCT CGGCTCACTG CAATCTTTGC
 751  CTCTCGGGTT CAAGCGATTC TCCTGCCTCA GCCTCCTGAG TAGCTGGGAT
 801  TACAGGCGCG CGCCACCACG CCCAGCTAAT TTTAGTACTG TTAGTAGAGA
 851  TGGGGTTTCA CCATCTTGGC CAGGATGGTC TTGATCCCTT GACCTCGTGA
 901  TCCGCCCGCC TCGGCCTCCC AAATTGCTGG GATTACAGGC GTGAGCCACC
 951  GCGCCCGGCC CCCTGGAGCC TGTCTTAATC ACTTACCCGC AAATAAAAT
1001  CTGGCTCCAG AGAGTGGAGC GTAGGCTTAA GGAATTGGGG GCGGAAGGGC
1051  GGGGAAGGTG GGGGAGGGAC AGTGATAGGG AGAACAGGGA ATTGTAGCAG
1101  AAATTGGGTT TATTGTTCAG AGCTGTCAAT GAACACTTAA CATATGCCTG
1151  TCTTAGCCTA AATCAATGAA TAAATAATG AATAAATAAA TGAATGAAAT
1201  GTGGGCAATG CCTATAAAGA TTGCTGGGAC AGGGAGGTGG GGGGAGACAC
1251  CAGCTTGGGA AGTCAGGCCT GTTAGATCCT AGTTCACCAC CTGATACGTT
1301  ACAAATACTA AAACCATCAC TTTCAAATTA TTTTTACTAC ATTTTCCTGT
1351  TATCTGTACT CGAGTTTATT TATGTTTCTG GCATCTAGAG TCAGCCCTTC
1401  ATGGGCATGA GACCCAAGCA GCCACACGAG GCTCTGAACC CAGAAGAGCA
1451  TATGCTCGGT TTAATGGTCT GTCATCTTAG AATTGTTAAT AAAGTTTTTA
1501  TCCCGCATTT TCATTTTGCA CTGAGATTCA TAAATTATAT AGCAGGCCCT
1551  GACTGTACCT GTATAGTGGA ATTACTATAT GATGGTACGC TACTGTGCAT
1601  ATCTTCCCCG TTCAGTGTTC AGTGCCCTCG TATCGGCAGC TTGAACTAGC
1651  TCATGGTACA CGCTGGGAAT CAGGGTGGGA ATCAGTTGTA AACCATTTAC
1701  CGGAACACCA CTAGGCAGGC CACAGGATAA AGGAATAATG ATGGTACACC
1751  TCCCCCTACC TCTACCACCT GGGAATTTTG GTAGAATGCC AGAATGGAAA
1801  AGAAAATCTC TTGCATAGCC ATTTATAATT TGTGATAAGG AAGAAAAACA
1851  ATGACCTCAG CTTTAGCATT ATTTTACAAT ATAAATTCAG ATCCCGTGAC
1901  TGAAAACTGT TGGACTTAAA AGAGGACGCT CCAGGAGCGC AAAAGCAGTT
1951  GGGCCGAACG AAGCGTGCGC GCTTTGGTAA CCGGCTAGAA ATCCCGCACG
2001  CGCGCCTGCC TCCTCTCCCC AGGCCTGAGC TGCCCCTCCC ACTGCCTTTC
2051  CTTCTTCCCG CGAGTCAGAA GCTTCGCGAG GGCCCAGAGA GGCGGTGGGG
2101  GTGGGCGACC CTACGCCAGC TCCGGCGGG AGAAAGCCCA CCCTCTCCCG
2151  CGCCCCATGA AACCGCCGGC GTTCGGCGCT GCGCAGAGCC ATGGAATTCT
2201  CCTGGCTGGA GACGCGCTGG GCGCGGCCCT TTTACCTGGC GTTCGTGTTC
2251  TGCCTGGCCC TGGGGCTGCT GCAGGCCATT AAGCTGTACC TGCGGAGGCA
2301  GCGGCTGCTG CGGGACCTGC GCCCCTTCCC AGCGCCCCCC ACCCACTGGT
2351  TCCTTGGGCA CCAGAAGGTA AATGGAAGGG AAAAAGGNTA GAAAAGGAGG
2401  AAGAGGGGGG CGGAGGAGGA TGCGGCAGAG GAGCCCAGCC GGCAGAGAGA
2451  CGCAGCTTTC TTCCATCCCT GGGGACCCTC CGGCTTGCAC CGGCCTTTCC
2501  AGCCCGGCCT GTGGCTCTTA GCATCATTTT TCCTTGCTCT GGAGAATTGC
2551  TTTCCCGCAG CCCCACAGGG AAAGGTCACA AAGAGGAAG CTTTGGGGGC
2601  TGGGAGAGAG CTATTTAAAG AACCTGAATA TGGAAAAAGA AAGCGAGCTG
2651  TAACTCAAGT CTGTCTCTCA TTGCTTCACC AAGCCTTCCA CATGTGTTGC
2701  TTTAAAAATA GCATGTTATT CTAAATAACT TATTAGTTGC AGAAAATATG
2751  CAAAATCTAT CCCAATCGTT GGCACCCTTA GTCCATTTTA ACAAGAGAAA
2801  ATTTTCTTTT CCTAAGATTC TTGTGAAGTA AGGAGCAGCC CCAGCCAGCC
2851  ACTCGAGAAA TACTGATTGA TGGAAATTTG TAAAGGGAGA CTGTTAGCTT
```

FIGURE 3A

```
2901  TTGGTCTCTC CCGTTTTTTA AATCCACTCC CACCCCTAAT TAAGGTTTTT
2951  ATTCATTCAA CCGACTCTGA GTGGCAATTG TGTGATAGGT ACTAAGATTA
3001  CAAAGAGAAG CTAAGTCCCT CCCCTGCACC ACCCAAGTCA GGTGCAGACT
3051  TAGGCCACAG AGAGAAAATG AAAATTTAAG GCAATGGGTG CTTTACTAGA
3101  GGCCTAGAGA CAAGGGAATA TCTGTCGGAG GAAAGTATAC ATCTCCGCCT
3151  AGAGAAGGAA GGAAAGTCTG TGAAGGGCTG AGCAGAGTCT TAAAGGATGG
3201  TTGGGTGGTG TGGGGAAGGC ATTCCAGCAG AGCTACTACA CGATCCTTTG
3251  GTTTCCCCAC TTTCTAGTCT TTCTTATATA AAGCAACCAC TTTCAACTCT
3301  TTTATCGGTT TCTTCTGGTA TTTAAATACT TATTTGTAAA ATAGTATTAC
3351  CATATTGCAT CTATTAATTT AATAAGTTTA GACATCTGCT GTGGTTTAGA
3401  TATGGTTTGT TCGTCCCCAC CAAGCCTCAT GTTGAAATTT GATTCCCAAT
3451  GTTGGAGGTG GGATCTGATG GGAGATCTTT GGGTCATTGG GATGGATCCC
3501  TCATGAATGT CTTGGTGCAG CTGTCTCCTT CATAAGTTCT CACTCTCTTA
3551  GTCCCTCTTC AACCCCAGA ACTGATTGTT GAAAAGAGCC TGCCACCTCC
3601  TCCCCTCTCT CTTCCTGTCT CTCACCATGT GGTCTCTGCA CACAACTGCT
3651  CCTGTTCACT TCCACTATGA GTGGAAGCAG TCTGAGATCC TCCGCAGATG
3701  CAGATGCCAA TGCCATGCTT CTTGTACAGC CTGCAGAATT GTAACCCAAA
3751  TAATCCTCTT TGTGAATGAC CCAGCCTCAG GTATTCCTTT ACAGCAACAC
3801  AAATGTACTA AGACAACATC CACCTATGAA CTTCTTTATG ACAGGCAATC
3851  ACTTACACTT CATATTCCAC TGTCCCAGTA ACTATATAGT ATTGTATTTT
3901  TTAAATAGAA AAACTTCTAT TTGTATTATT TTTATTATGC AAATGTTATT
3951  TACTGCTGAT CTAAATGGTC CTCTTTCATT TTATTTCCTT TTCTCATAGA
4001  ACTTTTTCCC CACCCCCACA GTATTGNNNN NNNNNNNNNN NNNNNNNNNN
4051  NNNNNNNNNN NNNNNNNNNN NNNNNNNNNN NNNNNNNNNN NNNNNNNNNN
4101  NNNNNNNNNN NNNNNNNNNN NNNNNNNNNN NNNNNNNNNN NNNNNNNNNN
4151  NNNNNNNNNN NNNNNNNNNN NNNNNNNNNN NNNNNNNNNN NNNNNNNNNN
4201  NNNNNNNNNN NNNNNNNNNN NTGTTATGTA TCTCTACTGT CTCATGAATA
4251  CTATGTCGTC TGTTGTTTTA ATTGAATTGT TTTGGCATCC TTGTCAAAAA
4301  TCAATTGACC ATAAATGTCA AGGTCTATTT CTGAGTCTTC AATTCTAATC
4351  CATTGATCTA TATGTCTATC CTAACTCATG GACACAGAGA GTAGAAGGAT
4401  GGTTACCAAA GGCTGGGAAG GATAGAGGGG AGCTGGGGGA GGAGGTAGGG
4451  AAGGTTAATG GGTACAAAAA AAATAGAAAG AATGAATAAC ACCTACTATT
4501  TGATAGCATA GCAGGGTGGC TATAGTCAAT AATAACTGTA CACTTTTAAA
4551  TAAAGAGTGT AATAGGATTG TTTGCAACTC AATGGATAAA TGCTTGAGGG
4601  GATGGGTACC CCATTCTTCA TGATGTGCCT ATTTCACATT GCATGCCTGT
4651  ATCAAAACA TCTCATTTAC TCCATAAATA TATACACCTA CTATGTATCC
4701  ACAAGTATTA AAAATTATAA ATAAATAAAT TATATAGCTA TCCTTATGCT
4751  AGTACCACAC TGCCTTACTG TTGCTTTGTA GTAAGCTTTG AAATCAGGAA
4801  GTATGAGTCC CCCGCACTTT GGTATTTTCC AAGATTATTT TGGCTGTTTG
4851  GAATCCTTGA TTTCTATACA AATTTTAGAC TCAGCCTATC AATTTCTACA
4901  AGGAAACCAG CTAGGGTTCT GCTTGGGATT GCACTGAATC TGTAGATCAG
4951  TTTGGGGATT ATTGCCATCT TAAGAATATT AGGTCTTCTG ATCCATGAAC
5001  ACAGAAAGCC TTTCCGTTTA GTTAGGTCAT CTTTAATTTT TTTTGTTGTT
5051  TTTTTTTGTT TTTTGAGACA GAGTCCTGCT CTGTCGCCCA GGCTGGAGTG
5101  CAGTGACGCA ATCTCGGCTC ACTGCAACCT CCGCCTCTCG GATTCAAGCG
5151  ATTCTCCTGC CTCAGCCTCC CAAGCAGCTG GGACTACAGG CACATGCCAC
5201  CACACCAACT AATTTTGTA TTTTCAGTAG AGACGGGGTT TCACCATATT
5251  GGCCAGGCTA GTCTCGAACT CCTGACCTCG TGATCCACCC GCCTCACCCT
5301  CCCAAAGTGC TGGGATTACA GGCGTGAGCC ACCACTCCCG GCTTTCTTTA
5351  ATTTTTTTA ACGATGTTTT TGTATTTTTC AAAGTATACA TCTTGCATTT
5401  CTTTTGTTAA ATTTATTTGT TTTGTTCTTT TTAATTTCAT TTCAGACTAT
5451  TTATTGCATT CATAGTGTTT TAGAGTCCAC ATTCCCTCTT GACTGTCACT
5501  AAGTTTTTTT TTTTCTGTTT TTGAGAGGTT TCTATCAGAA TTTTGCAGAT
5551  CAGAGATGAC GGACATGTCA AACTGTCTAA TATTACCAAC CCTCCCCATT
5601  TATCAGATCA GGATCCTTTT GGTGATTCAC CATGCAGGGA AATCTAGTAT
5651  CTAAGGCTCA AAAGGTGATA CTGTTTTACA TAGGCAGTAA CATTTTATTG
5701  CTACATAATA ACTACATATT TATGGAGTAC CTGTGATATT TGATACGTG
5751  CATACAATGT GCAGTGATCA AATCAGGGTG TTTAGGGTAT TCATCACTTC
```

FIGURE 3B

```
5801  TAACATTTAT TATTTATTTG TGTTTGGAAC ATTTCAAGTC TCTTCAAGCT
5851  CTTCAGAAAT ATTCAATACA TTATTGTTAA CAGTGCTATT GAACACTGGA
5901  ACTTATTCCT TCTATCTAAA GACAGTAACA TTTTAAGTAT AGTCATAAGG
5951  TTACAGAAGG ATAAAGTGTG TATAGGGAAA ATTCCCTACA AGATGAGAAT
6001  TTCATTCCTT ACTCTTAGTA ATACAGGTCT TCAAACATGC CAAGGATATT
6051  CCTCCCTTGG AGCTTTGAAC ATGCACGTCT GTGGTTATAT TGCTCTCCCT
6101  GCAAATTATT CCTAAAAGAG GCTTGCCCTG ACCATTCAGA CTAAAATAGC
6151  ACCTCTAGTA CTCTCTATCT CCAACCCTAT TATTATTATC TTGGCCCTTA
6201  TCACTCTCTG ACACTATACT GTATACTCTT TTGCTTGTTC GTTTATTATC
6251  CACCACTAAC TACAATATAA AATCTGTGAG AGGTAGGATC TTTGTTTGCC
6301  ACTATAAACC TAGTGCATGG TACAGTTCCT GGTGCATAAT AGGTGCTCAA
6351  TAAATCCTTT GTTGAATGCA TAAATATATT AGGTGCTGAG AAAATTTATT
6401  TATTCAAAGA TCAATTTACT GCATAGAATA GGCCAGGTGG TTTGACATTT
6451  ATTCAATAGC CAACATATGG GACCTAGGAT GTACATATGC AAGTGTGTGT
6501  GTGTATGTGT GTGTGCATCT GCATGTGTAC TTGGATGTAC TGCAGAGAAC
6551  ATCTATGTAG CTAAGTAGTA TAAAGCACTT GGGCTCCAGA GTTAAACTGG
6601  AGTTTGAATC CTCATTAGTG GTTGCCAGCT GTACACACTT GGGCAGATCA
6651  TTTAACCTAG TCTGTAGGGC TCAATTTCCT CATCTCTAAA GTAGGGATTG
6701  TAATCATATC TACTTCATAG GGTTCTTGAT GTAAATATTA AATAACATAG
6751  AACATGGAAA GCATTTAGCA GCACCTAGTT CATAGCAGTG CTTGATAAAT
6801  GTTCGCTGTT GCTATTTGGG GGCACTATGC ATTTTCTGAA CATTTCTGAA
6851  CAATGTTTAC TAAATATATG TAGTACCCGT TTTCAAGTGT ATTTAGATGC
6901  TTCTCTGGGG ATGAAGAAAT ATAAATTAAA TATAGTACAG TATTCACAAC
6951  AGTTTTCTGT CCTTTTTGTC TAGTCAGGAG TTACAAAAAG TATAATGAAA
7001  TACTTTCATA TGGCTGGGGT GTTTATGAAA ATTTTTTACC TAAACAAACA
7051  ATTGTCATAT TAGTTTACAA TATTCATGAG GGCAAAGGCC TTGTCTTCCT
7101  TATATTTCTC TGTATCTCTA CCACCTGGTA CGTGTGATAG ACAATAAATA
7151  CTTGTGTGTT TATTGTTTGT AAATGAATAA ATGAAAAAAT ATTCACATTG
7201  TTGAAAACCA CTACTCTGGA TAGTCAGTGG GTGCTTATCA CTGGCTTGAT
7251  TATGGCAACA TTAACAAAAA AGTGCAGTAT TTTAGAAACT AGGTTTCAAG
7301  ACTCTCAACC TTTCAGTGGC CTTGAACTAT CCAGAGAACA CTTTATGGGT
7351  TAAAATTGCT AAATGATAAC AGAGAAAAAT GGGAGCCAGA GTTGTCCACC
7401  TCTCCAGAGG ATGAGAGCAA ACAATCCTGC AGCAGATACC GTGTGATTGG
7451  TCACACGAGG AAAAATCTGG CAGCCTTAAG ATTACTTTGC AGCGGGGGAC
7501  TCCCACCATC ATGCTCAAGT GTGTAGATGG GCACACCAAA ACACACACAT
7551  GCAGGTGCCC TCCACTTTAC ACAAGAAGCA AATGTAAATG AATCTTGTTT
7601  TCAGTGATTT AGAGAAACAA TTTAAGTGAG CCATTACTCA TCTGCTTCTA
7651  AAAGCAAAAA CTCCTTCTCT GGTGGTAGTA TTTGCACTCT CATTTGTAAA
7701  TGTTGGAAGC TGAAAGTTTT GTATTTGAGT TTGCTTTAAG ATTCACACAT
7751  CTGTGTAAAT GGACCTTCTG TTGTTGGGGG GAGAATTTGG ATTTTCTTTA
7801  TAGATAGAGT TGGCAATTTT TTAGAGAGAA GCATTTACTG CTAAGTCATG
7851  AGAAATAATC ACTGGTGCAT AATTAGAGAG AGGAACAGGA AGAAGAAATG
7901  GTGAGCTGGA TGTAGGGTCA TGCCCCATTT AGTAACTGTT AGTTTCCCAC
7951  ATAGGAAATA CTTCTTTTTA GCTTCCAGAT CCCACTCCAA TCTGAGTGTG
8001  TGATGTTGGC AAGTGAGGCA GAGAGTGTGA CTCGGCTCAC CCTCTATTGG
8051  GACAAGAGTT CACAGTAAAT GTCATTCAAC AGTGACTTGG TCTGGGGGTA
8101  CAGGATATAT TAATATTGAG AAGATAAATA CACTAACTTT GTTTAGAGAA
8151  TTATCCCCCA AGCTTAGAAG TCCCAAAGAA AGCATGTTAT GTCACTTCCA
8201  GAAAAGTCTC AGGCTCCTCT GCTTGTGTGA CCTTATCAGG TCCTGAACTC
8251  AGCTTGTGTC TATAAGAGGG GACAGGTCCA GCTTGGCTGG CTAATTACTT
8301  TTACTTTTTT CACTGCAGTT TATTCAGGAT GATAACATGG AGAAGCTTGA
8351  GGAAATTATT GAAAAATACC CTCGTGCCTT CCCTTTCTGG ATTGGGCCCT
8401  TTCAGGCATT TTTCTGTATC TATGACCCAG ACTATGCAAA GACACTTCTG
8451  AGCAGAACAG GTAAGAAGAG GGGGAAAGCT CTGGGACCTA TTCCTCCTAG
8501  AAGTGAAATG CATAAAACCC ATAGGCAAGA TTCCAAAGCA AAGATTGGTT
8551  TGGGGCCTTT AAGAGACACA GCAGCAAGTA TGGGGAGGTG ACAGGTTTCC
8601  TACCAATACT GAAGGGGATT CCCATATCCT CCCCAGTCCC TTGTCTTGTT
8651  CAGGTATGCA TGGGCACGTT GAAGTCGGTA TAACTTAAAG CCTAGCTGGC
```

FIGURE 3C

```
8701  ATTACCAGAC TTGCCAGGCA AGGCTTCCCT TGGCCTCTGT GGGTTTTATG
8751  ACTTCAGTGT CAGCAACACT TCCCACTCCT ACCCCTGGTC TCGAGCATAA
8801  GTCTCAAGAG GGTGGGAAAT CAGCAGTAAC TCTACCTCTG CTGGTTCAGT
8851  ATGAAAGCCT GAATGCTAGA TCATTAATTT ACCCATCAGA CCTCTTGATN
8901  NNNNNNNNNN NNNNNNNNNN NNNNNNNNNN NNNNNNNNNN NNNNNNNNNN
8951  NNNNNNNNNN NNNNNNNNNN NNNNNNNNNN NNNNNNNNNN NNNNNNNNNN
9001  NNNNNNNNNN NNNNNNNNNN NNNNNNNNNN NNNNNNNNNN NNNNNNNNNN
9051  NNNNNNNNNN NNNNNNNNNN NNNNNNNNNN NNNNNNNNNN NNNNNNNNNN
9101  NNNNNNNNNN NNNNNNNNNN NNNNNNNNNN NNNNNNNNNN NNNNNNNNNN
9151  NNNNNNNNNN NNNNNNNNNN NNNNNNNNNN NNNNNNNNNN NNNNNNNNNN
9201  NNNNNNNNNN NNNNNNNNNN NNNNNNNNNN NNNNNNNNNN NNNNNNNNNN
9251  NNNNNNNNNN NNNNNNNNNN NNNNNNNNNN NNNNNNNNNN NNNNNNNNNN
9301  NNNNNNNNNN NNNNNNNNNN NNNNNNNNNN NNNNNNNNNN NNNNNNNNNN
9351  NNNNNNNNNN NNNNNNNNNN NNNNNNNNNN NNNNNNNNNN NNNNNNNNNN
9401  NNNNNNNNNN NNNNNNNNNN NNNNNNNNNN NNNNNNNNNN NNNNNNNNNN
9451  NNNNNNNNNN NNNNNNNNNN NNNNNNNNNN NNNNNNNNNN NNNNNNNNNN
9501  NNNNNNNNNN NNNNNNNNNN NNNNNNNNNN NNNNNNNNNN NNNNNNNNNN
9551  NNNNNNNNNN NNNNNNNNNN NNNNNNNNNN NNNNNNNNNN NNNNNNNNNN
9601  NNNNNNNNNN NNNNNNNNNN NNNNNNNNNN NNNNNNNNNN NNNNNNNNNN
9651  NNNNNNNNNN NNNNNNNNNN NNNNNNNNNN NNNNNNNNNN NNNNNNNNNN
9701  NNNNNNNNNN NNNNNNNNNN NNNNNNNNNN NNNNNNNNNN NNNNTCTGCT
9751  TGACTCTGCA GATCCCAAGT CCCAGTACCT GCAGAAATTC TCACCTCCAC
9801  TTCTTGGTAT GTATGTGCAA ATGAGAGGTA TAACCCACTC TCATTCAAAG
9851  TCCCCTTTCC ATAGTAGAGC ATGCCAAAGA AACTGAAATC TGAATTCAAA
9901  AGCACAAAGA GTGCAAGGTA GAGCTATACT GAACGTTATC TAGGGGAAAG
9951  ATTGAAGGGG AGCTCTAAGG TCAACACACC ACCACTTCCC AGAAAGCTTC
10001 TTCATCCGTT TCTCTCCCAC AAAGTCTTAT TCTCAAGGCA GCAGATACAT
10051 GAATCTGTCC CCTCTCTCTT TAAAACTACA GCCTTGGCCA GGCACAGTGA
10101 CTCATGCATG TAATCCCAGC ACTTTGGGAG GCCAAGGTGG GAGGATCACT
10151 TGAGGTCAAG ATTTCAAGAC CAGCTGGGCC AACATGGTGA AATCCCATCT
10201 CTACTAAAAA TACAAAAATT AGCCAGGCAT GGTAGCATGT AGGCCTGTAG
10251 TCCCACTACT TGGGAGGCTG AGACATGAGA ATCGCTTGAA CCTAGGAGGT
10301 GGAGGTTGCC GTGAGCTCAG ATTGTGCCAC TGCACTCCAG ACTAGGTGAC
10351 AGAGCAAAAC TCTGTCCGCA GCCCCCAACA ACAAAAAAAA AACTACCCAA
10401 ACTGCAGTCT CACCATCCCT ATTCTTGTTT TCTTTATCCT TCTCTCGTTT
10451 TCTTGGATGT TTTCCTTTCT TTTTGGAGTT CCTTTATTTC CACATGCGAG
10501 TCAGTAAAAT TTGCTCTAG AGTTTGGCAA TATTCTGTCA GCAGATAAAC
10551 TAAGCTCTTT AATTACATAA TTGGTATTTA TGTTAAACAA GACATGAATG
10601 AAAGAAAAGA ATATAGGCTT GTATTAGGAA CCACTTAAAT TTGAATCTTG
10651 CCCCCTCCTG CATTGACTAG TTAAATATGA TCTTGGGGAA GTCATTTAAT
10701 CTCTCCCTAT CTCAGTTTCC TCATCTTTGA CAATAAGGAT GAGACTCACA
10751 TTGCTGGGCT GTTATGAGGA TTAAATGAAA TACATATTTT TAGCACTACA
10801 TGTAATGGCC ACCATTGTAT GAGTGACAGA TCATGCATCA TGAGCCTGGA
10851 ATGTTGTAAG CATTCAATGA ATGGTATCAA TTATGTATTA ATAAACTTTA
10901 AAGTCCTTTT AAAGCCAAAT CCTAATGACC AGTCTGGCAA TAGAAGATTG
10951 TGAAGCATTA GCCTTGGTAA GTATTTCCAC ATAGTATCAT TCATAGACCT
11001 GGGCTCAAGG AGGAAATATC AGGGGACAGA GTGGACACTC TTGTCTCTTT
11051 CCTTGTGAAT TTATGTTCAT CATATAGTTT ATGGATTGT TTGGAGTGGA
11101 AAGGAATTCA CTTGCTCTGT TACTAGTGTG AGCTAGGGAG TAGGTTGGCT
11151 ACCTTATGTA TTCACTTTCA GTTAACCTCC ACAGCAACAC AGGGAAAAAG
11201 GTATTTAGTA TCATAGTTCA TTATTGAGAA AAGTAAACCT CAGGAAGATT
11251 GAGTCACTTA TTCAGTTACT ACATAGGTAG TAACTGGTGA TTTCAGGATT
11301 AGCGTGCTAA TCTTATAAGG CTTTGAAATT TATTAGACTT TGAAACTGTT
11351 TCTCACAATA TTAAATACAT CCATCCCAGA GGTAAGCTTC TAAATTCACC
11401 TTCATCTATT AAATTGCATT GCACATTAAT ACGAGTACTA CTTTGATACT
11451 CCACTGTTGC ATGACTGCCT GTGGGTCATG GTTACTCCAC GCTGCCTGTG
11501 TTCCTCATCT ATCCTTCATC TCATCTAATT AAATGGCATA AGGTTTTCTG
11551 CCTTTTATTT CTCAAGGAAA AGGACTAGCG GCTCTAGACG GACCCAAGTG
```

FIGURE 3D

```
11601  GTTCCAGCAT CGTCGCCTAC TAACTCCTGG ATTCCATTTT AACATCCTGA
11651  AAGCATACAT TGAGGTGATG GCTCATTCTG TGAAAATGAT GCTGGTAAGT
11701  AAAGGGGGAA AGTGCTCTGT GCATTGCGAA ATGCTCCCAG CAATGGACAG
11751  TATTAGGTAT GTGTTTTGTG GGCCATGAAA ATAAAAAATC AGTTTCTAAA
11801  AATTTAACCA ATGTACACGT ACTTATTGAA CAATAGGTGT CTGTAAAAAA
11851  TTTGTTATGT TCTTTGAGTG ATAATATTAA TAAAAAGATC TGGTCCTCTG
11901  TCTTAGATAT ATTTTGAGAT TTTATGGCAG CAAACCAAGT ACCAAATGGT
11951  GATAGTTAGA TAGTAAGTGC TGTAGATGTG TTTCATGGAG GGCGGGTCTG
12001  TACAAACCTA CCCCAAAGTC TGAGGAAACT GAGAGGCTGA AGAAAAAGGC
12051  TGACAGTTTC TTAAAAAGAA ACATTCAATA GAGGCTTTCA AACAAAAACC
12101  ATNNNNNNNN NNNNNNNNNN NNNNNNNNNN NNNNNNNNNN NNNNNNNNNN
12151  NNNNNNNNNN NNNNNNNNNN NNNNNNNNNN NNNNNNNNNN NNNNNNNNNN
12201  NNNNNNNNNN NNNNNNNNNN NNNNNNNNNN NNNNNNNNNN NNNNNNNNNN
12251  NNNNNNNNNN NNNNNNNNNN NNNNNNNNNN NNNNNNNNNN NNNNNNNNNN
12301  NNNNNNNNNN NNNNNNNNNN NNNNNNNNNN NNNNNNNNNN NNNNNNNNNN
12351  NNNNNNNNNN NNNNNNNNNN NNNNNNNNNN NNNNNNNNNN NNNNNNNNNN
12401  NNNNNNNNNN NNNNNNNNNN NNNNNNNNNN NNNNNNNNNN NNNNNNNNNN
12451  NNNNNNNNNN NNNNNNNNNN NNNNNNNNNN NNNNNNNNNN NNNNNNNNNN
12501  NNNNNNNNNN NNNNNNNNNN NNNNNNNNNN NNNNNNNNNN NNNNNNNNNN
12551  NNNNNNNNNN NNNNNNNNNN NNNNNNNNNN NNNNNNNNNN NNNNNNNNNN
12601  NNNNNNNNNN NNNNNNNNNN NNNNNNNNNN NNNNNNNNNN NNNNNNNNNN
12651  NNNNNNNNNN NNNNNNNNNN NNNNNNNNNN NNNNNNNNNN NNNNNNNNNN
12701  NNNNNNNNNN NNNNNNNNNN NNNNNNNNNN NNNNNNNNNN NNNNNNNNNN
12751  NNNNNNNNNN NNNNNNNNNN NNNNNNNNNN NNNNNNNNNN NNNNNNNNNN
12801  NNNNNNNNNN NNNNNNNNNN NNNNNNNNNN NNNNNNNNNN NNNNNNNNNN
12851  NNNNNNNNNN NNNNNNNNNN NNNNNNNNNN NNNNNNNNNN NNNNNNNNNN
12901  NNNNNNNNNN NNNNNNNNNN NNNNNNNNNN NNNNNNNNNN NNNNNNNNNN
12951  NNNNNNNNNN NNNNNNNNNN NNNNNNNNNN NNNNNNNNNN NNNNNNNNNN
13001  NNNNNNNNNN NNNNNNNNNN NNNNNNNNNN NNNNNNNNNN NNNNNNNNNN
13051  NNNNNNNNNN NNNNNNNNNN NNNNNNNNNN NNNNNNNNNN NNNNNNNNNN
13101  NNNNNNNNNN NNNNNNNNNN NNNNNNNNNN NNNNNNNNNN NNNNNNNNNN
13151  NNNNNNNNNN NNNNNNNNNN NNNNNNNNNN NNNNNNNNNN NNNNNNNNNN
13201  NNNNNNNNNN NNNNNNNNNN NNNNNNNNNN NNNNNNNNNN NNNNNNNNNN
13251  NNNNNNNNNN NNNNNNNNNN NNNNNNNNNN NNNNNNNNNN NNNNNNNNNN
13301  NNNNNNNNNN NNNNNNNNNN NNNNNNNNNN NNNNNNNNNN NNNNNNNNNN
13351  NNNNNNNNNN NNNNNNNNNN NNNNNNNNNN NNNNNNNNNN NNNNNNNNNN
13401  NNNNNNNNNN NNNNNNNNNN NNNNNNNNNN NNNNNNNNNN NNNNNNNNNN
13451  NNNNNNNNNN NNNNNNNNNN NNNNNNNNNN NNNNNNNNNN NNNNNNNNNN
13501  NNNNNNNNNN NNNNNNNNNN NNNNNNNNNN NNNNNNNNNN NNNNNNNNNN
13551  NNNNNNNNNN NNNNNNNNNN NNNNNNNNNN NNNNNNNNNN NNNNNNNNNN
13601  NNNNNNNNNN NNNNNNNNNN NNNNNNNNNN NNNNNNNNNN NNNNNNNNNN
13651  NNNNNNNNNN NNNNNNNNNN NNNNNNNNNN NNNNNNNNNN NNNNNNNNNN
13701  NNNNNNNNNN NNNNNNNNNN NNNNNNNNNN NNNNNNNNNN NNNNNNNNNN
13751  NNNNNNNNNN NNNNNNNNNG GTCAGGCTTT GCTGGGGGCA GCTCCCTGCA
13801  ACAGCTCCTC TCCACACTTG CTCTGTTTCT CACTTTTGAA TCCAAACGTT
13851  TTTGAAAATG TTCTGAGTTT ATTTTAAAAT GTGGCTATGG TGGTTGAGAG
13901  CAGTGGCAGG GTACCTAGCA AGTTTGGAAT TGAAGTTGGA GGAAGCCCTG
13951  GGGTAAACCC CTTGTAATTA TGGGTCTTGT GTCAATGATT GCTTTAATGG
14001  AACTCTGGTC TGTTTGAAAG CAGAGTTATG GTAATAATTG AAAAGCCGCA
14051  GATCTTTAAC TCAGCCATTT ACCATATATG CAGTTTTCTC CATGCTCCTT
14101  CTCACTCCGC TGGGTGTATT TTTCCCTTCC TCGTGCCCTG TGTAAGCACA
14151  TGGCTTATTT ACTCATGTGA TCTTTGGTTC CTGCTGGGTC AGGGTTGTCT
14201  CCATTAGATC ATAAAAACAG GGCCAGGCAG GAGCCTTCAA ATGAAGGCAA
14251  TTTGGTCATG GTGGTGGTGA TGATGTTGGT CTTGACCTCC TGTGCCAGGA
14301  TAAGTGGGAG AAGATTTGCA GCACTCAGGA CACAAGCGTG GAGGTCTATG
14351  AGCACATCAA CTCGATGTCT CTGGATATAA TCATGAAATG CGCTTTCAGC
14401  AAGGAGACCA ACTGCCAGAC AAACAGGTCA GTGGTGGGAG AGCAAAAAAG
14451  ATATTTCTTC ACATTTTCTA AGTTGTTTAT TAACACATTA TCCCAACTTT
```

FIGURE 3E

```
14501  CTCTTCTAGC ACCCATGATC CTTATGCAAA AGCCATATTT GAACTCAGCA
14551  AAATCATATT TCACCGCTTG TACAGTTTGT TGTATCACAG TGACATAATT
14601  TTCAAACTCA GCCCTCAGGG CTACCGCTTC CAGAAGTTAA GCCGAGTGTT
14651  GAATCAGTAC ACAGGTATTT GTTGGGTTTG GGTTGCCCAC GTCCATACGC
14701  TGCCATGATT GTACTGTGTC TGTCTAGAGG GATAAACCTT AATATGACAA
14751  GAGAAAGAAT CTTTGTTATT AATGGAGCTT TTATATAGAC ACTGCTCCAA
14801  AGAAATTTGA CTTGAGTCCT TTATAAGACT TTGCTTCAAC CATAGCAGTA
14851  TTATCAGAAT TTTTATATAT ATATATATAC ACTATTTTTA TTATGGACAA
14901  TTATTATTAA TACAAATATA AGTAGGCACT TAAGAGTTCC AGACATACAT
14951  GGAATATGGC TTTTTGCACA GCGATTGCAG TAATAATAAT GACAAGCTAA
15001  AAACATTCAT GCAACATAGG AATGGAGAGT GGAACAGAGT AAACATGGAC
15051  ATGCACCCGA AAGAATATTG ATTCAAAAAC AGTTTTAGCA AGCATAAACA
15101  CAAAAGTTGA AATAGATTAA GCTTTTTAAG CAATTCAACA TTACTTGTCA
15151  TGAATGCCAT AATGGAGAAT ACTTATCAAG CAGTGAATTA ATCCTTCATC
15201  AGCTTCACCA CTTACTAGCA GTTACTAGTA AGTTACTTAC TGCTTTGTTT
15251  CAGTGTCATC TATAAAATGG AGATTAAAAA AGAACCTATC TCATACATTT
15301  GTTGTTACGA TGAGTGGGTT AATATATATA AAGCATTTAG GACAGTGCCT
15351  GGCACTGAAT AGATGTTAAA TGTAAAGTAT AGTTATGTCA AATGTCTTTG
15401  CTTCCAGGAA TTTTGCAAGA CACACCAACA TATGCACACT TACACATACA
15451  TATATGCATA CATGCACATA GATATTATAA AGAGGACACT CAGAGAAGCA
15501  GGTTATAAAC AATTTAAGGC ATAAATGGGC ATTATAAATA GCAGCAGTTC
15551  CCAAGTCTTT CTGCATCATT GCACACACAG AAAATGTTAA TGTTTTTGTG
15601  CTTCATTGGA GTAAACAGGA ATGGATTTGG GGGAAGCTAT ACAGAACTTT
15651  GTAAAAAAAA ATCTTTACTT TTTAAATATT ATACAATTAT GATGAAAAAG
15701  CAAAATGCAA AGTGTTAGGG AAAATATTAA ATGTTAAATT TATTCAAAAC
15751  TTAAAACCTT TTCAATTTTT TTTTTTTTTT TTTTTGAGA TGGAGTCTCT
15801  ATCACTCAGG CTGGAGCGCA GTGGTGTGAT CTCAGCTCAC TACAACCTCC
15851  ACCTCCCAGG TTCAGGCAAT TCTCCTACCT CAGCCTTCTG AGTAGCTGGG
15901  ATTACAGGCA CTGCCACCAC ACCTGGCTAA TTTTTTTAAA TTGTTTATTT
15951  TTATTTAGTC AAATATATCA ATATTTTATT TTATTGCATC TGGATTTTTA
16001  GTAATCACAA AAAGCCATTC TCTATTCCAG GGTTTCTCAA CCCTCAGCAC
16051  TAATGGCTTC TTAGATTAGA TAAGTCCTTG TTGTCAAGAT GTGTGCATTG
16101  TAGGATGTTT AGCTACATCC CTGACATCTA CCCACTCGAT GTAGTAGAGC
16151  TCTGATAGTT ATAGCAACCA TAAATAACTC CAGACATTAT TGAATGTTCC
16201  CAGGGCCCCC AGTTGAGAAC CACTGCCCTG TACCCAGGTT GTAGAGAAAA
16251  TTATTTATGT TTTCTTGTAG TACTTGTATA ATTTCATTAT TTTCATATTT
16301  AAATCAGAGA TCTAAACTCC ATTTAGAATT TATTCCTATA TATGGTGTGA
16351  GGTATTGATC TAATTTTTCC AAATGTTTAT CCAGTTGTCC CATCACCATT
16401  ATTTAAAAGT TTATCTTTTC AAGTGATTTG AGATAACCAT CACATTCTAA
16451  ACGGATACAT GTACTGGTAT CTGTTTTGGA TAAGAGTATA TTTGGATGTT
16501  CTCGTGTATT CCATTGATCT ATCTACCAAT GTACCAGAAT CACACTGTTT
16551  TAATTAAGGA GATTTTGTGG CTTTTTTCAA CATTAATAGA CCTTATTTTT
16601  AGAAAAGTTT TAGGTTTGCA GAAAAATTCA GCAGAAAGTA CAGAGAGTTC
16651  TCATATTACC CATGTAACAA ACCTGTACAT GTACCCTGT ATCTAAAATA
16701  AAAGTTGAAA TTTTTTAAAT AGTAAATAAA TATTACCTCT GTTCCATATT
16751  TTTGTTTTGT TTTTTTTCTC TCAGCTCCTT CAATTATAAA TATATTGGCA
16801  TTTCTTTGCC TGTCTTCTAT TTCATTCCAT TTTATTTAAT AACTTTTCCG
16851  TGAAGATAAA ATATTAGACT GAGGAAGAAA AGAATAATTG GTCACTTGCA
16901  TCTAAACTTG AAATCATCTT AATTTTATTG CCCACATACT GATGGAAACT
16951  ATGTTTTTTA TTTGTGTTGT TTATCTTTGG AGCTTTAATC AAAAGTCCCT
17001  TTGATGAGAA AATAAACCAT CTGTGAAAAT TAGATCTATT TAAACGTCTG
17051  GAAATCAGGC AAGATTTGAA GCTATTCACT AACCATGGCT TGCTTTATAA
17101  TTTATTTGAC TTTGCCATCA CTTTGGTAAT TGGAAACTAT TTTTCTACCC
17151  AGATACAATA ATCCAGGAAA GAAAGAAATC CCTCCAGGCT GGGGTAAAGC
17201  AGGATAACAC TCCGAAGAGG AAGTACCAGG ATTTTCTGGA TATTGTCCTT
17251  TCTGCCAAGG TAAATCTTCT AAATTTCTAA GCCTGCTCAA GTGACCAGTT
17301  AATTATGTAA GTAGGTGGGT AAGTGGGAAT GGGATGGGGA GACAAGAATA
17351  AAACCGATTG ACTAAATTTA ACTGTACTTT GAATTGATGA GCAGCTTCAT
```

FIGURE 3F

```
17401  GCAATTTGAG ACAAAGAGAG AATTCTGCAA CTGTGTCGCT AGAGGAGGGT
17451  TAGTAAAGAC TAAACGAACG ATTTGACAAG ATTTGAGGAT TGTCATATGG
17501  ATACATGGAT TTTAGGGCAT CATGAAAAAA TGGTCACATG GATAAACGTA
17551  AAAATTATGA TGATAAGGTC CTGGGAAATC TGGGAGTTTG AAGAGAATTT
17601  CTAGGGCCTG TTGATCGAGG GCCCTTTGTG CAAGGCCTGC TTTTCTTATC
17651  TAACCTTGGT TCTCCTTTAT GCTTTGGGCA GAATATGGTT TATACCACAT
17701  ATTTGTTGAA CTGAATTAAA ATTTAAACCC CTATTTAAAG CTCTGATTTT
17751  TCCCCTCAAA TCATTATTGT GGTTGTATCT CCAAACATTT ATAAACTGGC
17801  ATTTTATTTA AAATATTTGT ATTGTACTTT CTAGGATGAA AGTGGTAGCA
17851  GCTTCTCAGA TATTGATGTA CACTCTGAAG TGAGCACATT CCTGTTGGCA
17901  GGACATGACA CCTTGGCAGC AAGCATCTCC TGGATCCTTT ACTGCCTGGC
17951  TCTGAACCCT GAGCATCAAG AGAGATGCCG GGAGGAGGTC AGGGGCATCC
18001  TGGGGGATGG GTCTTCTATC ACTTGGTAAG ATCTGCACCC CTAAATTTTC
18051  CTGCTAGTTT TCCCCCTGAG ATTTTGCTTT ATTTTTTGCG CTGGTACCTT
18101  AGTGACCCTA GTGCCTCAGG ATATGTGTAG GTGAAACAGA AGAAGTAGGC
18151  TACTTTTCTG TTCTTTCTAA AGAGAGCTCC AAATTATTCT CTTGTCTTTC
18201  AGGAAAAAAA AAAAAGTTTA TTTATCCATA AATTGTCTGT CATTGGTTTT
18251  CTAATCAATG GTGTGTGAAA TGTCTTATTT CTTTATTTCA CCTTGGCTCT
18301  GATGCATTGG AAATGAGGAC TTGATCCCTG GGCTGGCACT TAGAACTTAA
18351  ACAATAGGGT CCAAGTGGAG CTCCTCTTCT GAGAGAGCTG AATGATTAGC
18401  TGCATTATTT AAGGCTCATT TTAGACATCT CCCAGCCGCT TGTCACCAAT
18451  TTTATTCCTC AGGATTGATT TTAGACTTCA GACATAATAT TCGATGATAT
18501  ATACTATAGT TAAGTTTAGC AAATATGGAC TGAGGACATT TTAAATACTG
18551  AGACTTTTTT TATGACTACA ATTTATTGTG GGCCCTGTCT TCGGTGAGCT
18601  AATGGTCTAA TACAGGAGAC AGGAGACAGA CCTCCAAATT GCAGTGTAGC
18651  ATAATGAGGG CAATGATAGA GATATGTGCT GGCTAACACA AAGACATAGA
18701  AGACAGGTAC CTACCCTGGC ATGGGAGCTC AAGGAGACTT CCTTGACATT
18751  TACGCTGACT GCAGGATAAG TAGGAGTTAG CCAGGTGGAA ACTGTCATCT
18801  CTATCTTGCT AGACTTTAAG CATATACTGC TGTTAATAAA GCCCAGGTTA
18851  TGCTGTTTGC AAAGATAAAA TGTGTTCCTG ACATAATACT GGTCAAAGGG
18901  ACAGAAAGAC AGAAATGCTA AGGACAATTC AGCAGCAGAC CAGATAAAAA
18951  ACACCATATT TCATATGCAA AAGTCAACTC AATTGAAACA TTTGTAAAAC
19001  CAAATTTGAC ATTATAAAAG TATATCAGAG ATCTCATTTT ATAAGGAAAT
19051  AGAAGCCCTT TCCTACCATA AACTAAAGAT TTAATCTATA TAGCACAAAA
19101  TACAATGTTG AGTAATCATT TTAATTTAT TTTTTAACTG ACAAAAATTG
19151  TGCATATACA TGTTATATAT ATATGTATGT GTGTATATAT ATATGATGTA
19201  CAACATGATA TTTTGATATA TGTATACACT GTGGAATGAC TAAATCTATC
19251  AATGGACATG TTCATTAACT CATACTTATC ATTTTTTGT GGTAAGGACA
19301  TTTAAAATCT ACCCTCTTAG CAATTTTCAA GTATACAAAT TGTTAGTAAC
19351  TCCAATCACA TATTGTACAA TGCATCTCCT AAACTTATGC CTCCTGTCTG
19401  ACTGAAATTT TGTATCCTTT GACTAACATC CCTGTAATCC CCCATTCTCC
19451  CACAGCCCCT GGTAACCACT GTTCTACTCT CTGCTTCTTT GAGTTTAATG
19501  TTTTAGATTT CCACATGTGA GATCATGTGG AATTTGTCTT TCTGTGCCTG
19551  GCTTATTTCA CTTAGCATAA TGTCATCCAA ATTCATCTCT GTTGTCATAA
19601  ATGACAAGAT ATTTGTCTTT TCTATGGCTA ATTGTTAGTC CATTGTTTAT
19651  ATATATACCA TGTTTCTTT ATCCATTTAT CCAGTGATGG ACACTTAAGT
19701  TGATTTCTAT ATCTGGGCTA TTGTGAATAA TGCTGCAATG AACATGGGAA
19751  TGTAGATGTC TCTTCAATGC ACTGATTTCA TTTCGTTTGG TTGTATATCC
19801  AGAAGTGGAA TTGCTGCATC ATATGGTAGT TCTATTTTA ATTTTTTGAG
19851  GAAACTCCGT ACAATTTTCC ATATGGCTGT ACTAATTTAC ATTCCAACCA
19901  AAAGTGTATA AGGGTTCTGT TTTCTCCACA TCCTCACCAA CATTTGTCTT
19951  TTTGGTAATA ACCATTCTAA TGAGCATGAG GTGATGTCTC ATTATGGTTT
20001  TAATTTACGT TTCCCTGATG ATTAGTGATG TTGAGCATTG TTTTAAATAC
20051  CTGCTGGCCA TTCATGTCTT CTTTGTAGGA ATGTTATTTT AGGTTTTTCT
20101  CATTTTTAAA TCTAGTTATT TGTTTTCTTG CTTTTGAATT GTGTGAGTTC
20151  CTCATATATT TTGAATATTA ACCCCTATC AGATGTATCA TTTGCAGACA
20201  TGTTCTCCCA TCCTTTAAGT TGTCTCTTCA CTATGTTGAT TGTTTCCTTT
20251  GTTGTGCAGA AGCTTTTTAG TTTGCTGCAA AACCATTTAT CTATTTTTC
```

FIGURE 3G

```
20301  TTCTGTTGAC TATACTTCCA GAGTTGTATC CAAAAAATCA TTGCCAAGAA
20351  TAATATCAAG AAGCTTTTCT CTATGTTTTT TTCTAGTAGT TTTATAGTTT
20401  CAGGTCATAT GTTTAAATCT TTAATCCATT TTTGTTGAT TTTTGTATAT
20451  GGAGTGAGAT AAAGGTCCAC TTTTATTCTT CTACTAGTGC ATATCCAGTT
20501  TTCTCAACAC CATTTATTGA AGATACTGCC CTTTCACCAC TGTATGTTAC
20551  TGGAACCTTT GTAGATCAGT TGACAATAAA TGTGTGGGTG TATTTCTGGA
20601  CTCTTTATCC TGTTTTATTA GTTTATATGT CTCTTTTTTT AGAAGCTCTA
20651  TGCTGTTTTG GTGACTAGAG CTCTGTAGTC AATTTCAGAT CAGGTAGTAT
20701  GATGCACTCC AGCTTTGCTC TTTTTGCTCA AAATTGCTTT GGCTATTTGA
20751  GTTTTTTTAT TCCATACGAA TTTTAGGGCT TTTTTTTTTT TTCGATTACT
20801  GTGAATAATG CCATTGGAAT TTTGATGGAG ATTGCATTGA ATCTTTGGGT
20851  AGTATGGATA TTTTAACAGT ATTAATGCTT CCAATTAATG AACACAGGGT
20901  ATTTTGCAAT TTGTGTTTTC TTCAATTTCT TTCACCAGTG TTTTTTTCTT
20951  AATTTAATTG TTTTATTTCC ATAGGGTTTG GGTAACAGGT GGTGTTTGGT
21001  TATGAGTAAG TTCTTTAGTG GTGATTTGTG AGATTTTGAT GCACCCATCA
21051  CCTAAGCAGT ATACACTGTA CCCAATTTGT AGTCTTGTAT CCCTCACCTC
21101  CCTCCCACCA TTTCCCCCAA GTCCCCAAAG TCCATTGTAT CATTCTTATG
21151  CCTTTGCATC CTCATAGCTT AGCTCCCACT TATGAGTGAG AACATATAAT
21201  GTTTGGTTCT CCATTTCTGA GTTACTTCAT TTAGAATATT GGTCTCCAAT
21251  TCCATCCAGA TTGCTGCGAA TGCCTTTATT TTGTTCCTTT TCATGGCTGA
21301  GTAGTATTCC ATAGTATATA CATCCCACAA TTTCTTTATC CATTCTTGAT
21351  TGATGGGCAT TTGGACTGGT TCCATGTCTT TACAATTGCG AATTGTGCTG
21401  CTACAAACAT GCAGGTGCAA GTGTCTTTTT CATATAATGA CTTCTCTTCC
21451  TCTGGGTAGA TACCCTGTAG TGGGATTGCT GGATCAAATG GTAGTTCTAC
21501  TTTTAGTTCT TTAAGGAATC TCCACACTGT TTTCCATAGT GGTTGTACTA
21551  GTTTACATTC CCACCAACAG TGTAGAAGTG TTCCCTGTTC ACTGTATCCA
21601  CACCATCATC TATTATTATT TGATTTTTTG ATTATGGCCA TTCTTGCAGG
21651  AGTAAGGTGG TATTGCACTG TGGTTTTGAT TTGCATTTCC CTGATCATTA
21701  GTGATGTTGA GCATTTTTTC ATATATTTGT TGGCCATTTG TACATCTTCT
21751  TTTGAGAATT GTCTATTCAT GTCCTTTGTC CATTTTTTGA TGGGATTATT
21801  TGTTTTTTTC TTGCTAATTT GAGTTCCCTG TAGATTCTGG ATATTAGACC
21851  TTTGTTGGAT GTGTAGGTTG TGAAGATTTT CTCCCACTCT TTGGGTTGTC
21901  TGTTTACTCT GCTGATTATT TCTTTTGCTG TGCAGAAACT TTTTAGTTTA
21951  ATTAAGTCCC ACCTATTTAT CTTTTCGTTG TTGTTGTTTT TTGGGGTTGT
22001  TTTGTTTTGG CTTGGTTTTG CATCTGCTTT TGGGTTCTTG GTCATGAAGT
22051  CTTTGCCTAA GCCAATATCT AGAAGGGTTT TTCTGATGTT CTAGAATTTT
22101  TATGGTTCAG GTCTTAGATT TAAGTCCTTG ATCCATCTTG AGTTGATTTT
22151  TGTATAAGGT GAGAGATGAG GATCCAGTTT CATGCTTCTA CATGTGGCTT
22201  GCCAATTATC CCAGTACAAT TTGTTGAATA GGGTTAATAT TTAAAGCTTT
22251  ATATATTTAG GTGTTCCTAT TTTGGGTACA TATTTATTTA CAACTATCAT
22301  ATCCTCCTGA TGGATTGACC CCTTTCTCAT TATATAATGG TCTTCTTGTC
22351  TCTTTTTACA GTTTTTGTCT TAAAGCCTAA TTTGTCTGAT AAAAGTTCAG
22401  CTACCTTTGC TCTCTTTTGG TTTCTATTTG CATGGAATAT TTTTTTCCAA
22451  CCCTTCGCAT TCACTCTATG TGTGTTCTTA AAGATGAAAT GAGATGCTGT
22501  AGGGGCATAT GCTTGGGTCT TGTTTTATTC ATTCATTCAG CCACCCTTTT
22551  GATTAGAGAA TTTAATTCAT TTGTATTCAA GGTAATTATT GACAGACAAG
22601  GACTTACTAC TGCCATTTTG TTAATTGTTT CTTGATGTT TTATAGATCT
22651  TTTGTTCCTT TCATCCTCTC TTACTCTTTT CCTTTGTGAT TAGGTGCTTT
22701  TCTCTAGTGG TGTACTTTGA TTTTTACTTT TTATCTTTTG TTGCTCTACT
22751  ATAGGTTTTT GCTTTGTGGT TACCATGAGG GTTACATAAA GCATAGTTAT
22801  AAAAGGCTAT TTAAACTGA TAACAGCTTA ACTTTCAACA CTTAAAAAAA
22851  CTATACACTT TTACTCTACC AACTGCCCTC CATTTATGT CTTTGATGTC
22901  ATAATTTACC TAGTTTTGGA GATGTGTCCC CTTATTGTGT ATCCCTTAAC
22951  AAATTATTGT AGCAACAGTC ATTTTAATA GTTTGGCTT TTAACTTTAT
23001  ACTAGAGATA GAATTAATTA ACATACCACC ACTACATTAT TAGGGTATTC
23051  TAAATTGACT ATGTATTTAC CTTTATCAGT GAGATTTTTG TTTTCAATTT
23101  TCATGTTGTT AATTAGTATT CTTTCATTTC AACTTGGAGA ATTCACATTA
23151  GCATTTTTTG TAAGATGGGT CTAGTAGTGG TGAACACCCT CAACTTTTGT
```

FIGURE 3H

```
23201  TTATCTGGAG ATGTCTTTAC CTCTGCTTCA TTTTGAAATA TAACTTTTGT
23251  TCCATGATTG AAATGGACAA AATTGTTTTT TTAATTATGC AAAGTGCCAG
23301  GGTAAGCAGA ATTACTCTTT TTTTTTTTTT CTGAGACCGA GTTTCACTCT
23351  TGTTGCCCAG GCTGGAGTGC AGTGGCGCAA TCTCTCAGCT TACCGCAACC
23401  TCTGCCTCCC AGGTTCAAGC GATTCTTCTG CCTCAGCCTT CCTGAGTAGC
23451  TGGGATTACA GGCATGCACC ACCATGCTCG GCTAATTTTG CATTTTTAGT
23501  AGAGACGGGG TTTCTCCATG TTGGTCAGGC TGGTCTTGAA CACCCGACCT
23551  CAGATGATCC GCCCACCTAG GCCTCCCAAA GTGCTGGGAT TGCAGGTGTG
23601  AGCCACTGCG CCTGGCCAGA ATTACTCTTA TTTATCCTGA GCTTGAGGAA
23651  GAAAGAATTC AAAATTAAAA TTTCACATTA CCTAATGGCC AAAGCCTGCA
23701  TTCAAAATAA GTAATCAGAA AAACATATAA AAACACAATA AGATAAACAG
23751  ACTAAATATA TGCAGTCATT TTATGGAACC AATCTGACTA GATTGGATGC
23801  AGACTAGGTA GGATGCAAAT TTAAAAAAAA CTTTATTCTT CTTCCACTTA
23851  TAAACTTTAA ACCTGCTTTG TGGAGCAAGT TCTTTTTATC TCTGGGGAAA
23901  GATCCTGAGT AAGTCTCATA GAGTTCTCAT TCATTTAAAT CACAAGAACA
23951  ATCTTAGGTC AGTAATTAAA CTATCTGGCC CAGTGTAATA CTGAAACTTT
24001  CAAATACTTA TCCACTTGAG CTCTTCTTTC CATCCCAGCT TGGTACTTCT
24051  TTGGTCCTAG AAGCCAGCAG TGGTTTATCA TCGACTTATT CTTACTGACT
24101  AGCTCCCCAA TACCCAGTAG CTGCTGTTTC TGGCCCCTCC AGGAATGGTT
24151  TTAGGAGGAA AGGGGATAAG GAGTAAAGGG CTGGTACTAT TGTGATCATG
24201  CCAAAGGGCT TGGTGGATAT TCCATGCTTC CCTTTCTCTC AAGAGGAAAC
24251  TCCCTTTCTT GGAGACTCTC TCACTAGAAC TTTCCAGAGG TGATTCAGGG
24301  GACAAGAGAA TAATTGTCCT TAGGCAGACT CTTTTTCAAG CTGGTCCCAG
24351  AGCTTTCCCT CTTGCCAGTT AATTGGTTTA AGGACACAGT TGCACATCCT
24401  TGCCTTGCCT CTGCTGCTGT CCTCTGCCTT TCTGTCTGTT CTGAGTTATA
24451  GCCTTTCACA TCAGTCCTGT ACTCCCAAA CTCCAAGGAG CACAAGTCAG
24501  ATCATCTAAG TGATCCTCTT GAAGCCTCTT GTTTAAGATG GGGGAAGCAC
24551  CCTTCCTTTT CCATGGCACT CTGGCATTCC AACAACACTT TAAATAATTT
24601  TTTCTCTCAA AATTCTTAAG CCTCTCCTCT TTAATCCTTC GCCATTTTTA
24651  TGTATTATTA CTTTATATGA TGAGCTAAGA GTTACAAAAC TGGTTTTTAG
24701  AAATCTCCTT AGCAAATGTT TTACTGCTAG TTTAGCAGCT CACTTTATAA
24751  TAAGGATATA TGATATATTT CTTTGGTTCC TCTGCCTCTG GGACCTCAGC
24801  TCATCCTGAG GCAGAGAGTC CCATTTAAC ATTCTGTTAC ATAAACCAGT
24851  GGCAAAATGG CTTTAACCTG AGGGTAATAA TTACCAGGAA CAAACAGAAA
24901  ACAGAAAAAA AGTAAACTGG TTATGATATC TGAGTCCCTT CCCTCCCTCA
24951  TCCTCACAGG GACCAGCTGG GTGAGATGTC GTACACCACA ATGTGCATCA
25001  AGGAGACGTG CCGATTGATT CCTGCAGTCC CGTCCATTTC CAGAGATCTC
25051  AGCAAGCCAC TTACCTTCCC AGATGGATGC ACATTGCCTG CAGGTCTTTA
25101  CATTCTTTTC CTAAGCAGTT CTTAGAGGCT ATGGGATCCT GGAGACCACA
25151  GTGACAAAGA TTAGTGAGTC TCTTAGCACT TGGAGAAGTC AAAAGATAAT
25201  GCTAACATGT GACTTAGGTT TTATCACCTA TGAGGAGCTC AGAGGATAAT
25251  GCTTTGGTCA GACATGAATT TCAATGACTT TCCCAAAGGC ACATAGCCAG
25301  TTGCAGCAAA GCTAAGCCCA GAATCCATGT CTCTGGAATC CCAGCCCAGG
25351  GTCTCTTCCA TTGTGGGACA TCATTTCTAA GATAATCTTT GTTTGGCTGA
25401  GTTTGAGACC GAGCTGAAAC TTCATGGAAA ATAGCACCAG CATCTTTATC
25451  TGAAAGACCA AGGGGGATCT TTGGCCTCAT CATCATAATA TCACCCTTAT
25501  AAATATACAA CATTTAATAG TTAATATAGA GCCTTCAGAC CCATTATCTC
25551  ATTTTTCCCC TTGGAATCCA ATGTTAACAG ATGCTTATAC AATGATTTAC
25601  AGTTCACTGA ACACTTTTAA GTACTTTCAA TGTGGCCCAA AATCCAGAGG
25651  CAGCCCCAAT GTGTAGATGA CATTAACTGA TGTGAGCAGA GCTAGAACTT
25701  GTGCGGAGAC CCTGAGTCTG GAGCCTAGAG TTCTTCGGAA CAACACAGGT
25751  TTCTGAGCAG GGCTTATAGG AAGCAGAGGG GTCATGTGAG ACATATTATC
25801  TGATTCAATG TTCTATTAAT TCATGTCTTA GGAAGCAAGC CAACAGGATT
25851  GCTTCTGGCA AACACCTACA GCCTGTTACT GTAACTTTGC TGACAGACCC
25901  AGAATTAATT TCTGGAAGCT AGAATTATTT CTGGAAACCA AATAACCCTC
25951  ACATTCTCTC TCCTTTGTTT TGTACTCTGT TTCTCCCCAA ACCACATGGA
26001  TATTTGCCAA AATTCTCCAC TTTCCATATG TGAATAGCAC CAATGGAAAT
26051  TTGTCATGGG ATCTGCATGA CAGAATCACA GTTCTGTGTG TGTGTGTGTG
```

FIGURE 3I

```
26101  CGTTTTCCTC TCAAGACAGA GTCTTGCTAT GTAGCCCAGG CTGGAGTACA
26151  GTGGCGTAAT CTCGGCTCAC TGCAACCTCT GCCTCCCAGG TTTAAGCAGT
26201  TCTCCTGCCT CAGCCTCCCG AGTAGCTGGG ATTACAGGTG CACACCACGC
26251  CTGGCAAATT TTTGTATTTT TATTAGAGAT GGGGTTTCAC CATGTTGGCC
26301  AGGCTAGTCT CAAGCTCCTG ATCTCGAGAC CAGCCCTCCT CAGCCTCCCA
26351  AAGCGCTGGG ACTACAGCCA TGAGCCACTG CACCCAGCCA GTTCTGTGCT
26401  TTTATACCTA AATTGTCTCC AGGAGTGCTT AATAGTCCAT TAATAGGTAT
26451  TTAGGCCAGG CACAGTGGCT GACGCATATA ATCCCAATAT TTTGTGACAC
26501  CAAGGTGGGA AGACTGCTTG AAGTTAGGAG TCTGAGACTA GCCTGGGCAA
26551  CATAGGGAGA CCCTGTCTTT ACAAAAAAAA AAAAGAGAGA GATAGCCAGG
26601  CATGGTGTTG CATGCTTGTA TTCCTGCCTA CTTGGGGGAC TGAGGCAGGA
26651  GGATCACTTG AGCTCAGAAG TTCAAGGTTA CCGTGAGCAA TGTTCACGCC
26701  ACTGCTCTCC AGCCTGATTG ACAGGCCAGA CCCTGACTCT AAACAAAAAC
26751  AAAAAACAAA TATTTAAGTA ATTTCCAAAC ATAGCAGAAA ATATAAGCAT
26801  GGTTTATCAC TTTGATATGA CACCAACAGC TACTTAAGAT AGAGTCATGA
26851  ATTCAGTAAA TTGTTGTGTG GAAAGCTAAG GTGCCAACCC AAGCCGCATC
26901  TTCTTAGGTG CTCCTCACTG GTGTCATCAG CTACAGCAGG CAGAGCATTG
26951  CCAGGAGCTA GCTCTTCCCT TCAAGAACAA AAGTCTTGTT TAAGAGCACA
27001  GTAGCCCACA ACTTGCTCTT TCTCCTGCAG TCTCTTTTAT TTCCCTCCTT
27051  TCTTAGGGAT CACCGTGGTT CTTAGTATTT GGGGTCTTCA CCACAACCCT
27101  GCTGTCTGGA AAAACCCAAA GGTATGATTC TCTCTTGTAC ATAAATACTT
27151  CCAAGAACTA ATGCTGTGCA AGTCACTTTT TGGTAGCTAA GCACAGAAGT
27201  GGCTATATAA TTAAGGGAAA TGACACAAAT TAAACAAAAA TAAACATAAA
27251  AGCCAAAAGA AATGTAAAAC TATTCTATGT TCTTGAAACA CTCTTGACGT
27301  GTATCAGTGA TTTCTTTCAT GTAAGCCACT AAGGTTTAAG ATCTATTACT
27351  TGTAACAGGA AGCTGGAGTA TATGTCTCTG TAATAATTGG CCACATCATC
27401  ATTTTGACTT GATTTCTAAG TGGATGCACA TCCATTTCTA AGTGGATGTA
27451  TCTCCATAGT GAAAATAATA CCACTTGCCA TAGTATTTTT GTTTGCCTGG
27501  GTATCAGACA AATCAGCTGT GAAGCTGCAA GGTCTGCAGG TCTGAAGGTA
27551  CACTGCCCAG TGTAGTAGCC ACGGGCCACA TACGGCTACT GAGCACATGA
27601  CATGTGGCCA GTTGGAATTG AGTTGTGCTG TAAGTTTAAA ATACGTGCTG
27651  GATTTTGAAG ACATAGTACC CTAAAAAAAT GTGAAACATT TCCTTTTAGT
27701  AATTATTTAT ATTGATTACA GGTTGGAATG GTAATTTTTG GTTAAATAAA
27751  CTCTATTAAG ATTAACTTCA CCTTTTAAAA ATGTGACCAC CAGAACATTT
27801  TAAATTACAC ATGTAGATCA CATTATATTT CTATTGATCG GTGCTAGGTG
27851  GTAGGTGAAG AAATGTGTTC ATGTTGTTTG GGGGATGGTG TTGGGGTTGT
27901  CCTCTCATTT CAGGTCTTTG ACCCCTTGAG GTTCTCTCAG GAGAATTCTG
27951  ATCAGAGACA CCCCTATGCC TACTTACCAT TCTCAGCTGG ATCAAGGTGA
28001  GAACAATTTG AAGTTGCTGA AAGTACCCAA AGATGTTTAC TTGAGAGTAG
28051  TTTATTCCTT TCAGCTCCTC AGCTCTATAC ATTCTTCCAG GGAACCGTAG
28101  ATCTTGGTGC CTATTTGAGC CCCAAAGGAT CAGTTAGTTT TACAAAGGAC
28151  AATCGTATTC TCTGTCACAT CCTTTTTGGC CATGCCTCAA AAGCAGTCCC
28201  ACAATGTAAG CTACTGCTCA TAGGCTCAAT GCAGTCCACC TTCAAAGCAA
28251  GAGAAATAAT TTCATGAGTA ACTCCAACTG CCGCCTTGTT ATAGGGAAGG
28301  CATCATGTTG GAGCCTCCCA GCTCAAATTC TCACAGTGAA CAATTTAAGT
28351  CTAAAGTTCA AAAGTTTCAA TGGCATTTGG TGGAAAAAAT ATCACTTTAC
28401  TGTGTACTTC AGACTTCTTG TACTAGTATT TTACTATAGT CAGAAGAAAC
28451  ATCATTTTTT CAAGTATCAC TTTCTTTCCC TCTTGTCTTC AGGAACTGCA
28501  TTGGGCAGGA GTTTGCCATG ATTGAGTTAA AGGTAACCAT TGCCTTGATT
28551  CTGCTCCACT TCAGAGTGAC TCCAGACCCC ACCAGGCCTC TTACTTTCCC
28601  CAACCATTTT ATCCTCAAGC CAAGAATGG GATGTATTTG CACCTGAAGA
28651  AACTCTCTGA ATGTTAGATC TCAGGGTACA ATGATTAAAC GTACTTGTT
28701  TTTCGAAGTT AAATTTACAG CTAATGATCC AAGCAGATAG AAAGGGATCA
28751  ATGTATGGTG GGAGGATTGG AGGTTGGTGG GATAGGGTC TCTGTGAAGA
28801  GATCCAAAAT CATTTCTAGG TACACAGTGT GTCAGCTAGA TCTGTTTCTA
28851  TATAACTTTG GGAGATTTTC AGATCTTTTC TGTTAAACTT TCACTACTAT
28901  TAATGCTGTA TACACCAATA GACTTTCATA TATTTTCTGT TGTTTTTAAA
28951  ATAGTTTTCA GAATTATGCA AGTAATAAGT GCATGTATGC TCACTGTCAA
```

FIGURE 3J

```
29001  AAATTCCCAA CACTAGAAAA TCATGTAGAA TAAAAATTTT AAATCTCACT
29051  TCACTTAGCC GACATTCCAT GCCCTGACCA ATCCTACTGC TTTTCCTAAA
29101  AACAGAATAA TTTGGTGTGC ATTCTTTCAG ACTTTTTCCT ATACATTTTA
29151  TATGTAGAAA TGTAGCAATG TATTTGTATA GATGTGATCA TTCCTATATT
29201  GTTATTGATT TTTTTCACTT AATAAAAATT CACCTTATTC CTTATCATTG
29251  CTTTATGGTA TTCTGTAATA TGAATGTACT ATAATTTATT TAACTATTTT
29301  CCTTATTGGG CATTTAAGTT ATTTCTAGTT TTAAAAACAT GCTTGTCAAT
29351  GGCAACAAAA GCCAAAATTG ACAAATGGGA TCTAATTAAA CTAAAGAGCT
29401  TCTGCACAGC AAAACAAACT ACCATCACAC TGAATGGGCA GCCTACAGAA
29451  TGGGAGAAAA TTTTTGCAAC CTACTCATCT GACAAAGGCC TAATATCCAG
29501  AATCTACAAT GAACTCAAAC AAATGTACAA GAAAAAAACA ACCCCATCAA
29551  AAAGTGGGTG AAGGATATGA ACAGACACTT CTCAAAAGAA GACATTTACG
29601  CAGCCAAAAG ACACATGAAA AAATGCCTAT CGTCACTGGC CATCAGAGAA
29651  ATGCAAATCA AAACCACAAT GAGATACCAT CTCACACCAG TTAGAATGGC
29701  AATCATTAAA AAGTCAGGAA ACAACAGGTG CTGGAGAGGA TGTGGAGAAA
29751  TAGGAAGACT TTTACACTGT TGGTGGCAGG AGAATCACTT GAACCCGGGA
29801  GGGGGAGGTT GCAGTGAGCC GAGGTGGCGC CACTGCACTC CAGCCTGGGC
29851  GACAGAACGA GTACTCCATC TCAAAAAAAA AAAAAAAGGA CACCAAACTT
29901  CTCAATCTTA ATGTTGTCAT CTATGTGGTA TCTTCCATAA TCTCTCTCAG
29951  ACAGAGTCAT CTTTTGCTGA TATGATCTTA CAGTATTTTT TGTTTATACC
30001  ATTATAATCT CATTAATTGC AGCAACACAA ATGACAAAAG ACAACTGATT
30051  TCTCCCCTTG GATGACCTAA TTTGCTTTCA CTCTTCCATC ATCACTTATA
30101  ACATGATGAT TCTCAAATTC ATCTACCTAA AATCTATATA TAAAAAAATC
30151  CCTCCCTTGA ATTCCAGATC CTTGGAGACA AACACCCACG TCTAAAACCA
30201  AATTTGTTTA ACACTGGACC AGTCGTCCTG TGTGACTTTC CATTTTGTCA
30251  CTATTTGTC AGCTGGTATA CCAATATCCA CCCAGTTAAA CAATATTTCC
30301  TTGTTTTTTT CTGGTACAAA CCCAAATAAA TTACAAACAT CAATAAAAGT
30351  AAAATTCTAA AATAACTCAC TTTCTCTATA TATCTCCTTC TTGCTGGAAA
30401  AATGGGTTAG GTTAGTTCTT TAAAAGCATG CATGATAAAT TGTACTGAAT
30451  ACAATATTCA GGTCTGGACA TACTAGGTAT AATTTTCTGT GTCTCTGGGG
30501  TCTTACCTAT TTGGGGTCAA AATAAACAAG TTTATTAAGC TTATTAATAT
30551  TCAATTTCAT TATCTTCTTT AACAATTATG TTCCCTAGGTA GTTTCATTGC
30601  CAATAATTTA TTTGTCAGGT TGCCAGGTGC TTCTAAACTT CTGTGTATTT
30651  TTTCATATCC AATTTTACTT TAAATATTTT TAGAAAAGAG GTCTGTTAAA
30701  TTTCCTAATA ATTATTATAT TATTGTTTTT TCACTGACAT TTTGTGAATT
30751  GAAACCCTT AAAAATATGA AATCATTTTT TCGAAATATG TGCCACAGAC
30801  AATTTTGTTA AATAAGAAGA CAGAAACAGG GCATTATCAA GAGATAAATA
30851  TTCAATATAC CTTATATTTC TGTCACACAT TTTTATACCA ACTGTGCCAA
30901  AAATTGTATA TCATATAAAT GATAACAAGT TCACAAAGGC ATTCCTTTAT
30951  CCCTTAACTC TCAAATTAGA AACTTTCATA GGTAGGAAGT AGGGGAAGCA
31001  TATATTCCCT TTGAAAGGTG CAAGAAAATG TCATTGGCAT TCACCATGGT
31051  ACTCTTCAAG CTTAAAAAAA ATGGACTGCA AAACATTTAC AAACATAGCA
31101  TATTTATTGG GTACCTTTAT GTTTACATAA ATATTGAAGA TATCTCACAT
31151  ACCTCTTTCA ATCAGATTAT CTCACTGACA TTTATTGACC ACTTTCTATG
31201  GGGAAAAC
```

FEATURES:

| | |
|---|---|
| Start: | 2191 |
| Exon: | 2191-2367 |
| Intron: | 2368-8318 |
| Exon: | 8319-8460 |
| Intron: | 8461-9761 |
| Exon: | 9762-9806 |
| Intron: | 9807-11566 |
| Exon: | 11567-11694 |
| Intron: | 11695-14298 |
| Exon: | 14299-14426 |
| Intron: | 14427-14509 |

FIGURE 3K

```
Exon:        14510-14664
Intron:      14665-17152
Exon:        17153-17259
Intron:      17260-17834
Exon:        17835-18025
Intron:      18026-24959
Exon:        24960-25093
Intron:      25094-27056
Exon:        27057-27121
Intron:      27122-27913
Exon:        27914-27996
Intron:      27997-28492
Exon:        28493-28664
Stop:        28665
```

CHROMOSOME MAP POSITION:
Chromosome 1

ALLELIC VARIANTS (SNPs):
DNA

| Position | Major | Minor |
|---|---|---|
| 267 | T | C |
| 284 | G | A |
| 1269 | T | C |
| 2487 | T | C G |
| 4486 | G | A |
| 4522 | G | A |
| 4522 | C | A |
| 5075 | T | G C |
| 5450 | T | C |
| 5450 | T | C |
| 5995 | G | A |
| 6241 | G | A |
| 8479 | C | T |
| 10045 | C | A |
| 10045 | G | A |
| 11994 | G | A |
| 14070 | A | G T |
| 15535 | T | C |
| 17618 | C | T A |
| 18520 | A | - C |
| 18525 | - | T A |
| 18525 | - | G A |
| 19189 | T | C A |
| 19259 | C | T |
| 19325 | G | T |
| 19346 | G | T |
| 20845 | - | T |
| 20845 | T | C |
| 22234 | T | C |
| 22234 | G | T |
| 22247 | C | T |
| 22334 | A | G |
| 23033 | T | - |
| 23036 | - | A |
| 23421 | A | G |
| 25582 | T | C |

FIGURE 3L

| | | |
|---|---|---|
| 26407 | C | A |
| 26473 | C | T |
| 26844 | G | A |
| 28384 | A | - |
| 28417 | A | C |
| 29265 | A | G |
| 29484 | A | G |
| 30417 | T | - |
| 30783 | C | G |

Context:

DNA
Position

267
```
CCAGCCTCTCTTAGGCTCCTAAATATAGTGCAAAAAGTTCCAGAGTTCCTTTGTTACCCA
TGAAAGCACATGGAACGGTGCTGGACAGGGGCAACTGGCCCTGGAGCAGAGGAGTAACTG
CATAGAACTGTCCAAGCCTCAGAGGGAGTCACACCACCAGCAAGAACCTGGGTGGGAGTA
GGTGAGCCAAGGGGTTCCCAGGCTCTGACCCTGCCAAGAGAACTCATTAGAAGGTCACCA
ACCACACATACTATTCCTCGGTCTCA
[T,C]
GAAGAACCCAGGGACCGGACCAGGCAAGATATCACAAAGCTGAAGTTTCAGCTCTGGGGC
AGAGCATGGATCTGAGGTCTTTGGCCCTACCACCATGCGATCATATGAGGGCCATCATAC
AACCATCATGATTTGGGGGAGGAATAGGGCATAGAGGAATCATATGAAAAGCTGAAATGC
CATGAGTTACCCAGAAGAAGCTGTGTAAGCCAGAGGATTCTGAGACCCTGTCAAATAACA
ACATCTAGTTGAAGGTTGGAGTTAGGTAGGAGGTAGGGAAGTCTGGGAAAGAAGGAGCTG
```

284
```
CCAGCCTCTCTTAGGCTCCTAAATATAGTGCAAAAAGTTCCAGAGTTCCTTTGTTACCCA
TGAAAGCACATGGAACGGTGCTGGACAGGGGCAACTGGCCCTGGAGCAGAGGAGTAACTG
CATAGAACTGTCCAAGCCTCAGAGGGAGTCACACCACCAGCAAGAACCTGGGTGGGAGTA
GGTGAGCCAAGGGGTTCCCAGGCTCTGACCCTGCCAAGAGAACTCATTAGAAGGTCACCA
ACCACACATACTATTCCTCGGTCTCATGAAGAACCCAGGGACC
[G,A]
GACCAGGCAAGATATCACAAAGCTGAAGTTTCAGCTCTGGGGCAGAGCATGGATCTGAGG
TCTTTGGCCCTACCACCATGCGATCATATGAGGGCCATCATACAACCATCATGATTTGGG
GGAGGAATAGGGCATAGAGGAATCATATGAAAAGCTGAAATGCCATGAGTTACCCAGAAG
AAGCTGTGTAAGCCAGAGGATTCTGAGACCCTGTCAAATAACAACATCTAGTTGAAGGTT
GGAGTTAGGTAGGAGGTAGGGAAGTCTGGGAAAGAAGGAGCTGAAACACTTGCTGTGTGT
```

1269
```
CCTGTCTTAATCACTTACCCGCCAAATAAAATCTGGCTCCAGAGAGTGGAGCGTAGGCTT
AAGGAATTGGGGGCGGAAGGGCGGGGAAGGTGGGGGAGGGACAGTGATAGGGAGAACAGG
GAATTGTAGCAGAAATTGGGTTTATTGTTCAGAGCTGTCAATGAACACTTAACATATGCC
TGTCTTAGCCTAAATCAATGAATAAATGAATGAATAAATAAATGAATGAAATGTGGGCAA
TGCCTATAAAGATTGCTGGGACAGGGAGGTGGGGGAGACACCAGCTTGGGAAGTCAGGC
[T,C]
TGTTAGATCCTAGTTCACCACCTGATACGTTACAAATACTAAAACCATCACTTTCAAATT
ATTTTTACTACATTTTCCTGTTATCTGTACTCGAGTTTATTTATGTTTCTGGCATCTAGA
GTCAGCCCTTCATGGGCATGAGACCCAAGCAGCCACACGAGGCTCTGAACCCAGAAGAGC
ATATGCTCGGTTTAATGGTCTGTCATCTTAGAATTGTTAATAAAGTTTTTATCCCGCATT
TTCATTTTTGCACTGAGATTCATAAATTATATAGCAGGCCCTGACTGTACCTGTATAGTGG
```

2487
```
AGCCATGGAATTCTCCTGGCTGGAGACGCGCTGGGCGCGGCCCTTTTACCTGGCGTTCGT
GTTCTGCCTGGCCCTGGGGCTGCTGCAGGCCATTAAGCTGTACCTGCGGAGGCAGCGGCT
GCTGCGGGACCTGCGCCCCTTCCCAGCGCCCCCCACCCACTGGTTCCTTGGGCACCAGAA
GGTAAATGGAAGGGAAAAAGGNTAGAAAAGGAGGAAGAGGGGGGCGGAGGAGGATGCGGC
AGAGGAGCCCAGCCGGCAGAGAGACGCAGCTTTCTTCCATCCCTGGGGACCCTCCGGCTT
[T,C,G]
CACCGGCCTTTCCAGCCCGGCCTGTGGCTCTTAGCATCATTTTTCCTTGCTCTGGAGAAT
TGCTTTCCCGCAGCCCCACAGGGAAAGGTCACAAAAGAGGAAGCTTTGGGGGCTGGGAGA
```

FIGURE 3M

```
       GAGCTATTTAAAGAACCTGAATATGGAAAAAGAAAGCGAGCTGTAACTCAAGTCTGTCTC
       TCATTGCTTCACCAAGCCTTCCACATGTGTTGCTTTAAAAATAGCATGTTATTCTAAATA
       ACTTATTAGTTGCAGAAAATATGCAAAATCTATCCCAATCGTTGGCACCCTTAGTCCATT

4486   TGTTATGTATCTCTACTGTCTCATGAATACTATGTCGTCTGTTGTTTTAATTGAATTGTT
       TTGGCATCCTTGTCAAAAATCAATTGACCATAAATGTCAAGGTCTATTTCTGAGTCTTCA
       ATTCTAATCCATTGATCTATATGTCTATCCTAACTCATGGACACAGAGAGTAGAAGGATG
       GTTACCAAAGGCTGGGAAGGATAGAGGGGAGCTGGGGGAGGAGGTAGGGAAGGTTAATGG
       GTACAAAAAAAATAGAAAGAATGA
       [G,A]
       TAACACCTACTATTTGATAGCATAGCAGGGTGGCTATAGTCAATAATAACTGTACACTTT
       TAAATAAAGAGTGTAATAGGATTGTTTGCAACTCAATGGATAAATGCTTGAGGGGATGGG
       TACCCCATTCTTCATGATGTGCCTATTTCACATTGCATGCCTGTATCAAAAACATCTCAT
       TTACTCCATAAATATATACACCTACTATGTATCCACAAGTATTAAAAATTATAAATAAAT
       AAATTATATAGCTATCCTTATGCTAGTACCACACTGCCTTACTGTTGCTTTGTAGTAAGC

4522   TGTTATGTATCTCTACTGTCTCATGAATACTATGTCGTCTGTTGTTTTAATTGAATTGTT
       TTGGCATCCTTGTCAAAAATCAATTGACCATAAATGTCAAGGTCTATTTCTGAGTCTTCA
       ATTCTAATCCATTGATCTATATGTCTATCCTAACTCATGGACACAGAGAGTAGAAGGATG
       GTTACCAAAGGCTGGGAAGGATAGAGGGGAGCTGGGGGAGGAGGTAGGGAAGGTTAATGG
       GTACAAAAAAAATAGAAAGAATGAATAACACCTACTATTTGATAGCATAGCAGGGTGGCT
       [G,A]
       TAGTCAATAATAACTGTACACTTTTAAATAAAGAGTGTAATAGGATTGTTTGCAACTCAA
       TGGATAAATGCTTGAGGGGATGGGTACCCCATTCTTCATGATGTGCCTATTTCACATTGC
       ATGCCTGTATCAAAAACATCTCATTTACTCCATAAATATATACACCTACTATGTATCCAC
       AAGTATTAAAAATTATAAATAAATAAATTATATAGCTATCCTTATGCTAGTACCACACTG
       CCTTACTGTTGCTTTGTAGTAAGCTTGAAATCAGGAAGTATGAGTCCCCCGCACTTTGG

4522   TGTTATGTATCTCTACTGTCTCATGAATACTATGTCGTCTGTTGTTTTAATTGAATTGTT
       TTGGCATCCTTGTCAAAAATCAATTGACCATAAATGTCAAGGTCTATTTCTGAGTCTTCA
       ATTCTAATCCATTGATCTATATGTCTATCCTAACTCATGGACACAGAGAGTAGAAGGATG
       GTTACCAAAGGCTGGGAAGGATAGAGGGGAGCTGGGGGAGGAGGTAGGGAAGGTTAATGG
       GTACAAAAAAAATAGAAAGAATGAATAACACCTACTATTTGATAGCATAGCAGGGTGGCT
       [C,A]
       TAGTCAATAATAACTGTACACTTTTAAATAAAGAGTGTAATAGGATTGTTTGCAACTCAA
       TGGATAAATGCTTGAGGGGATGGGTACCCCATTCTTCATGATGTGCCTATTTCACATTGC
       ATGCCTGTATCAAAAACATCTCATTTACTCCATAAATATATACACCTACTATGTATCCAC
       AAGTATTAAAAATTATAAATAAATAAATTATATAGCTATCCTTATGCTAGTACCACACTG
       CCTTACTGTTGCTTTGTAGTAAGCTTGAAATCAGGAAGTATGAGTCCCCCGCACTTTGG

5075   TTTGTAGTAAGCTTTGAAATCAGGAAGTATGAGTCCCCCGCACTTTGGTATTTTCCAAGA
       TTATTTTGGCTGTTTGGAATCCTTGATTTCTATACAAATTTTAGACTCAGCCTATCAATT
       TCTACAAGGAAACCAGCTAGGGTTCTGCTTGGGATTGCACTGAATCTGTAGATCAGTTTG
       GGGATTATTGCCATCTTAAGAATATTAGGTCTTCTGATCCATGAACACAGAAAGCCTTTC
       CGTTTAGTTAGGTCATCTTTAATTTTTTTGTTGTTTTTTTTGTTTTTGAGACAGAGT
       [T,G,C]
       CTGCTCTGTCGCCCAGGCTGGAGTGCAGTGACGCAATCTCGGCTCACTGCAACCTCCGCC
       TCTCGGATTCAAGCGATTCTCCTGCCTCAGCCTCCCAAGCAGCTGGGACTACAGGCACAT
       GCCACCACACCCAACTAATTTTTGTATTTTCAGTAGAGACGGGGTTTCACCATATTGGCCA
       GGCTAGTCTCGAACTCCTGACCTCGTGATCCACCCGCCTCACCCTCCCAAAGTGCTGGGA
       TTACAGGCGTGAGCCACCACTCCCGGCTTTCTTTAATTTTTTTAACGATGTTTTTGTAT

5450   GATTCTCCTGCCTCAGCCTCCCAAGCAGCTGGGACTACAGGCACATGCCACCACACCAAC
       TAATTTTTGTATTTTCAGTAGAGACGGGGTTTCACCATATTGGCCAGGCTAGTCTCGAAC
       TCCTGACCTCGTGATCCACCCGCCTCACCCTCCCAAAGTGCTGGGATTACAGGCGTGAGC
       CACCACTCCCGGCTTTCTTTAATTTTTTTAACGATGTTTTTGTATTTTTCAAAGTATAC
       ATCTTGCATTTCTTTTGTTAAATTTATTTGTTTTGTTCTTTTTAATTTCATTTCAGACTA
       [T,C]
```

FIGURE 3N

```
        TTATTGCATTCATAGTGTTTTAGAGTCCACATTCCCTCTTGACTGTCACTAAGTTTTTTT
        TTTTCTGTTTTTGAGAGGTTTCTATCAGAATTTTGCAGATCAGAGATGACGGACATGTCA
        AACTGTCTAATATTACCAACCCTCCCCATTTATCAGATCAGGATCCTTTTGGTGATTCAC
        CATGCAGGGAAATCTAGTATCTAAGGCTCAAAAGGTGATACTGTTTTACATAGGCAGTAA
        CATTTTATTGCTACATAATAACTACATATTTATGGAGTACCTGTGATATTTTGATACGTG

5450    GATTCTCCTGCCTCAGCCTCCCAAGCAGCTGGGACTACAGGCACATGCCACCACACCAAC
        TAATTTTTGTATTTTCAGTAGAGACGGGGTTTCACCATATTGGCCAGGCTAGTCTCGAAC
        TCCTGACCTCGTGATCCACCCGCCTCACCCTCCCAAAGTGCTGGGATTACAGGCGTGAGC
        CACCACTCCCGGCTTTCTTTAATTTTTTTAACGATGTTTTTGTATTTTTCAAAGTATAC
        ATCTTGCATTTCTTTTGTTAAATTTATTTGTTTTGTTCTTTTTAATTTCATTTCAGACTA
        [T,C]
        TTATTGCATTCATAGTGTTTTAGAGTCCACATTCCCTCTTGACTGTCACTAAGTTTTTTT
        TTTTCTGTTTTTGAGAGGTTTCTATCAGAATTTTGCAGATCAGAGATGACGGACATGTCA
        AACTGTCTAATATTACCAACCCTCCCCATTTATCAGATCAGGATCCTTTTGGTGATTCAC
        CATGCAGGGAAATCTAGTATCTAAGGCTCAAAAGGTGATACTGTTTTACATAGGCAGTAA
        CATTTTATTGCTACATAATAACTACATATTTATGGAGTACCTGTGATATTTTGATACGTG

5995    TTATTGCTACATAATAACTACATATTTATGGAGTACCTGTGATATTTTGATACGTGCATA
        CAATGTGCAGTGATCAAATCAGGGTGTTTAGGGTATTCATCACTTCTAACATTTATTATT
        TATTTGTGTTTGGAACATTTCAAGTCTCTTCAAGCTCTTCAGAAATATTCAATACATTAT
        TGTTAACAGTGCTATTGAACACTGGAACTTATTCCTTCTATCTAAAGACAGTAACATTTT
        AAGTATAGTCATAAGGTTACAGAAGGATAAAGTGTGTATAGGGAAAATTCCCTACAAGAT
        [G,A]
        AGAATTTCATTCCTTACTCTTAGTAATACAGGTCTTCAAACATGCCAAGGATATTCCTCC
        CTTGGAGCTTTGAACATGCACGTCTGTGGTTATATTGCTCTCCCTGCAAATTATTCCTAA
        AAGAGGCTTGCCCTGACCATTCAGACTAAAATAGCACCTCTAGTACTCTCTATCTCCAAC
        CCTATTATTATTATCTTGGCCCTTATCACTCTCTGACACTATACTGTATACTCTTTTGCT
        TGTTCGTTTATTATCCACCACTAACTACAATATAAAATCTGTGAGAGGTAGGATCTTTGT

6241    AGTCATAAGGTTACAGAAGGATAAAGTGTGTATAGGGAAAATTCCCTACAAGATGAGAAT
        TTCATTCCTTACTCTTAGTAATACAGGTCTTCAAACATGCCAAGGATATTCCTCCCTTGG
        AGCTTTGAACATGCACGTCTGTGGTTATATTGCTCTCCCTGCAAATTATTCCTAAAAGAG
        GCTTGCCCTGACCATTCAGACTAAAATAGCACCTCTAGTACTCTCTATCTCCAACCCTAT
        TATTATTATCTTGGCCCTTATCACTCTCTGACACTATACTGTATACTCTTTTGCTTGTTC
        [G,A]
        TTTATTATCCACCACTAACTACAATATAAAATCTGTGAGAGGTAGGATCTTTGTTTGCCA
        CTATAAACCTAGTGCATGGTACAGTTCCTGGTGCATAATAGGTGCTCAATAAATCCTTTG
        TTGAATGCATAAATATATTAGGTGCTGAGAAAATTTATTTATTCAAAGATCAATTTACTG
        CATAGAATAGGCCAGGTGGTTTGACATTTATTCAATAGCCAACATATGGGACCTAGGATG
        TACATATGCAAGTGTGTGTGTATGTGTGTGCATCTGCATGTGTACTTGGATGTACT

8479    AAAGCATGTTATGTCACTTCCAGAAAAGTCTCAGGCTCCTCTGCTTGTGTGACCTTATCA
        GGTCCTGAACTCAGCTTGTGTCTATAAGAGGGGACAGGTCCAGCTTGGCTGGCTAATTAC
        TTTTACTTTTTTCACTGCAGTTTATTCAGGATGATAACATGGAGAAGCTTGAGGAAATTA
        TTGAAAAATACCCTCGTGCCTTCCCTTTCTGGATTGGGCCCTTTCAGGCATTTTCTGTA
        TCTATGACCCAGACTATGCAAAGACACTTCTGAGCAGAACAGGTAAGAAGAGGGGGAAAG
        [C,T]
        TCTGGGACCTATTCCTCCTAGAAGTGAAATGCATAAAACCCATAGGCAAGATTCCAAAGC
        AAAGATTGGTTTGGGGCCTTTAAGAGACACAGCAGCAAGTATGGGAGGTGACAGGTTTC
        CTACCAATACTGAAGGGGATTCCCATATCCTCCCCAGTCCCTTGTCTTGTTCAGGTATGC
        ATGGGCACGTTGAAGTCGGTATAACTTAAAGCCTAGCTGGCATTACCAGACTTGCCAGGC
        AAGGCTTCCCTTGGCCTCTGTGGGTTTTATGACTTCAGTGTCAGCAACACTTCCCACTCC

10045   TCTGCTTGACTCTGCAGATCCCAAGTCCCAGTACCTGCAGAAATTCTCACCTCCACTTCT
        TGGTATGTATGTGCAAATGAGAGGTATAACCCACTCTCATTCAAAGTCCCCTTTCCATAG
        TAGAGCATGCCAAAGAAACTGAAATCTGAATTCAAAAGCACAAAGAGTGCAAGGTAGAGC
        TATACTGAACGTTATCTAGGGGAAAGATTGAAGGGGAGCTCTAAGGTCAACACACCACCA
```

FIGURE 30

```
        CTTCCCAGAAAGCTTCTTCATCCGTTTCTCTCCCACAAAGTCTTATTCTCAAGGCAGCAG
        [C,A]
        TACATGAATCTGTCCCCTCTCTCTTTAAAACTACAGCCTTGGCCAGGCACAGTGACTCAT
        GCATGTAATCCCAGCACTTTGGGAGGCCAAGGTGGGAGGATCACTTGAGGTCAAGATTTC
        AAGACCAGCTGGGCCAACATGGTGAAATCCCATCTCTACTAAAAATACAAAAATTAGCCA
        GGCATGGTAGCATGTAGGCCTGTAGTCCCACTACTTGGGAGGCTGAGACATGAGAATCGC
        TTGAACCTAGGAGGTGG

10045   TCTGCTTGACTCTGCAGATCCCAAGTCCCAGTACCTGCAGAAATTCTCACCTCCACTTCT
        TGGTATGTATGTGCAAATGAGAGGTATAACCCACTCTCATTCAAAGTCCCCTTTCCATAG
        TAGAGCATGCCAAAGAAACTGAAATCTGAATTCAAAAGCACAAAGAGTGCAAGGTAGAGC
        TATACTGAACGTTATCTAGGGGAAAGATTGAAGGGGAGCTCTAAGGTCAACACACCACCA
        CTTCCCAGAAAGCTTCTTCATCCGTTTCTCTCCCACAAAGTCTTATTCTCAAGGCAGCAG
        [G,A]
        TACATGAATCTGTCCCCTCTCTCTTTAAAACTACAGCCTTGGCCAGGCACAGTGACTCAT
        GCATGTAATCCCAGCACTTTGGGAGGCCAAGGTGGGAGGATCACTTGAGGTCAAGATTTC
        AAGACCAGCTGGGCCAACATGGTGAAATCCCATCTCTACTAAAAATACAAAAATTAGCCA
        GGCATGGTAGCATGTAGGCCTGT

11994   GGTAAGTAAAGGGGGAAAGTGCTCTGTGCATTGCGAAATGCTCCCAGCAATGGACAGTAT
        TAGGTATGTGTTTTGTGGGCCATGAAAATAAAAAATCAGTTTCTAAAAATTTAACCAATG
        TACACGTACTTATTGAACAATAGGTGTCTGTAAAAAATTTGTTATGTTCTTTGAGTGATA
        ATATTAATAAAAAGATCTGGTCCTCTGTCTTAGATATATTTTGAGATTTTATGGCAGCAA
        ACCAAGTACCAAATGGTGATAGTTAGATAGTAAGTGCTGTAGATGTGTTTCATGGAGGGC
        [G,A]
        GGTCTGTACAAACCTACCCCAAAGTCTGAGGAAACTGAGAGGCTGAAGAAAAAGGCTGAC
        AGTTTCTTAAAAAGAAACATTCAATAGAGGCTTTCAAACAAAAACCAT

14070   GGTCAGGCTTTGCTGGGGGCAGCTCCCTGCAACAGCTCCTCTCCACACTTGCTCTGTTTC
        TCACTTTTGAATCCAAACGTTTTTTGAAAATGTTCTGAGTTTATTTTAAAATGTGGCTATG
        GTGGTTGAGAGCAGTGGCAGGGTACCTAGCAAGTTTGGAATTGAAGTTGGAGGAAGCCCT
        GGGGTAAACCCCTTGTAATTATGGGTCTTGTGTCAATGATTGCTTTAATGGAACTCTGGT
        CTGTTTGAAAGCAGAGTTATGGTAATAATTGAAAAGCCGCAGATCTTTAACTCAGCCATT
        [A,G,T]
        ACCATATATGCAGTTTTCTCCATGCTCCTTCTCACTCCGCTGGGTGTATTTTTCCCTTCC
        TCGTGCCCTGTGTAAGCACATGGCTTATTTACTCATGTGATCTTTGGTTCCTGCTGGGTC
        AGGGTTGTCTCCATTAGATCATAAAAACAGGGCCAGGCAGGAGCCTTCAAATGAAGGCAA
        TTTGGTCATGGTGGTGGTGATGATGTTGGTCTTGACCTCCTGTGCCAGGATAAGTGGGAG
        AAGATTTGCAGCACTCAGGACACAAGCGTGGAGGTCTATGAGCACATCAACTCGATGTCT

15535   ACTTACTGCTTTGTTTCAGTGTCATCTATAAAATGGAGATTAAAAAAGAACCTATCTCAT
        ACATTTGTTGTTACGATGAGTGGGTTAATATATATAAAGCATTTAGGACAGTGCCTGGCA
        CTGAATAGATGTTAAATGTAAAGTATAGTTATGTCAAATGTCTTTGCTTCCAGGAATTTT
        GCAAGACACACCAACATATGCACACTTACACATACATATATGCATACATGCACATAGATA
        TTATAAAGAGGACACTCAGAGAAGCAGGTTATAAACAATTTAAGGCATAAATGGGCATTA
        [T,C]
        AAATAGCAGCAGTTCCCAAGTCTTTCTGCATCATTGCACACACAGAAAATGTTAATGTTT
        TTGTGCTTCATTGGAGTAAACAGGAATGGATTTGGGGGAAGCTATACAGAACTTTGTAAA
        AAAAAATCTTTACTTTTTAAATATTATACAATTATGATGAAAAAGCAAAATGCAAAGTGT
        TAGGGAAAATATTAAATGTTAAATTTATTCAAAACTTAAAACCTTTTCAATTTTTTTTTT
        TTTTTTTTTTTGAGATGGAGTCTCTATCACTCAGGCTGGAGCGCAGTGGTGTGATCTCAG

17618   GGTAAGTGGGAATGGGATGGGGAGACAAGAATAAAACCGATTGACTAAATTTAACTGTAC
        TTTGAATTGATGAGCAGCTTCATGCAATTTGAGACAAAGAGAGAATTCTGCAACTGTGTC
        GCTAGAGGAGGGTTAGTAAAGACTAAACGAACGATTTGACAAGATTTGAGGATTGTCATA
        TGGATACATGGATTTTAGGGCATCATGAAAAAATGGTCACATGGATAAACGTAAAAATTA
        TGATGATAAGGTCCTGGGAAATCTGGGAGTTTGAAGAGAATTTCTAGGGCCTGTTGATCG
        [C,T,A]
```

FIGURE 3P

```
            GGGCCCTTTGTGCAAGGCCTGCTTTTCTTATCTAACCTTGGTTCTCCTTTATGCTTTGGG
            CAGAATATGGTTTATACCACATATTTGTTGAACTGAATTAAAATTTAAACCCCTATTTAA
            AGCTCTGATTTTTCCCCTCAAATCATTATTGTGGTTGTATCTCCAAACATTTATAAACTG
            GCATTTTATTTAAAATATTTGTATTGTACTTTCTAGGATGAAAGTGGTAGCAGCTTCTCA
            GATATTGATGTACACTCTGAAGTGAGCACATTCCTGTTGGCAGGACATGACACCTTGGCA

18520       ATTTATCCATAAATTGTCTGTCATTGGTTTTCTAATCAATGGTGTGTGAAATGTCTTATT
            TCTTTATTTCACCTTGGCTCTGATGCATTGGAAATGAGGACTTGATCCCTGGGCTGGCAC
            TTAGAACTTAAACAATAGGGTCCAAGTGGAGCTCCTCTTCTGAGAGAGCTGAATGATTAG
            CTGCATTATTTAAGGCTCATTTTAGACATCTCCCAGCCGCTTGTCACCAATTTTATTCCT
            CAGGATTGATTTTAGACTTCAGACATAATATTCGATGATATATACTATAGTTAAGTTTAG
            [A,-,C]
            AAATATGGACTGAGGACATTTTAAATACTGAGACTTTTTTTATGACTACAATTTATTGTG
            GGCCCTGTCTTCGGTGAGCTAATGGTCTAATACAGGAGACAGGAGACAGACCTCCAAATT
            GCAGTGTAGCATAATGAGGGCAATGATAGAGATATGTGCTGGCTAACACAAAGACATAGA
            AGACAGGTACCTACCCTGGCATGGGAGCTCAAGGAGACTTCCTTGACATTTACGCTGACT
            GCAGGATAAGTAGGAGTTAGCCAGGTGGAAACTGTCATCTCTATCTTGCTAGACTTTAAG

18525       TCCATAAATTGTCTGTCATTGGTTTTCTAATCAATGGTGTGTGAAATGTCTTATTTCTTT
            ATTTCACCTTGGCTCTGATGCATTGGAAATGAGGACTTGATCCCTGGGCTGGCACTTAGA
            ACTTAAACAATAGGGTCCAAGTGGAGCTCCTCTTCTGAGAGAGCTGAATGATTAGCTGCA
            TTATTTAAGGCTCATTTTAGACATCTCCCAGCCGCTTGTCACCAATTTTATTCCTCAGGA
            TTGATTTTAGACTTCAGACATAATATTCGATGATATATACTATAGTTAAGTTTAGCAAAT
            [-,T,A]
            TGGACTGAGGACATTTTAAATACTGAGACTTTTTTTATGACTACAATTTATTGTGGGCCC
            TGTCTTCGGTGAGCTAATGGTCTAATACAGGAGACAGGAGACAGACCTCCAAATTGCAGT
            GTAGCATAATGAGGGCAATGATAGAGATATGTGCTGGCTAACACAAAGACATAGAAGACA
            GGTACCTACCCTGGCATGGGAGCTCAAGGAGACTTCCTTGACATTTACGCTGACTGCAGG
            ATAAGTAGGAGTTAGCCAGGTGGAAACTGTCATCTCTATCTTGCTAGACTTTAAGCATAT

18525       TCCATAAATTGTCTGTCATTGGTTTTCTAATCAATGGTGTGTGAAATGTCTTATTTCTTT
            ATTTCACCTTGGCTCTGATGCATTGGAAATGAGGACTTGATCCCTGGGCTGGCACTTAGA
            ACTTAAACAATAGGGTCCAAGTGGAGCTCCTCTTCTGAGAGAGCTGAATGATTAGCTGCA
            TTATTTAAGGCTCATTTTAGACATCTCCCAGCCGCTTGTCACCAATTTTATTCCTCAGGA
            TTGATTTTAGACTTCAGACATAATATTCGATGATATATACTATAGTTAAGTTTAGCAAAT
            [-,G,A]
            TGGACTGAGGACATTTTAAATACTGAGACTTTTTTTATGACTACAATTTATTGTGGGCCC
            TGTCTTCGGTGAGCTAATGGTCTAATACAGGAGACAGGAGACAGACCTCCAAATTGCAGT
            GTAGCATAATGAGGGCAATGATAGAGATATGTGCTGGCTAACACAAAGACATAGAAGACA
            GGTACCTACCCTGGCATGGGAGCTCAAGGAGACTTCCTTGACATTTACGCTGACTGCAGG
            ATAAGTAGGAGTTAGCCAGGTGGAAACTGTCATCTCTATCTTGCTAGACTTTAAGCATAT

19189       CTGGTCAAAGGGACAGAAAGACAGAAATGCTAAGGACAATTCAGCAGCAGACCAGATAAA
            AAACACCATATTTCATATGCAAAAGTCAACTCAATTGAAACATTTGTAAAACCAAATTTG
            ACATTATAAAAGTATATCAGAGATCTCATTTTATAAGGAAATAGAAGCCCTTTCCTACCA
            TAAACTAAAGATTTAATCTATATAGCACAAAATACAATGTTGAGTAATCATTTTTAATTT
            ATTTTTTAACTGACAAAAATTGTGCATATACATGTTATATATATATGTATGTGTGTATAT
            [T,C,A]
            TATATGATGTACAACATGATATTTTGATATATGTATACACTGTGGAATGACTAAATCTAT
            CAATGGACATGTTCATTAACTCATACTTATCATTTTTTTGTGGTAAGGACATTTAAAATC
            TACCCTCTTAGCAATTTTCAAGTATACAAATTGTTAGTAACTCCAATCACATATTGTACA
            ATGCATCTCCTAAACTTATGCCTCCTGTCTGACTGAAATTTTGTATCCTTTGACTAACAT
            CCCTGTAATCCCCCATTCTCCCACAGCCCCTGGTAACCACTGTTCTACTCTCTGCTTCTT

19259       TTTCATATGCAAAAGTCAACTCAATTGAAACATTTGTAAAACCAAATTTGACATTATAAA
            AGTATATCAGAGATCTCATTTTATAAGGAAATAGAAGCCCTTTCCTACCATAAACTAAAG
            ATTTAATCTATATAGCACAAAATACAATGTTGAGTAATCATTTTTAATTTATTTTTTAAC
            TGACAAAAATTGTGCATATACATGTTATATATATATGTATGTGTGTATATATATATGATG
```

FIGURE 3Q

```
         TACAACATGATATTTTGATATATGTATACACTGTGGAATGACTAAATCTATCAATGGACA
         [C,T]
         GTTCATTAACTCATACTTATCATTTTTTTGTGGTAAGGACATTTAAAATCTACCCTCTTA
         GCAATTTTCAAGTATACAAATTGTTAGTAACTCCAATCACATATTGTACAATGCATCTCC
         TAAACTTATGCCTCCTGTCTGACTGAAATTTTGTATCCTTTGACTAACATCCCTGTAATC
         CCCCATTCTCCCACAGCCCCTGGTAACCACTGTTCTACTCTCTGCTTCTTTGAGTTTAAT
         GTTTTAGATTTCCACATGTGAGATCATGTGGAATTTGTCTTTCTGTGCCTGGCTTATTTC

19325    TCAGAGATCTCATTTTATAAGGAAATAGAAGCCCTTTCCTACCATAAACTAAAGATTTAA
         TCTATATAGCACAAAATACAATGTTGAGTAATCATTTTTAATTTATTTTTTAACTGACAA
         AAATTGTGCATATACATGTTATATATATATGTATGTGTGTATATATATATGATGTACAAC
         ATGATATTTTGATATATGTATACACTGTGGAATGACTAAATCTATCAATGGACATGTTCA
         TTAACTCATACTTATCATTTTTTTGTGGTAAGGACATTTAAAATCTACCCTCTTAGCAAT
         [G,T]
         TTCAAGTATACAAATTGTTAGTAACTCCAATCACATATTGTACAATGCATCTCCTAAACT
         TATGCCTCCTGTCTGACTGAAATTTTGTATCCTTTGACTAACATCCCTGTAATCCCCCAT
         TCTCCCACAGCCCCTGGTAACCACTGTTCTACTCTCTGCTTCTTTGAGTTTAATGTTTTA
         GATTTCCACATGTGAGATCATGTGGAATTTGTCTTTCTGTGCCTGGCTTATTTCACTTAG
         CATAATGTCATCCAAATTCATCTCTGTTGTCATAAATGACAAGATATTTGTCTTTTCTAT

19346    GAAATAGAAGCCCTTTCCTACCATAAACTAAAGATTTAATCTATATAGCACAAAATACAA
         TGTTGAGTAATCATTTTTAATTTATTTTTTAACTGACAAAAATTGTGCATATACATGTTA
         TATATATATGTATGTGTGTATATATATATGATGTACAACATGATATTTTGATATATGTAT
         ACACTGTGGAATGACTAAATCTATCAATGGACATGTTCATTAACTCATACTTATCATTTT
         TTTGTGGTAAGGACATTTAAAATCTACCCTCTTAGCAATTTTCAAGTATACAAATTGTTA
         [G,T]
         TAACTCCAATCACATATTGTACAATGCATCTCCTAAACTTATGCCTCCTGTCTGACTGAA
         ATTTTGTATCCTTTGACTAACATCCCTGTAATCCCCCATTCTCCCACAGCCCCTGGTAAC
         CACTGTTCTACTCTCTGCTTCTTTGAGTTTAATGTTTTAGATTTCCACATGTGAGATCAT
         GTGGAATTTGTCTTTCTGTGCCTGGCTTATTTCACTTAGCATAATGTCATCCAAATTCAT
         CTCTGTTGTCATAAATGACAAGATATTTGTCTTTTCTATGGCTAATTGTTAGTCCATTGT

20845    TGTTACTGGAACCTTTGTAGATCAGTTGACAATAAATGTGTGGGTGTATTTCTGGACTCT
         TTATCCTGTTTTATTAGTTTATATGTCTCTTTTTTTAGAAGCTCTATGCTGTTTTGGTGA
         CTAGAGCTCTGTAGTCAATTTCAGATCAGGTAGTATGATGCACTCCAGCTTTGCTCTTTT
         TGCTCAAAATTGCTTTGGCTATTTGAGTTTTTTTATTCCATACGAATTTTAGGGCTTTTT
         TTTTTTTTCGATTACTGTGAATAATGCCATTGGAATTTTGATGGAGATTGCATTGAATCT
         [-,T]
         TGGGTAGTATGGATATTTTAACAGTATTAATGCTTCCAATTAATGAACACAGGGTATTTT
         GCAATTTGTGTTTTCTTCAATTTCTTTCACCAGTGTTTTTTTCTTAATTTAATTGTTTTA
         TTTCCATAGGGTTTGGGTAACAGGTGGTGTTTGGTTATGAGTAAGTTCTTTAGTGGTGAT
         TTGTGAGATTTTGATGCACCCATCACCTAAGCAGTATACACTGTACCCAATTTGTAGTCT
         TGTATCCCTCACCTCCCTCCCACCATTTCCCCCAAGTCCCCAAAGTCCATTGTATCATTC

20845    TGTTACTGGAACCTTTGTAGATCAGTTGACAATAAATGTGTGGGTGTATTTCTGGACTCT
         TTATCCTGTTTTATTAGTTTATATGTCTCTTTTTTTAGAAGCTCTATGCTGTTTTGGTGA
         CTAGAGCTCTGTAGTCAATTTCAGATCAGGTAGTATGATGCACTCCAGCTTTGCTCTTTT
         TGCTCAAAATTGCTTTGGCTATTTGAGTTTTTTTATTCCATACGAATTTTAGGGCTTTTT
         TTTTTTTTCGATTACTGTGAATAATGCCATTGGAATTTTGATGGAGATTGCATTGAATCT
         [T,C]
         TGGGTAGTATGGATATTTTAACAGTATTAATGCTTCCAATTAATGAACACAGGGTATTTT
         GCAATTTGTGTTTTCTTCAATTTCTTTCACCAGTGTTTTTTTCTTAATTTAATTGTTTTA
         TTTCCATAGGGTTTGGGTAACAGGTGGTGTTTGGTTATGAGTAAGTTCTTTAGTGGTGAT
         TTGTGAGATTTTGATGCACCCATCACCTAAGCAGTATACACTGTACCCAATTTGTAGTCT
         TGTATCCCTCACCTCCCTCCCACCATTTCCCCCAAGTCCCCAAAGTCCATTGTATCATTC

22234    AGAAACTTTTTAGTTTAATTAAGTCCCACCTATTTATCTTTTCGTTGTTGTTGTTTTTTG
         GGGTTGTTTTGTTTTGGCTTGGTTTTGCATCTGCTTTTGGGTTCTTGGTCATGAAGTCTT
```

FIGURE 3R

```
           TGCCTAAGCCAATATCTAGAAGGGTTTTTCTGATGTTCTAGAATTTTTATGGTTCAGGTC
           TTAGATTTAAGTCCTTGATCCATCTTGAGTTGATTTTTGTATAAGGTGAGAGATGAGGAT
           CCAGTTTCATGCTTCTACATGTGGCTTGCCAATTATCCCAGTACAATTTGTTGAATAGGG
           [T,C]
           TAATATTTAAAGCTTTATATATTTAGGTGTTCCTATTTTGGGTACATATTTATTTACAAC
           TATCATATCCTCCTGATGGATTGACCCCTTTCTCATTATATAATGGTCTTCTTGTCTCTT
           TTTACAGTTTTTGTCTTAAAGCCTAATTTGTCTGATAAAAGTTCAGCTACCTTTGCTCTC
           TTTTGGTTTCTATTTGCATGGAATATTTTTTTCCAACCCTTCGCATTCACTCTATGTGTG
           TTCTTAAAGATGAAATGAGATGCTGTAGGGGCATATGCTTGGGTCTTGTTTTATTCATTC

22234      AGAAACTTTTTAGTTTAATTAAGTCCCACCTATTTATCTTTTCGTTGTTGTTGTTTTTTG
           GGGTTGTTTTGTTTTGGCTTGGTTTTGCATCTGCTTTTGGGTTCTTGGTCATGAAGTCTT
           TGCCTAAGCCAATATCTAGAAGGGTTTTTCTGATGTTCTAGAATTTTTATGGTTCAGGTC
           TTAGATTTAAGTCCTTGATCCATCTTGAGTTGATTTTTGTATAAGGTGAGAGATGAGGAT
           CCAGTTTCATGCTTCTACATGTGGCTTGCCAATTATCCCAGTACAATTTGTTGAATAGGG
           [G,T]
           TAATATTTAAAGCTTTATATATTTAGGTGTTCCTATTTTGGGTACATATTTATTTACAAC
           TATCATATCCTCCTGATGGATTGACCCCTTTCTCATTATATAATGGTCTTCTTGTCTCTT
           TTTACAGTTTTTGTCTTAAAGCCTAATTTGTCTGATAAAAGTTCAGCTACCTTTGCTCTC
           TTTTGGTTTCTATTTGCATGGAATATTTTTTTCCAACCCTTCGCATTCACTCTATGTGTG
           TTCTTAAAGATGAAATGAGATGCTGTAGGGGCATATGCTTGGGTCTTGTTTTATTCATTC

22247      TTTAATTAAGTCCCACCTATTTATCTTTTCGTTGTTGTTGTTTTTGGGGTTGTTTTGTT
           TTGGCTTGGTTTTGCATCTGCTTTTGGGTTCTTGGTCATGAAGTCTTTGCCTAAGCCAAT
           ATCTAGAAGGGTTTTTCTGATGTTCTAGAATTTTTATGGTTCAGGTCTTAGATTTAAGTC
           CTTGATCCATCTTGAGTTGATTTTTGTATAAGGTGAGAGATGAGGATCCAGTTTCATGCT
           TCTACATGTGGCTTGCCAATTATCCCAGTACAATTTGTTGAATAGGGTTAATATTTAAAG
           [C,T]
           TTTATATATTTAGGTGTTCCTATTTTGGGTACATATTTATTTACAACTATCATATCCTCC
           TGATGGATTGACCCCTTTCTCATTATATAATGGTCTTCTTGTCTCTTTTTACAGTTTTTG
           TCTTAAAGCCTAATTTGTCTGATAAAAGTTCAGCTACCTTTGCTCTCTTTTGGTTTCTAT
           TTGCATGGAATATTTTTTTCCAACCCTTCGCATTCACTCTATGTGTGTTCTTAAAGATGA
           AATGAGATGCTGTAGGGGCATATGCTTGGGTCTTGTTTTATTCATTCATTCAGCCACCCT

22334      GTTCTTGGTCATGAAGTCTTTGCCTAAGCCAATATCTAGAAGGGTTTTTCTGATGTTCTA
           GAATTTTTATGGTTCAGGTCTTAGATTTAAGTCCTTGATCCATCTTGAGTTGATTTTTGT
           ATAAGGTGAGAGATGAGGATCCAGTTTCATGCTTCTACATGTGGCTTGCCAATTATCCCA
           GTACAATTTGTTGAATAGGGTTAATATTTAAAGCTTTATATATTTAGGTGTTCCTATTTT
           GGGTACATATTTATTTACAACTATCATATCCTCCTGATGGATTGACCCCTTTCTCATTAT
           [A,G]
           TAATGGTCTTCTTGTCTCTTTTTACAGTTTTTGTCTTAAAGCCTAATTTGTCTGATAAAA
           GTTCAGCTACCTTTGCTCTCTTTTGGTTTCTATTTGCATGGAATATTTTTTTCCAACCCT
           TCGCATTCACTCTATGTGTGTTCTTAAAGATGAAATGAGATGCTGTAGGGGCATATGCTT
           GGGTCTTGTTTTATTCATTCAGCCACCCTTTTGATTAGAGAATTTAATTCATTTGT
           ATTCAAGGTAATTATTGACAGACAAGGACTTACTACTGCCATTTTGTTAATTGTTTTCTT

23033      ATCTTTTGTTGCTCTACTATAGGTTTTTGCTTTGTGGTTACCATGAGGGTTACATAAAGC
           ATAGTTATAAAAGGCTATTTTAAACTGATAACAGCTTAACTTTCAACACTTAAAAAAACT
           ATACACTTTTACTCTACCAACTGCCCTCCATTTTATGTCTTTGATGTCATAATTTACCTA
           GTTTTGGAGATGTGTCCCCTTATTGTGTATCCCTTAACAAATTATTGTAGCAACAGTCAT
           TTTTAATAGTTTTGGCTTTTAACTTTATACTAGAGATAGAATTAATTAACATACCACCAC
           [T,-]
           ACATTATTAGGGTATTCTAAATTGACTATGTATTTACCTTTATCAGTGAGATTTTTGTTT
           TCAATTTTCATGTTGTTAATTAGTATTCTTTCATTTCAACTTGGAGAATTCACATTAGCA
           TTTTTTGTAAGATGGGTCTAGTAGTGGTGAACACCCTCAACTTTTGTTTATCTGGAGATG
           TCTTTACCTCTGCTTCATTTTGAAATATAACTTTTGTTCCATGATTGAAATGGACAAAAT
           TGTTTTTTTAATTATGCAAAGTGCCAGGGTAAGCAGAATTACTCTTTTTTTTTTTTTCTG
```

FIGURE 3S

23036   TTTTGTTGCTCTACTATAGGTTTTTGCTTTGTGGTTACCATGAGGGTTACATAAAGCATA
        GTTATAAAAGGCTATTTTAAACTGATAACAGCTTAACTTTCAACACTTAAAAAAAACTATA
        CACTTTTACTCTACCAACTGCCCTCCATTTTATGTCTTTGATGTCATAATTTACCTAGTT
        TTGGAGATGTGTCCCCTTATTGTGTATCCCTTAACAAATTATTGTAGCAACAGTCATTTT
        TAATAGTTTTGGCTTTTAACTTTATACTAGAGATAGAATTAATTAACATACCACCACTAC
        [-,A]
        TTATTAGGGTATTCTAAATTGACTATGTATTTACCTTTATCAGTGAGATTTTTGTTTTCA
        ATTTTCATGTTGTTAATTAGTATTCTTTCATTTCAACTTGGAGAATTCACATTAGCATTT
        TTTGTAAGATGGGTCTAGTAGTGGTGAACACCCTCAACTTTTGTTTATCTGGAGATGTCT
        TTACCTCTGCTTCATTTTGAAATATAACTTTTGTTCCATGATTGAAATGGACAAAATTGT
        TTTTTTAATTATGCAAAGTGCCAGGGTAAGCAGAATTACTCTTTTTTTTTTTTTCTGAGA

23421   CTTTCATTTCAACTTGGAGAATTCACATTAGCATTTTTTGTAAGATGGGTCTAGTAGTGG
        TGAACACCCTCAACTTTTGTTTATCTGGAGATGTCTTTACCTCTGCTTCATTTTGAAATA
        TAACTTTTGTTCCATGATTGAAATGGACAAAATTGTTTTTTTAATTATGCAAAGTGCCAG
        GGTAAGCAGAATTACTCTTTTTTTTTTTTCTGAGACCGAGTTTCACTCTTGTTGCCCAG
        GCTGGAGTGCAGTGGCGCAATCTCTCAGCTTACCGCAACCTCTGCCTCCCAGGTTCAAGC
        [A,G]
        ATTCTTCTGCCTCAGCCTTCCTGAGTAGCTGGGATTACAGGCATGCACCACCATGCTCGG
        CTAATTTTGCATTTTTAGTAGAGACGGGGTTTCTCCATGTTGGTCAGGCTGGTCTTGAAC
        ACCCGACCTCAGATGATCCGCCCACCTAGGCCTCCCAAAGTGCTGGGATTGCAGGTGTGA
        GCCACTGCGCCTGGCCAGAATTACTCTTATTTATCCTGAGCTTGAGGAAGAAAGAATTCA
        AAATTAAAATTTCACATTACCTAATGGCCAAAGCCTGCATTCAAAATAAGTAATCAGAAA

25582   CCCAAAGGCACATAGCCAGTTGCAGCAAAGCTAAGCCCAGAATCCATGTCTCTGGAATCC
        CAGCCCAGGGTCTCTTCCATTGTGGGACATCATTTCTAAGATAATCTTTGTTTGGCTGAG
        TTTGAGACCGAGCTGAAACTTCATGGAAAATAGCACCAGCATCTTTATCTGAAAGACCAA
        GGGGGATCTTTGGCCTCATCATCATAATATCACCCTTATAAATATACAACATTTAATAGT
        TAATATAGAGCCTTCAGACCCATTATCTCATTTTTCCCCTTGGAATCCAATGTTAACAGA
        [T,C]
        GCTTATACAATGATTTACAGTTCACTGAACACTTTTAAGTACTTTCAATGTGGCCCAAAA
        TCCAGAGGCAGCCCCAATGTGTAGATGACATTAACTGATGTGAGCAGAGCTAGAACTTGT
        GCGGAGACCCTGAGTCTGGAGCCTAGAGTTCTTCGGAACAACACAGGTTTCTGAGCAGGG
        CTTATAGGAAGCAGAGGGGTCATGTGAGACATATTATCTGATTCAATGTTCTATTAATTC
        ATGTCTTAGGAAGCAAGCCAACAGGATTGCTTCTGGCAAACACCTACAGCCTGTTACTGT

26407   CCTCTCAAGACAGAGTCTTGCTATGTAGCCCAGGCTGGAGTACAGTGGCGTAATCTCGGC
        TCACTGCAACCTCTGCCTCCCAGGTTTAAGCAGTTCTCCTGCCTCAGCCTCCCGAGTAGC
        TGGGATTACAGGTGCACACCACGCCTGGCAAATTTTGTATTTTTATTAGAGATGGGGTT
        TCACCATGTTGGCCAGGCTAGTCTCAAGCTCCTGATCTCGAGACCAGCCCTCCTCAGCCT
        CCCAAAGCGCTGGGACTACAGCCATGAGCCACTGCACCCAGCCAGTTCTGTGCTTTTATA
        [C,A]
        CTAAATTGTCTCCAGGAGTGCTTAATAGTCCATTAATAGGTATTTAGGCCAGGCACAGTG
        GCTGACGCATATAATCCCAATATTTTGTGACACCAAGGTGGGAAGACTGCTTGAAGTTAG
        GAGTCTGAGACTAGCCTGGGCAACATAGGGAGACCCTGTCTTTACAAAAAAAAAAAAGAG
        AGAGATAGCCAGGCATGGTGTTGCATGCTTGTATTCCTGCCTACTTGGGGACTGAGGCA
        GGAGGATCACTTGAGCTCAGAAGTTCAAGGTTACCGTGAGCAATGTTCACGCCACTGCTC

26473   CAACCTCTGCCTCCCAGGTTTAAGCAGTTCTCCTGCCTCAGCCTCCCGAGTAGCTGGGAT
        TACAGGTGCACACCACGCCTGGCAAATTTTGTATTTTTATTAGAGATGGGGTTTCACCA
        TGTTGGCCAGGCTAGTCTCAAGCTCCTGATCTCGAGACCAGCCCTCCTCAGCCTCCCAAA
        GCGCTGGGACTACAGCCATGAGCCACTGCACCCAGCCAGTTCTGTGCTTTTATACCTAAA
        TTGTCTCCAGGAGTGCTTAATAGTCCATTAATAGGTATTTAGGCCAGGCACAGTGGCTGA
        [C,T]
        GCATATAATCCCAATATTTTGTGACACCAAGGTGGGAAGACTGCTTGAAGTTAGGAGTCT
        GAGACTAGCCTGGGCAACATAGGGAGACCCTGTCTTTACAAAAAAAAAAAAGAGAGAGAT
        AGCCAGGCATGGTGTTGCATGCTTGTATTCCTGCCTACTTGGGGACTGAGGCAGGAGGA
        TCACTTGAGCTCAGAAGTTCAAGGTTACCGTGAGCAATGTTCACGCCACTGCTCTCCAGC

FIGURE 3T

```
       CTGATTGACAGGCCAGACCCTGACTCTAAACAAAAACAAAAAACAAATATTTAAGTAATT
26844  TGGGCAACATAGGGAGACCCTGTCTTTACAAAAAAAAAAAAGAGAGAGATAGCCAGGCAT
       GGTGTTGCATGCTTGTATTCCTGCCTACTTGGGGGACTGAGGCAGGAGGATCACTTGAGC
       TCAGAAGTTCAAGGTTACCGTGAGCAATGTTCACGCCACTGCTCTCCAGCCTGATTGACA
       GGCCAGACCCTGACTCTAAACAAAAACAAAAAACAAATATTTAAGTAATTTCCAAACATA
       GCAGAAAATATAAGCATGGTTTATCACTTTGATATGACACCAACAGCTACTTAAGATAGA
       [G,A]
       TCATGAATTCAGTAAATTGTTGTGTGGAAAGCTAAGGTGCCAACCCAAGCCGCATCTTCT
       TAGGTGCTCCTCACTGGTGTCATCAGCTACAGCAGGCAGAGCATTGCCAGGAGCTAGCTC
       TTCCCTTCAAGAACAAAAGTCTTGTTTAAGAGCACAGTAGCCCACAACTTGCTCTTTCTC
       CTGCAGTCTCTTTTATTTCCCTCCTTTCTTAGGGATCACCGTGGTTCTTAGTATTTGGGG
       TCTTCACCACAACCCTGCTGTCTGGAAAAACCCAAAGGTATGATTCTCTCTTGTACATAA

28384  CTTCCAGGGAACCGTAGATCTTGGTGCCTATTTGAGCCCCAAAGGATCAGTTAGTTTTAC
       AAAGGACAATCGTATTCTCTGTCACATCCTTTTTGGCCATGCCTCAAAAGCAGTCCCACA
       ATGTAAGCTACTGCTCATAGGCTCAATGCAGTCCACCTTCAAAGCAAGAGAAATAATTTC
       ATGAGTAACTCCAACTGCCGCCTTGTTATAGGGAAGGCATCATGTTGGAGCCTCCCAGCT
       CAAATTCTCACAGTGAACAATTTAAGTCTAAAGTTCAAAAGTTTCAATGGCATTTGGTGG
       [A,-]
       AAAAATATCACTTTACTGTGTACTTCAGACTTCTTGTACTAGTATTTTACTATAGTCAGA
       AGAAACATCATTTTTTCAAGTATCACTTTCTTTCCCTCTTGTCTTCAGGAACTGCATTGG
       GCAGGAGTTTGCCATGATTGAGTTAAAGGTAACCATTGCCTTGATTCTGCTCCACTTCAG
       AGTGACTCCAGACCCCACCAGGCCTCTTACTTTCCCCAACCATTTTATCCTCAAGCCCAA
       GAATGGGATGTATTTGCACCTGAAGAAACTCTCTGAATGTTAGATCTCAGGGTACAATGA

28417  GAGCCCCAAAGGATCAGTTAGTTTTACAAAGGACAATCGTATTCTCTGTCACATCCTTTT
       TGGCCATGCCTCAAAAGCAGTCCCACAATGTAAGCTACTGCTCATAGGCTCAATGCAGTC
       CACCTTCAAAGCAAGAGAAATAATTTCATGAGTAACTCCAACTGCCGCCTTGTTATAGGG
       AAGGCATCATGTTGGAGCCTCCCAGCTCAAATTCTCACAGTGAACAATTTAAGTCTAAAG
       TTCAAAAGTTTCAATGGCATTTGGTGGAAAAAATATCACTTTACTGTGTACTTCAGACTT
       [A,C]
       TTGTACTAGTATTTTACTATAGTCAGAAGAAACATCATTTTTTCAAGTATCACTTTCTTT
       CCCTCTTGTCTTCAGGAACTGCATTGGGCAGGAGTTTGCCATGATTGAGTTAAAGGTAAC
       CATTGCCTTGATTCTGCTCCACTTCAGAGTGACTCCAGACCCCACCAGGCCTCTTACTTT
       CCCCAACCATTTTATCCTCAAGCCCAAGAATGGGATGTATTTGCACCTGAAGAAACTCTC
       TGAATGTTAGATCTCAGGGTACAATGATTAAACGTACTTTGTTTTTCGAAGTTAAATTTA

29265  TATGCAAGTAATAAGTGCATGTATGCTCACTGTCAAAAATTCCCAACACTAGAAAATCAT
       GTAGAATAAAAATTTTAAATCTCACTTCACTTAGCCGACATTCCATGCCCTGACCAATCC
       TACTGCTTTTCCTAAAAACAGAATAATTTGGTGTGCATTCTTTCAGACTTTTTCCTATAC
       ATTTTATATGTAGAAATGTAGCAATGTATTTGTATAGATGTGATCATTCCTATATTGTTA
       TTGATTTTTTTCACTTAATAAAAATTCACCTTATTCCTTATCATTGCTTTATGGTATTCT
       [A,G]
       TAATATGAATGTACTATAATTTATTTAACTATTTTCCTTATTGGGCATTTAAGTTATTTC
       TAGTTTTAAAAACATGCTTGTCAATGGCAACAAAAGCCAAAATTGACAAATGGGATCTAA
       TTAAACTAAAGAGCTTCTGCACAGCAAAACAAACTACCATCACACTGAATGGGCAGCCTA
       CAGAATGGGAGAAAATTTTTGCAACCTACTCATCTGACAAAGGCCTAATATCCAGAATCT
       ACAATGAACTCAAACAAATGTACAAGAAAAAAACAACCCCATCAAAAGTGGGTGAAGGA

29484  GTGATCATTCCTATATTGTTATTGATTTTTTTCACTTAATAAAAATTCACCTTATTCCTT
       ATCATTGCTTTATGGTATTCTGTAATATGAATGTACTATAATTTATTTAACTATTTTCCT
       TATTGGGCATTTAAGTTATTTCTAGTTTTAAAAACATGCTTGTCAATGGCAACAAAAGCC
       AAAATTGACAAATGGGATCTAATTAAACTAAAGAGCTTCTGCACAGCAAAACAAACTACC
       ATCACACTGAATGGGCAGCCTACAGAATGGGAGAAAATTTTTGCAACCTACTCATCTGAC
       [A,G]
       AAGGCCTAATATCCAGAATCTACAATGAACTCAAACAAATGTACAAGAAAAAAACAACCC
       CATCAAAAGTGGGTGAAGGATATGAACAGACACTTCTCAAAAGAAGACATTTACGCAGC
```

FIGURE 3U

```
        CAAAAGACACATGAAAAAATGCCTATCGTCACTGGCCATCAGAGAAATGCAAATCAAAAC
        CACAATGAGATACCATCTCACACCAGTTAGAATGGCAATCATTAAAAAGTCAGGAAACAA
        CAGGTGCTGGAGAGGATGTGGAGAAATAGGAAGACTTTTACACTGTTGGTGGCAGGAGAA

30417   ATTCATCTACCTAAAATCTATATATAAAAAAATCCCTCCCTTGAATTCCAGATCCTTGGA
        GACAAACACCCACGTCTAAAACCAAATTTGTTTAACACTGGACCAGTCGTCCTGTGTGAC
        TTTCCATTTTGTCACTATTTTGTCAGCTGGTATACCAATATCCACCCAGTTAAACAATAT
        TTCCTTGTTTTTTTCTGGTACAAACCCAAATAAATTACAAACATCAATAAAAGTAAAATT
        CTAAAATAACTCACTTTCTCTATATATCTCCTTCTTGCTGGAAAAATGGGTTAGGTTAGT
        [T,-]
        CTTTAAAAGCATGCATGATAAATTGTACTGAATACAATATTCAGGTCTGGACATACTAGG
        TATAATTTTCTGTGTCTCTGGGGTCTTACCTATTTGGGGTCAAAATAAACAAGTTTATTA
        AGCTTATTAATATTCAATTTCATTATCTTCTTTAACAATTATGTTCCCTGGTAGTTTCAT
        TGCCAATAATTTATTTGTCAGGTTGCCAGGTGCTTCTAAACTTCTGTGTATTTTTTCATA
        TCCAATTTTACTTTAAATATTTTTAGAAAAGAGGTCTGTTAAATTTCCTAATAATTATTA

30783   TTTTCTGTGTCTCTGGGGTCTTACCTATTTGGGGTCAAAATAAACAAGTTTATTAAGCTT
        ATTAATATTCAATTTCATTATCTTCTTTAACAATTATGTTCCCTGGTAGTTTCATTGCCA
        ATAATTTATTTGTCAGGTTGCCAGGTGCTTCTAAACTTCTGTGTATTTTTTCATATCCAA
        TTTTACTTTAAATATTTTTAGAAAAGAGGTCTGTTAAATTTCCTAATAATTATTATATTA
        TTGTTTTTTCACTGACATTTTGTGAATTGAAAACCCTTAAAAATATGAAATCATTTTTTC
        [C,G]
        AAATATGTGCCACAGACAATTTTGTTAAATAAGAAGACAGAAACAGGGCATTATCAAGAG
        ATAAATATTCAATATACCTTATATTTCTGTCACACATTTTTATACCAACTGTGCCAAAAA
        TTGTATATCATATAAATGATAACAAGTTCACAAAGGCATTCCTTTATCCCTTAACTCTCA
        AATTAGAAACTTTCATAGGTAGGAAGTAGGGGAAGCATATATTCCCTTTGAAAGGTGCAA
        GAAAATGTCATTGGCATTCACCATGGTACTCTTCAAGCTTAAAAAAAATGGACTGCAAAA
```

FIGURE 3V

ISOLATED HUMAN DRUG-METABOLIZING PROTEINS, NUCLEIC ACID MOLECULES ENCODING HUMAN DRUG-METABOLIZING PROTEINS, AND USES THEREOF

The present application is a divisional of U.S. application Ser. No. 09/852,067, filed on May 10, 2001 and issued on Mar. 11, 2003 as U.S. Pat. No. 6,531,297, which is a CIP of U.S. application Ser. No. 09/818,647 filed on Mar. 28, 2001 (abandoned), which claims priority to U.S. Provisional Application No. 60/241,745 filed on Oct. 20, 2000.

FIELD OF THE INVENTION

The present invention is in the field of drug-metabolizing proteins that are related to the omega-hydroxylase cytochrome P450 drug-metabolizing enzyme subfamily, recombinant DNA molecules and protein production. The present invention specifically provides novel drug-metabolizing peptides and proteins and nucleic acid molecules encoding such protein molecules, for use in the development of human therapeutics and human therapeutic development.

BACKGROUND OF THE INVENTION

Drug-Metabolizing Proteins

Induction of drug-metabolizing enzymes ("DMEs") is a common biological response to xenobiotics, the mechanisms and consequences of which are important in academic, industrial, and regulatory areas of pharmacology and toxicology.

For most drugs, drug-metabolizing enzymes determine how long and how much of a drug remains in the body. Thus, developers of drugs recognize the importance of characterizing a drug candidate's interaction with these enzymes. For example, polymorphisms of the drug-metabolizing enzyme CYP2D6, a member of the cytochrome p450 ("CYP") superfamily, yield phenotypes of slow or ultra-rapid metabolizers of a wide spectrum of drugs including antidepressants, antipsychotics, beta-blockers, and antiarrhythmics. Such abnormal rates of drug metabolism can lead to drug ineffectiveness or to systemic accumulation and toxicity.

For pharmaceutical scientists developing a candidate drug, it is important know as early as possible in the design phase which enzymes metabolize the drug candidate and the speed with which they do it. Historically, the enzymes on a drug's metabolic pathway were determined through metabolism studies in animals, but this approach has now been largely supplanted by the use of human tissues or cloned drug-metabolizing enzymes to provide insights into the specific role of individual forms of these enzymes. Using these tools, the qualitative and quantitative fate of a drug candidate can be predicted prior to its first administration to humans. As a consequence, the selection and optimization of desirable characteristics of metabolism are possible early in the development process, thus avoiding unanticipated toxicity problems and associated costs subsequent to the drug's clinical investigation. Moreover, the effect of one drug on another's disposition can be inferred.

Known drug-metabolizing enzymes include the cytochrome p450 ("CYP") superfamily, N-acetyl transferases ("NAT"), UDP-glucuronosyl transferases ("UGT"), methyl transferases, alcohol dehydrogenase ("ADH"), aldehyde dehydrogenase ("ALDH"), dihydropyrimidine dehydrogenase ("DPD"), NADPH:quinone oxidoreductase ("NQO" or "DT diaphorase"), catechol O-methyltransferase ("COMT"), glutathione S-transferase ("GST"), histamine methyltransferase ("HMT"), sulfotransferases ("ST"), thiopurine methyltransferase ("TPMT"), and epoxide hydroxylase. Drug-metabolizing enzymes are generally classified into two phases according to their metabolic function. Phase I enzymes catalyze modification of functional groups, and phase II enzymes catalyze conjugation with endogenous substituents. These classifications should not be construed as exclusive nor exhaustive, as other mechanisms of drug metabolism have been discovered. For example, the use of active transport mechanisms been characterized as part of the process of detoxification.

Phase I reactions include catabolic processes such as deamination of aminases, hydrolysis of esters and amides, conjugation reactions with, for example, glycine or sulfate, oxidation by the cytochrome p450 oxidation/reduction enzyme system and degradation in the fatty acid pathway. Hydrolysis reactions occur mainly in the liver and plasma by a variety of non-specific hydrolases and esterases. Both deaminases and amidases, also localized in the liver and serum, carry out a large part of the catabolic process. Reduction reactions occur mainly intracellularly in the endoplasmic reticulum.

Phase II enzymes detoxify toxic substances by catalyzing their conjugation with water-soluble substances, thus increasing toxins' solubility in water and increasing their rate of excretion. Additionally, conjugation reduces the toxins' biological reactivity. Examples of phase II enzymes include glutathione S-transferases and UDP-glucuronosyl transferases, which catalyze conjugation to glutathione and glucuronic acid, respectively. Transferases perform conjugation reactions mainly in the kidneys and liver.

The liver is the primary site of elimination of most drugs, including psychoactive drugs, and contains a plurality of both phase I and phase II enzymes that oxidize or conjugate drugs, respectively.

Physicians currently prescribe drugs and their dosages based on a population average and fail to take genetic variability into account. The variability between individuals in drug metabolism is usually due to both genetic and environmental factors, in particular, how the drug-metabolizing enzymes are controlled. With certain enzymes, the genetic component predominates and variability is associated with variants of the normal, wild-type enzyme.

Most drug-metabolizing enzymes exhibit clinically relevant genetic polymorphisms. Essentially all of the major human enzymes responsible for modification of functional groups or conjugation with endogenous subsituents exhibit common polymorphisms at the genomic level. For example, polymorphisms expressing a non-functioning variant enzyme results in a sub-group of patients in the population who are more prone to the concentration-dependent effects of a drug. This sub-group of patients may show toxic side effects to a dose of drug that is otherwise without side effects in the general population. Recent development in genotyping allows identification of affected individuals. As a result, their a typical metabolism and likely response to a drug metabolized by the affected enzyme can be understood and predicted, thus permitting the physician to adjust the dose of drug they receive to achieve improved therapy.

A similar approach is also becoming important in identifying risk factors associated with the development of various cancers. This is because the enzymes involved in drug metabolism are also responsible for the activation and detoxification of chemical carcinogens. Specifically, the development of neoplasia is regulated by a balance between phase I enzymes, which activate carcinogens, and phase II enzymes, which detoxify them. Accordingly, an individual's susceptibility to cancer often involves the balance between these two processes, which is, in part, genetically determined and can be screened by suitable genotyping tests. Higher induction of phase I enzymes compared to phase II enzymes results in the generation of large amounts of electrophiles and reactive oxygen species and may cause DNA and membrane damage and other adverse effects leading to neoplasia. Conversely, higher levels of phase II enzyme expression can protect cells from various chemical compounds.

Abnormal activity of drug-metabolizing enzymes has been implicated in a range of human diseases, including cancer, Parkinson's disease, myetonic dystrophy, and developmental defects.

Cytochrome p450

An example of a phase I drug-metabolizing enzyme is the cytochrome p450 ("CYP") superfamily, the members of which comprise the major drug-metabolizing enzymes expressed in the liver. The CYP superfamily comprises heme proteins which catalyze the oxidation and dehydrogenation of a number of endogenous and exogenous lipophilic compounds. The CYP superfamily has immense diversity in its functions, with hundreds of isoforms in many species catalyzing many types of chemical reactions. The CYP superfamily comprises at least 30 related enzymes, which are divided into different families according to their amino acid homology. Examples of CYP families include CYP families 1, 2, 3 and 4, which comprise endoplasmic reticulum proteins responsible for the metabolism of drugs and other xenobiotics. Approximately 10–15 individual gene products within these four families metabolize thousands of structurally diverse compounds. It is estimated that collectively the enzymes in the CYP superfamily participate in the metabolism of greater than 80% of all available drugs used in humans. For example, the CYP 1A subfamily comprises CYP 1A2, which metabolizes several widely used drugs, including acetaminophen, amitriptyline, caffeine, clozapine, haloperidol, imipramine, olanzapine, ondansetron, phenacetin, propafenone, propranolol, tacrine, theophylline, verapamil. In addition, CYP enzymes play additional roles in the metabolism of some endogenous substrates including prostaglandins and steroids.

Some CYP enzymes exist in a polymorphic form, meaning that a small percentage of the population possesses mutant genes that alter the activity of the enzyme, usually by diminishing or abolishing activity. For example, a genetic polymorphism has been well characterized with the CYP 2C19 and CYP 2D6 genes. Substrates of CYP 2C19 include clomipramine, diazepam, imipramine, mephenytoin, moclobemide, omeprazole, phenytoin, propranolol, and tolbutamide. Substrates of CYP 2D6 include alprenolol, amitriptyline, chlorpheniramine, clomipramine, codeine, desipramine, dextromethorphan, encainide, fluoxetine, haloperidol, imipramine, indoramin, metoprolol, nortriptyline, ondansetron, oxycodone, paroxetine, propranolol, and propafenone. Polymorphic variants of these genes metabolize these substrates at different rates, which can effect a patient's effective therapeutic dosage.

While the substrate specificity of CYPs must be very broad to accommodate the metabolism of all of these compounds, each individual CYP gene product has a narrower substrate specificity defined by its binding and catalytic sites. Drug metabolism can thereby be regulated by changes in the amount or activity of specific CYP gene products. Methods of CYP regulation include genetic differences in the expression of CYP gene products (i.e., genetic polymorphisms), inhibition of CYP metabolism by other xenobiotics that also bind to the CYP, and induction of certain CYPs by the drug itself or other xenobiotics. Inhibition and induction of CYPs is one of the most common mechanisms of adverse drug interactions. For example, the CYP3A subfamily is involved in clinically significant drug interactions involving nonsedating antihistamines and cisapride that may result in cardiac dysrhythmias. In another example, CYP3A4 and CYP1A2 enzymes are involved in drug interactions involving theophylline. In yet another example, CYP2D6 is responsible for the metabolism of many psychotherapeutic agents. Additionallly, CYP enzymes metabolize the protease inhibitors used to treat patients infected with the human immunodeficiency virus. By understanding the unique functions and characteristics of these enzymes, physicians may better anticipate and manage drug interactions and may predict or explain an individual's response to a particular therapeutic regimen.

Examples of reactions catalyzed by the CYP superfamily include peroxidative reactions utilizing peroxides as oxygen donors in hydroxylation reactions, as substrates for reductive beta-scission, and as peroxyhemiacetal intermediates in the cleavage of aldehydes to formate and alkenes. Lipid hydroperoxides undergo reductive beta-cleavage to give hydrocarbons and aldehydic acids. One of these products, trans-4-hydroxynonenal, inactivates CYP, particularly alcohol-inducible 2E1, in what may be a negative regulatory process. Although a CYP iron-oxene species is believed to be the oxygen donor in most hydroxylation reactions, an iron-peroxy species is apparently involved in the deformylation of many aldehydes with desaturation of the remaining structure, as in aromatization reactions.

Examples of drugs with oxidative metabolism associated with CYP enzymes include acetaminophen, alfentanil, alprazolam, alprenolol, amiodarone, amitriptyline, astemizole, buspirone caffeine, carbamazepine, chlorpheniramine, cisapride, clomipramine, clomipramine, clozapine, codeine, colchicine, cortisol, cyclophosphamide, cyclosporine, dapsone, desipramine, dextromethorphan, diazepam, diclofenac, diltiazem, encainide, erythromycin, estradiol, felodipine, fluoxetine, fluvastatin, haloperidol, ibuprofen, imipramine, indinavir, indomethacin, indoramin, irbesartan, lidocaine, losartan, macrolide antibiotics, mephenytoin, methadone, metoprolol, mexilitene, midazolam, moclobemide, naproxen, nefazodone, nicardipine, nifedipine, nitrendipine, nortriptyline, olanzapine, omeprazole, ondansetron, oxycodone, paclitaxel, paroxetine, phenacetin, phenytoin, piroxicam, progesterone, propafenone, propranolol, quinidine, ritonavir, saquinavir, sertraline, sildenafil, S-warfarin, tacrine, tamoxifen, tenoxicam, terfenadine, testosterone, theophylline, timolol, tolbutamide, triazolam, verapamil, and vinblastine.

Abnormal activity of phase I enzymes has been implicated in a range of human diseases. For example, enhanced CYP2D6 activity has been related to malignancies of the bladder, liver, pharynx, stomach and lungs, whereas decreased CYP2D activity has been linked to an increased risk of Parkinson's disease. Other syndromes and developmental defects associated with deficiencies in the CYP superfamily include cerebrotendinous xanthomatosis, adrenal hyperplasia, gynecomastia, and myetonic dystrophy.

Omega-Hydroxylase Cytochrome P450

The novel human protein, and encoding gene, provided by the present invention is related to the omega-hydroxylase cytochrome P450 family, which includes, for example, cytochrome P450 4A4 (CYP4A4), cytochrome P-450p-2, prostaglandin omega-hydroxylase, and laurate omega-hydroxylase. Omega-Hydroxylase Cytochrome P450 proteins catalyze omega- (including omega-1) hydroxylation of prostaglandin A and fatty acids such as caprate, laurate, myristate, and palmitate (Yoshimura et al., *J Biochem* (Tokyo) 1990 October;108(4):544–8). CYP4A4 is elevated during pregnancy (Palmer et al., *Arch Biochem Biophys* 1993 Feb 1;300(2):670–6).

Matsubara et al., *J Biol Chem* 1987 Sep 25;262(27): 13366–71; Yamamoto et al., (1984) *J. Biochem.* (Tokyo) 96, 593–603; Yokotani et al., *Eur J Biochem* 1991 Mar 28;196 (3):531–6; and Johnson et al., *Biochemistry* 1990 Jan 30;29 (4):873–9.

Cytochromes, such as the protein provided by the present invention, have many utilities, in addition to those described above. Cytochromes not only metabolize normal physiological substrates but also neutralize environmental toxins. In addition to oxidizing steroids, fatty acids, and foreign compounds in liver cells, cytochromes can also be induced by toxic chemicals, pesticides, and cancerogens.

Immunological and PCR-based assays for cytochromes may be used to determine toxicity and turnover rate of experimental medicines. Selective cytotoxic drugs can be designed that interact with a particular cytochrome and trigger cell death, thereby providing potential new treatments for cancer.

Cytochromes can generate free radicals that cause myocardial cell injury and induce endothelial cell damage. In experimental models, alpha-tocopherol and other anti-oxidants suppress generation of free radicals. Glutathione and glutathione peroxidase contribute to natural protection against free radical-induced cell damage. Characterization of all cytochromes will assist development of more efficient anti-oxidants. The sequence provided by the present invention can be used to design specific chemopreventive drugs.

The cytochrome provided herein, as well as other human cytochromes, can be used in a high-throughput drug screen to discover anti-parasitic drugs that inhibit non-human oxigenases but exhibit no toxicity for the human enzymes.

For a further review of the CYP superfamily, see Igarashi et al., *Arch Biochem Biophys* 1997 Mar 1;339(1):85–91; *Med Lett Drugs Ther* 2000 Apr 17;42(1076):35–6 (no authors listed); Fowler et al., *Biochemistry* 2000 Apr 18;39 (15):4406–14; Lamb et al., *Chem Biol Interact* 2000 Mar 15;125(3):165–75; Chiba et al., *Xenobiotica* 2000 Febuary; 30(2):117–29; and Meehan et al., *Am J Hum Genet* 1988 January ;42(1):26–37.

The CYP superfamily a major target for drug action and development. Accordingly, it is valuable to the field of pharmaceutical development to identify and characterize previously unknown members of the CYP superfamily.

UDP-glucuronosyltransferases

Potential drug interactions involving phase II metabolism are increasingly being recognized. An important group of phase II enzymes involved in drug metabolism are the glucuronosyltransferases, especially the UDP-glucuronyltransferase ("UGT") superfamily. Members of the UGT superfamily catalyze the enzymatic addition of UDP glucuronic acid as a sugar donor to fat-soluble chemicals, a process which increases their solubility in water and increases their rate of excretion. In mammals, glucuronic acid is the main sugar that is used to prevent the accumulation of waste products of metabolism and fat-soluble chemicals from the environment to toxic levels in the body. Both inducers and inhibitors of glucuronosyltransferases are known and have the potential to affect the plasma concentration and actions of important drugs, including psychotropic drugs.

The UGT superfamily comprises several families of enzymes in several species defined with a nomenclature similar to that used to define members of the CYP superfamily. In animals, yeast, plants and bacteria there are at least 110 distinct known members of the UGT superfamily. As many as 33 families have been defined, with three families identified in humans. Different UGT families are defined as having <45% amino acid sequence homology; within subfamilies there is approximately 60% homology. The members of the UGT superfamily are part of a further superfamily of UDP glycosyltransferases found in animals, plants and bacteria.

The role of phase II enzymes, and of UGT enzymes in particular, is being increasingly recognized as important in psychopharmacology. UGT enzymes conjugate many important psychotropic drugs and are an important source of variability in drug response and drug interactions. For example, the benzodiazepines lorazepam, oxazepam, and temazepam undergo phase II reactions exclusively before being excreted into the urine.

Phase II enzymes metabolize and detoxify hazardous substances, such as carcinogens. The expression of genes encoding phase II enzymes is known to be up-regulated by hundreds of agents. For example, oltipraz is known to up-regulate phase II enzyme expression. Studies have demonstrated protection from the cancer-causing effects of carcinogens when selected phase II enzyme inducers are administered prior to the carcinogens. The potential use of phase II enzyme inducers in humans for prevention of cancers related to exposure to carcinogens has prompted studies aimed at understanding their molecular effects. Current biochemical and molecular biological research methodologies can be used to identify and characterize selective phase II enzyme inducers and their targets. Identification of genes responding to cancer chemopreventive agents will facilitate studies of their basic mechanism and provide insights about the relationship between gene regulation, enzyme polymorphism, and carcinogen detoxification.

Examples of drugs with conjugative metabolism associated with UGT enzymes include amitriptyline, buprenorphine, chlorpromazine, clozapine, codeine, cyproheptadine, dihydrocodeine, doxepin, imipramine, lamotrigine, lorazepam, morphine, nalorphine, naltrexone, temazepam, and valproate.

Abnormal activity of phase II enzymes has been implicated in a range of human diseases. For example, Gilbert syndrome is an autosomal dominant disorder caused by mutation in the UGT1 gene, and mutations in the UGT1A1 enzyme have been demonstrated to be responsible for Crigler-Najjar syndrome.

The UGT superfamily a major target for drug action and development. Accordingly, it is valuable to the field of pharmaceutical development to identify and characterize previously unknown members of the UGT superfamily.

Drug-metabolizing enzymes, particularly members of the omega-hydroxylase cytochrome P450 drug-metabolizing enzyme subfamily, are a major target for drug action and development. Accordingly, it is valuable to the field of pharmaceutical development to identify and characterize previously unknown members of this subfamily of drug-metabolizing proteins. The present invention advances the state of the art by providing a previously unidentified human drug-metabolizing proteins that have homology to members of the omega-hydroxylase cytochrome P450 drug-metabolizing enzyme subfamily.

SUMMARY OF THE INVENTION

The present invention is based in part on the identification of amino acid sequences of human drug-metabolizing enzyme peptides and proteins that are related to the omega-hydroxylase cytochrome P450 drug-metabolizing enzyme subfamily, as well as allelic variants and other mammalian orthologs thereof. These unique peptide sequences, and nucleic acid sequences that encode these peptides, can be used as models for the development of human therapeutic targets, aid in the identification of therapeutic proteins, and serve as targets for the development of human therapeutic agents that modulate drug-metabolizing enzyme activity in cells and tissues that express the drug-metabolizing enzyme. Experimental data as provided in FIG. 1 indicates expression in humans in the stomach, brain (including infant), endometrial tumors, prostate, kidney, adrenal gland tumors, head/neck, sympathetic trunk, breast, and hepatocellular carcinomas.

DESCRIPTION OF THE FIGURE SHEETS

FIG. 1A–1B provides the nucleotide sequence of a cDNA molecule that encodes the drug-metabolizing enzyme protein of the present invention. (SEQ ID NO:1) In addition, structure and functional information is provided, such as ATG start, stop and tissue distribution, where available, that allows one to readily determine specific uses of inventions based on this molecular sequence. Experimental data as provided in FIG. 1 indicates expression in humans in the stomach, brain (including infant), endometrial tumors, prostate, kidney, adrenal gland tumors, head/neck, sympathetic trunk, breast, and hepatocellular carcinomas.

FIG. 2A–2D provides the predicted amino acid sequence of the drug-metabolizing enzyme of the present invention. (SEQ ID NO:2) In addition structure and functional information such as protein family, function, and modification sites is provided where available, allowing one to readily determine specific uses of inventions based on this molecular sequence.

FIG. 3A–3V provides genomic sequences that span the gene encoding the drug-metabolizing enzyme protein of the present invention. (SEQ ID NO:3) In addition structure and functional information, such as intron/exon structure, promoter location, etc., is provided where available, allowing one to readily determine specific uses of inventions based on this molecular sequence. As illustrated in FIG. 3, SNPs were identified at 45 different nucleotide positions.

DETAILED DESCRIPTION OF THE INVENTION

General Description

The present invention is based on the sequencing of the human genome. During the sequencing and assembly of the human genome, analysis of the sequence information revealed previously unidentified fragments of the human genome that encode peptides that share structural and/or sequence homology to protein/peptide/domains identified and characterized within the art as being a drug-metabolizing enzyme protein or part of a drug-metabolizing enzyme protein and are related to the omega-hydroxylase cytochrome P450 drug-metabolizing enzyme subfamily. Utilizing these sequences, additional genomic sequences were assembled and transcript and/or cDNA sequences were isolated and characterized. Based on this analysis, the present invention provides amino acid sequences of human drug-metabolizing enzyme peptides and proteins that are related to the omega-hydroxylase cytochrome P450 drug-metabolizing enzyme subfamily, nucleic acid sequences in the form of transcript sequences, cDNA sequences and/or genomic sequences that encode these drug-metabolizing enzyme peptides and proteins, nucleic acid variation (allelic information), tissue distribution of expression, and information about the closest art known protein/peptide/domain that has structural or sequence homology to the drug-metabolizing enzyme of the present invention.

In addition to being previously unknown, the peptides that are provided in the present invention are selected based on their ability to be used for the development of commercially important products and services. Specifically, the present peptides are selected based on homology and/or structural relatedness to known drug-metabolizing enzyme proteins of the omega-hydroxylase cytochrome P450 drug-metabolizing enzyme subfamily and the expression pattern observed. Experimental data as provided in FIG. 1 indicates expression in humans in the stomach, brain (including infant), endometrial tumors, prostate, kidney, adrenal gland tumors, head/neck, sympathetic trunk, breast, and hepatocellular carcinomas. The art has clearly established the commercial importance of members of this family of proteins and proteins that have expression patterns similar to that of the present gene. Some of the more specific features of the peptides of the present invention, and the uses thereof, are described herein, particularly in the Background of the Invention and in the annotation provided in the Figures, and/or are known within the art for each of the known omega-hydroxylase cytochrome P450 family or subfamily of drug-metabolizing enzyme proteins.

Specific Embodiments

Peptide Molecules

The present invention provides nucleic acid sequences that encode protein molecules that have been identified as being members of the drug-metabolizing enzyme family of proteins and are related to the omega-hydroxylase cytochrome P450 drug-metabolizing enzyme subfamily (protein sequences are provided in FIG. 2, transcript/cDNA sequences are provided in FIG. 1 and genomic sequences are provided in FIG. 3). The peptide sequences provided in FIG. 2, as well as the obvious variants described herein, particularly allelic variants as identified herein and using the information in FIG. 3, will be referred herein as the drug-metabolizing enzyme peptides of the present invention, drug-metabolizing enzyme peptides, or peptides/proteins of the present invention.

The present invention provides isolated peptide and protein molecules that consist of, consist essentially of, or comprise the amino acid sequences of the drug-metabolizing enzyme peptides disclosed in the FIG. 2, (encoded by the nucleic acid molecule shown in FIG. 1, transcript/cDNA or FIG. 3, genomic sequence), as well as all obvious variants of these peptides that are within the art to make and use. Some of these variants are described in detail below.

As used herein, a peptide is said to be "isolated" or "purified" when it is substantially free of cellular material or free of chemical precursors or other chemicals. The peptides of the present invention can be purified to homogeneity or other degrees of purity. The level of purification will be based on the intended use. The critical feature is that the preparation allows for the desired function of the peptide, even if in the presence of considerable amounts of other components (the features of an isolated nucleic acid molecule is discussed below).

In some uses, "substantially free of cellular material" includes preparations of the peptide having less than about 30% (by dry weight) other proteins (i.e., contaminating protein), less than about 20% other proteins, less than about 10% other proteins, or less than about 5% other proteins. When the peptide is recombinantly produced, it can also be substantially free of culture medium, i.e., culture medium represents less than about 20% of the volume of the protein preparation.

The language "substantially free of chemical precursors or other chemicals" includes preparations of the peptide in which it is separated from chemical precursors or other chemicals that are involved in its synthesis. In one embodiment, the language "substantially free of chemical precursors or other chemicals" includes preparations of the drug-metabolizing enzyme peptide having less than about 30% (by dry weight) chemical precursors or other chemicals, less than about 20% chemical precursors or other chemicals, less than about 10% chemical precursors or other chemicals, or less than about 5% chemical precursors or other chemicals.

The isolated drug-metabolizing enzyme peptide can be purified from cells that naturally express it, purified from cells that have been altered to express it (recombinant), or synthesized using known protein synthesis methods. Experimental data as provided in FIG. 1 indicates expression in humans in the stomach, brain (including infant), endometrial tumors, prostate, kidney, adrenal gland tumors, head/neck, sympathetic trunk, breast, and hepatocellular carcinomas. For example, a nucleic acid molecule encoding the drug-metabolizing enzyme peptide is cloned into an expression vector, the expression vector introduced into a host cell and the protein expressed in the host cell. The protein can then be isolated from the cells by an appropriate purification scheme using standard protein purification techniques. Many of these techniques are described in detail below.

Accordingly, the present invention provides proteins that consist of the amino acid sequences provided in FIG. 2 (SEQ ID NO:2), for example, proteins encoded by the transcript/cDNA nucleic acid sequences shown in FIG. 1 (SEQ ID NO:1) and the genomic sequences provided in FIG. 3 (SEQ ID NO:3). The amino acid sequence of such a protein is provided in FIG. 2. A protein consists of an amino acid sequence when the amino acid sequence is the final amino acid sequence of the protein.

The present invention further provides proteins that consist essentially of the amino acid sequences provided in FIG. 2 (SEQ ID NO:2), for example, proteins encoded by the transcript/cDNA nucleic acid sequences shown in FIG. 1 (SEQ ID NO:1) and the genomic sequences provided in FIG. 3 (SEQ ID NO:3). A protein consists essentially of an amino acid sequence when such an amino acid sequence is present with only a few additional amino acid residues, for example from about 1 to about 100 or so additional residues, typically from 1 to about 20 additional residues in the final protein.

The present invention further provides proteins that comprise the amino acid sequences provided in FIG. 2 (SEQ ID NO:2), for example, proteins encoded by the transcript/cDNA nucleic acid sequences shown in FIG. 1 (SEQ ID NO:1) and the genomic sequences provided in FIG. 3 (SEQ ID NO:3). A protein comprises an amino acid sequence when the amino acid sequence is at least part of the final amino acid sequence of the protein. In such a fashion, the protein can be only the peptide or have additional amino acid molecules, such as amino acid residues (contiguous encoded sequence) that are naturally associated with it or heterologous amino acid residues/peptide sequences. Such a protein can have a few additional amino acid residues or can comprise several hundred or more additional amino acids. The preferred classes of proteins that are comprised of the drug-metabolizing enzyme peptides of the present invention are the naturally occurring mature proteins. A brief description of how various types of these proteins can be made/isolated is provided below.

The drug-metabolizing enzyme peptides of the present invention can be attached to heterologous sequences to form chimeric or fusion proteins. Such chimeric and fusion proteins comprise a drug-metabolizing enzyme peptide operatively linked to a heterologous protein having an amino acid sequence not substantially homologous to the drug-metabolizing enzyme peptide. "Operatively linked" indicates that the drug-metabolizing enzyme peptide and the heterologous protein are fused in-frame. The heterologous protein can be fused to the N-terminus or C-terminus of the drug-metabolizing enzyme peptide.

In some uses, the fusion protein does not affect the activity of the drug-metabolizing enzyme peptide per se. For example, the fusion protein can include, but is not limited to, enzymatic fusion proteins, for example beta-galactosidase fusions, yeast two-hybrid GAL fusions, poly-His fusions, MYC-tagged, HI-tagged and Ig fusions. Such fusion proteins, particularly poly-His fusions, can facilitate the purification of recombinant drug-metabolizing enzyme peptide. In certain host cells (e.g., mammalian host cells), expression and/or secretion of a protein can be increased by using a heterologous signal sequence.

A chimeric or fusion protein can be produced by standard recombinant DNA techniques. For example, DNA fragments coding for the different protein sequences are ligated together in-frame in accordance with conventional techniques. In another embodiment, the fusion gene can be synthesized by conventional techniques including automated DNA synthesizers. Alternatively, PCR amplification of gene fragments can be carried out using anchor primers which give rise to complementary overhangs between two consecutive gene fragments which can subsequently be annealed and re-amplified to generate a chimeric gene sequence (see Ausubel et al., *Current Protocols in Molecular Biology*, 1992). Moreover, many expression vectors are commercially available that already encode a fusion moiety (e.g., a GST protein). A drug-metabolizing enzyme peptide-encoding nucleic acid can be cloned into such an expression vector such that the fusion moiety is linked in-frame to the drug-metabolizing enzyme peptide.

As mentioned above, the present invention also provides and enables obvious variants of the amino acid sequence of the proteins of the present invention, such as naturally occurring mature forms of the peptide, allelic/sequence variants of the peptides, non-naturally occurring recombinantly derived variants of the peptides, and orthologs and paralogs of the peptides. Such variants can readily be generated using art-known techniques in the fields of recombinant nucleic acid technology and protein biochemistry. It is understood, however, that variants exclude any amino acid sequences disclosed prior to the invention.

Such variants can readily be identified/made using molecular techniques and the sequence information disclosed herein. Further, such variants can readily be distinguished from other peptides based on sequence and/or structural homology to the drug-metabolizing enzyme peptides of the present invention. The degree of homology/ identity present will be based primarily on whether the peptide is a functional variant or non-functional variant, the amount of divergence present in the paralog family and the evolutionary distance between the orthologs.

To determine the percent identity of two amino acid sequences or two nucleic acid sequences, the sequences are aligned for optimal comparison purposes (e.g., gaps can be introduced in one or both of a first and a second amino acid or nucleic acid sequence for optimal alignment and non-homologous sequences can be disregarded for comparison purposes). In a preferred embodiment, at least 30%, 40%, 50%, 60%, 70%, 80%, or 90% or more of the length of a reference sequence is aligned for comparison purposes. The amino acid residues or nucleotides at corresponding amino acid positions or nucleotide positions are then compared. When a position in the first sequence is occupied by the same amino acid residue or nucleotide as the corresponding position in the second sequence, then the molecules are identical at that position (as used herein amino acid or nucleic acid "identity" is equivalent to amino acid or nucleic acid "homology"). The percent identity between the two sequences is a function of the number of identical positions shared by the sequences, taking into account the number of gaps, and the length of each gap, which need to be introduced for optimal alignment of the two sequences.

The comparison of sequences and determination of percent identity and similarity between two sequences can be accomplished using a mathematical algorithm. (*Computational Molecular Biology,* Lesk, A. M., ed., Oxford University Press, New York, 1988; *Biocomputing: Informatics and Genome Projects,* Smith, D. W., ed., Academic Press, New York, 1993; *Computer Analysis of Sequence Data, Part* 1, Griffin, A. M., and Griffin, H. G., eds., Humana Press, New Jersey, 1994; *Sequence Analysis in Molecular Biology,* von Heinje, G., Academic Press, 1987; and *Sequence Analysis Primer,* Gribskov, M. and Devereux, J., eds., M Stockton Press, New York, 1991). In a preferred embodiment, the percent identity between two amino acid sequences is determined using the Needleman and Wunsch (*J. Mol. Biol.* (48):444–453. (1970)) algorithm which has been incorporated into the GAP program in the GCG software package (available at http://www.gcg.com), using either a Blossom 62 matrix or a PAM250 matrix, and a gap weight of 16, 14, 12, 10, 8, 6, or 4 and a length weight of 1, 2, 3, 4, 5, or 6. In yet another preferred embodiment, the percent identity between two nucleotide sequences is determined using the GAP program in the GCG software package (Devereux, J., et al., *Nucleic Acids Res.* 12(1):387 (1984)) (available at http://www.gcg.com), using a NWS-gapdna.CMP matrix and a gap weight of 40, 50, 60, 70, or 80 and a length weight of 1, 2, 3, 4, 5, or 6. In another embodiment, the percent identity between two amino acid or nucleotide sequences is determined using the algorithm of E. Myers and W. Miller (CABIOS, 4:11–17 (1989)) which has been incorporated into the ALIGN program (version 2.0), using a PAM120 weight residue table, a gap length penalty of 12 and a gap penalty of 4.

The nucleic acid and protein sequences of the present invention can further be used as a "query sequence" to perform a search against sequence databases to, for example, identify other family members or related sequences. Such searches can be performed using the NBLAST and XBLAST programs (version 2.0) of Altschul, et al. (*J. Mol. Biol.* 215:403–10 (1990)). BLAST nucleotide searches can be performed with the NBLAST program, score=100, wordlength=12 to obtain nucleotide sequences homologous to the nucleic acid molecules of the invention. BLAST protein searches can be performed with the XBLAST program, score=50, wordlength=3 to obtain amino acid sequences homologous to the proteins of the invention. To obtain gapped alignments for comparison purposes, Gapped BLAST can be utilized as described in Altschul et al. (*Nucleic Acids Res.* 25(17):3389–3402 (1997)). When utilizing BLAST and gapped BLAST programs, the default parameters of the respective programs (e.g., XBLAST and NBLAST) can be used.

Full-length pre-processed forms, as well as mature processed forms, of proteins that comprise one of the peptides of the present invention can readily be identified as having complete sequence identity to one of the drug-metabolizing enzyme peptides of the present invention as well as being encoded by the same genetic locus as the drug-metabolizing enzyme peptide provided herein. The gene encoding the novel drug-metabolizing protein of the present invention is located on a genome component that has been mapped to human chromosome 1 (as indicated in FIG. 3), which is supported by multiple lines of evidence, such as STS and BAC map data.

Allelic variants of a drug-metabolizing enzyme peptide can readily be identified as being a human protein having a high degree (significant) of sequence homology/identity to at least a portion of the drug-metabolizing enzyme peptide as well as being encoded by the same genetic locus as the drug-metabolizing enzyme peptide provided herein. Genetic locus can readily be determined based on the genomic information provided in FIG. 3, such as the genomic sequence mapped to the reference human. The gene encoding the novel drug-metabolizing protein of the present invention is located on a genome component that has been mapped to human chromosome 1 (as indicated in FIG. 3), which is supported by multiple lines of evidence, such as STS and BAC map data. As used herein, two proteins (or a region of the proteins) have significant homology when the amino acid sequences are typically at least about 70–80%, 80–90%, and more typically at least about 90–95% or more homologous. A significantly homologous amino acid sequence, according to the present invention, will be encoded by a nucleic acid sequence that will hybridize to a drug-metabolizing enzyme peptide encoding nucleic acid molecule under stringent conditions as more fully described below.

FIG. 3 provides SNP information that has been found in the gene encoding the drug-metabolizing proteins of the present invention. SNPs, including insertion/deletion variants ("indels"), were identified at 45 different nucleotide positions. Changes in the amino acid sequence caused by these SNPs can readily be determined using the universal genetic code and the protein sequence provided in FIG. 2 as a reference. Positioning of each SNP in exons, introns, or outside the ORF can readily be determined using the DNA positions given for each SNP and the start/stop, exon, and intron coordinates given in the features.

Paralogs of a drug-metabolizing enzyme peptide can readily be identified as having some degree of significant sequence homology/identity to at least a portion of the drug-metabolizing enzyme peptide, as being encoded by a gene from humans, and as having similar activity or function. Two proteins will typically be considered paralogs when the amino acid sequences are typically at least about 60% or greater, and more typically at least about 70% or greater homology through a given region or domain. Such paralogs will be encoded by a nucleic acid sequence that will hybridize to a drug-metabolizing enzyme peptide encoding nucleic acid molecule under moderate to stringent conditions as more filly described below.

Orthologs of a drug-metabolizing enzyme peptide can readily be identified as having some degree of significant sequence homology/identity to at least a portion of the drug-metabolizing enzyme peptide as well as being encoded by a gene from another organism. Preferred orthologs will be isolated from mammals, preferably primates, for the development of human therapeutic targets and agents. Such orthologs will be encoded by a nucleic acid sequence that will hybridize to a drug-metabolizing enzyme peptide encoding nucleic acid molecule under moderate to stringent conditions, as more fully described below, depending on the degree of relatedness of the two organisms yielding the proteins.

Non-naturally occurring variants of the drug-metabolizing enzyme peptides of the present invention can readily be generated using recombinant techniques. Such variants include, but are not limited to deletions, additions and substitutions in the amino acid sequence of the drug-metabolizing enzyme peptide. For example, one class of substitutions are conserved amino acid substitution. Such substitutions are those that substitute a given amino acid in a drug-metabolizing enzyme peptide by another amino acid of like characteristics. Typically seen as conservative substitutions are the replacements, one for another, among the aliphatic amino acids Ala, Val, Leu, and Ile; interchange of the hydroxyl residues Ser and Thr; exchange of the acidic residues Asp and Glu; substitution between the amide residues Asn and Gln; exchange of the basic residues Lys and Arg; and replacements among the aromatic residues Phe and Tyr. Guidance concerning which amino acid changes are likely to be phenotypically silent are found in Bowie et al., *Science* 247:1306–1310 (1990).

Variant drug-metabolizing enzyme peptides can be fully functional or can lack function in one or more activities, e.g. ability to bind substrate, ability to phosphorylate substrate, ability to mediate signaling, etc. Fully functional variants typically contain only conservative variation or variation in non-critical residues or in non-critical regions. FIG. 2 provides the result of protein analysis and can be used to identify critical domains/regions. Functional variants can also contain substitution of similar amino acids that result in no change or an insignificant change in function. Alternatively, such substitutions may positively or negatively affect function to some degree.

Non-functional variants typically contain one or more non-conservative amino acid substitutions, deletions, insertions, inversions, or truncation or a substitution, insertion, inversion, or deletion in a critical residue or critical region.

Amino acids that are essential for function can be identified by methods known in the art, such as site-directed mutagenesis or alanine-scanning mutagenesis (Cunningham et al., *Science* 244:1081–1085 (1989)), particularly using the results provided in FIG. 2. The latter procedure introduces single alanine mutations at every residue in the molecule. The resulting mutant molecules are then tested for biological activity such as drug-metabolizing enzyme activity or in assays such as an in vitro proliferative activity. Sites that are critical for binding partner/substrate binding can also be determined by structural analysis such as crystallization, nuclear magnetic resonance or photoaffinity labeling (Smith et al.,*J. Mol. Biol.* 224:899–904 (1992); de Vos et al. *Science* 255:306–312 (1992)).

The present invention further provides fragments of the drug-metabolizing enzyme peptides, in addition to proteins and peptides that comprise and consist of such fragments, particularly those comprising the residues identified in FIG. 2. The fragments to which the invention pertains, however, are not to be construed as encompassing fragments that may be disclosed publicly prior to the present invention.

As used herein, a fragment comprises at least 8, 10, 12, 14, 16, or more contiguous amino acid residues from a drug-metabolizing enzyme peptide. Such fragments can be chosen based on the ability to retain one or more of the biological activities of the drug-metabolizing enzyme peptide or could be chosen for the ability to perform a function, e.g. bind a substrate or act as an immunogen. Particularly important fragments are biologically active fragments, peptides that are, for example, about 8 or more amino acids in length. Such fragments will typically comprise a domain or motif of the drug-metabolizing enzyme peptide, e.g., active site, a transmembrane domain or a substrate-binding domain. Further, possible fragments include, but are not limited to, domain or motif containing fragments, soluble peptide fragments, and fragments containing immunogenic structures. Predicted domains and functional sites are readily identifiable by computer programs well known and readily available to those of skill in the art (e.g., PROSITE analysis). The results of one such analysis are provided in FIG. 2.

Polypeptides often contain amino acids other than the 20 amino acids commonly referred to as the 20 naturally occurring amino acids. Further, many amino acids, including the terminal amino acids, may be modified by natural processes, such as processing and other post-translational modifications, or by chemical modification techniques well known in the art. Common modifications that occur naturally in drug-metabolizing enzyme peptides are described in basic texts, detailed monographs, and the research literature, and they are well known to those of skill in the art (some of these features are identified in FIG. 2).

Known modifications include, but are not limited to, acetylation, acylation, ADP-ribosylation, amidation, covalent attachment of flavin, covalent attachment of a heme moiety, covalent attachment of a nucleotide or nucleotide derivative, covalent attachment of a lipid or lipid derivative, covalent attachment of phosphotidylinositol, cross-linking, cyclization, disulfide bond formation, demethylation, formation of covalent crosslinks, formation of cystine, formation of pyroglutamate, formylation, gamma carboxylation, glycosylation, GPI anchor formation, hydroxylation, iodination, methylation, myristoylation, oxidation, proteolytic processing, phosphorylation, prenylation, racemization, selenoylation, sulfation, transfer-RNA mediated addition of amino acids to proteins such as arginylation, and ubiquitination.

Such modifications are well known to those of skill in the art and have been described in great detail in the scientific literature. Several particularly common modifications, glycosylation, lipid attachment, sulfation, gamma-carboxylation of glutamic acid residues, hydroxylation and ADP-ribosylation, for instance, are described in most basic texts, such as *Proteins—Structure and Molecular Properties,* 2nd Ed., T. E. Creighton, W. H. Freeman and Company, New York (1993). Many detailed reviews are available on this subject, such as by Wold, F., *Posttranslational Covalent Modification of Proteins,* B. C. Johnson, Ed., Academic Press, New York 1–12 (1983); Seifter et al. (*Meth. Enzymol.* 182: 626–646 (1990)) and Rattan et al. (*Ann. N.Y. Acad. Sci.* 663:48–62 (1992)).

Accordingly, the drug-metabolizing enzyme peptides of the present invention also encompass derivatives or analogs in which a substituted amino acid residue is not one encoded by the genetic code, in which a substituent group is included, in which the mature drug-metabolizing enzyme peptide is fused with another compound, such as a compound to increase the half-life of the drug-metabolizing enzyme peptide (for example, polyethylene glycol), or in which the additional amino acids are fused to the mature drug-metabolizing enzyme peptide, such as a leader or secretory sequence or a sequence for purification of the mature drug-metabolizing enzyme peptide or a pro-protein sequence.

Protein/Peptide Uses

The proteins of the present invention can be used in substantial and specific assays related to the functional information provided in the Figures; to raise antibodies or to elicit another immune response; as a reagent (including the labeled reagent) in assays designed to quantitatively determine levels of the protein (or its binding partner or ligand) in biological fluids; and as markers for tissues in which the corresponding protein is preferentially expressed (either constitutively or at a particular stage of tissue differentiation or development or in a disease state). Where the protein binds or potentially binds to another protein or ligand (such as, for example, in a drug-metabolizing enzyme-effector protein interaction or drug-metabolizing enzyme-ligand interaction), the protein can be used to identify the binding partner/ligand so as to develop a system to identify inhibitors of the binding interaction. Any or all of these uses are capable of being developed into reagent grade or kit format for commercialization as commercial products.

Methods for performing the uses listed above are well known to those skilled in the art. References disclosing such methods include "Molecular Cloning: A Laboratory Manual", 2d ed., Cold Spring Harbor Laboratory Press, Sambrook, J., E. F. Fritsch and T. Maniatis eds., 1989, and "Methods in Enzymology: Guide to Molecular Cloning Techniques", Academic Press, Berger, S. L. and A. R. Kimmel eds., 1987.

The potential uses of the peptides of the present invention are based primarily on the source of the protein as well as the class/action of the protein. For example, drug-metabolizing enzymes isolated from humans and their human/mammalian orthologs serve as targets for identifying agents for use in mammalian therapeutic applications, e.g. a human drug, particularly in modulating a biological or pathological response in a cell or tissue that expresses the drug-metabolizing enzyme. Experimental data as provided in FIG. 1 indicates that drug-metabolizing enzyme proteins of the present invention are expressed in humans in the stomach, brain (including infant), endometrial tumors, prostate, kidney, adrenal gland tumors, head/neck, sympathetic trunk, breast, and hepatocellular carcinomas, as indicated by virtual northern blot analysis. PCR-based tissue screening panels also indicate expression in the brain. A large percentage of pharmaceutical agents are being developed that modulate the activity of drug-metabolizing enzyme proteins, particularly members of the omega-hydroxylase cytochrome P450 subfamily (see Background of the Invention). The structural and functional information provided in the Background and Figures provide specific and substantial uses for the molecules of the present invention, particularly in combination with the expression information provided in FIG. 1. Experimental data as provided in FIG. 1 indicates expression in humans in the stomach, brain (including infant), endometrial tumors, prostate, kidney, adrenal gland tumors, head/neck, sympathetic trunk, breast, and hepatocellular carcinomas. Such uses can readily be determined using the information provided herein, that which is known in the art, and routine experimentation.

The drug-metabolizing enzyme polypeptides (including variants and fragments that may have been disclosed prior to the present invention) are useful for biological assays related to drug-metabolizing enzymes that are related to members of the omega-hydroxylase cytochrome P450 subfamily. Such assays involve any of the known drug-metabolizing enzyme functions or activities or properties useful for diagnosis and treatment of drug-metabolizing enzyme-related conditions that are specific for the subfamily of drug-metabolizing enzymes that the one of the present invention belongs to, particularly in cells and tissues that express the drug-metabolizing enzyme. Experimental data as provided in FIG. 1 indicates that drug-metabolizing enzyme proteins of the present invention are expressed in humans in the stomach, brain (including infant), endometrial tumors, prostate, kidney, adrenal gland tumors, head/neck, sympathetic trunk, breast, and hepatocellular carcinomas, as indicated by virtual northern blot analysis. PCR-based tissue screening panels also indicate expression in the brain.

The drug-metabolizing enzyme polypeptides are also useful in drug screening assays, in cell-based or cell-free systems. Cell-based systems can be native, i.e., cells that normally express the drug-metabolizing enzyme, as a biopsy or expanded in cell culture. Experimental data as provided in FIG. 1 indicates expression in humans in the stomach, brain (including infant), endometrial tumors, prostate, kidney, adrenal gland tumors, head/neck, sympathetic trunk, breast, and hepatocellular carcinomas. In an alternate embodiment, cell-based assays involve recombinant host cells expressing the drug-metabolizing enzyme protein.

The polypeptides can be used to identify compounds that modulate drug-metabolizing enzyme activity of the protein in its natural state or an altered form that causes a specific disease or pathology associated with the drug-metabolizing enzyme. Both the drug-metabolizing enzymes of the present invention and appropriate variants and fragments can be used in high-throughput screens to assay candidate compounds for the ability to bind to the drug-metabolizing enzyme. These compounds can be further screened against a functional drug-metabolizing enzyme to determine the effect of the compound on the drug-metabolizing enzyme activity. Further, these compounds can be tested in animal or invertebrate systems to determine activity/effectiveness. Compounds can be identified that activate (agonist) or inactivate (antagonist) the drug-metabolizing enzyme to a desired degree.

Further, the drug-metabolizing enzyme polypeptides can be used to screen a compound for the ability to stimulate or inhibit interaction between the drug-metabolizing enzyme protein and a molecule that normally interacts with the drug-metabolizing enzyme protein. Such assays typically include the steps of combining the drug-metabolizing enzyme protein with a candidate compound under conditions that allow the drug-metabolizing enzyme protein, or fragment, to interact with the target molecule, and to detect the formation of a complex between the protein and the target or to detect the biochemical consequence of the interaction with the drug-metabolizing enzyme protein and the target.

Candidate compounds include, for example, 1) peptides such as soluble peptides, including Ig-tailed fusion peptides and members of random peptide libraries (see, e.g., Lam et al., *Nature* 354:82–84 (1991); Houghten et al., *Nature*

354:84–86 (1991)) and combinatorial chemistry-derived molecular libraries made of D- and/or L-configuration amino acids; 2) phosphopeptides (e.g., members of random and partially degenerate, directed phosphopeptide libraries, see, e.g., Songyang et al., *Cell* 72:767–778 (1993)); 3) antibodies (e.g., polyclonal, monoclonal, humanized, anti-idiotypic, chimeric, and single chain antibodies as well as Fab, F(ab')$_2$, Fab expression library fragments, and epitope-binding fragments of antibodies); and 4) small organic and inorganic molecules (e.g., molecules obtained from combinatorial and natural product libraries).

One candidate compound is a soluble fragment of the receptor that competes for substrate binding. Other candidate compounds include mutant drug-metabolizing enzymes or appropriate fragments containing mutations that affect drug-metabolizing enzyme function and thus compete for substrate. Accordingly, a fragment that competes for substrate, for example with a higher affinity, or a fragment that binds substrate but does not allow release, is encompassed by the invention.

Any of the biological-or biochemical functions mediated by the drug-metabolizing enzyme can be used as an endpoint assay. These include all of the biochemical or biochemical/biological events described herein, in the references cited herein, incorporated by reference for these endpoint assay targets, and other functions known to those of ordinary skill in the art or that can be readily identified using the information provided in the Figures, particularly FIG. 2. Specifically, a biological function of a cell or tissues that expresses the drug-metabolizing enzyme can be assayed. Experimental data as provided in FIG. 1 indicates that drug-metabolizing enzyme proteins of the present invention are expressed in humans in the stomach, brain (including infant), endometrial tumors, prostate, kidney, adrenal gland tumors, head/neck, sympathetic trunk, breast, and hepatocellular carcinomas, as indicated by virtual northern blot analysis. PCR-based tissue screening panels also indicate expression in the brain.

Binding and/or activating compounds can also be screened by using chimeric drug-metabolizing enzyme proteins in which the amino terminal extracellular domain, or parts thereof, the entire transmembrane domain or subregions, such as any of the seven transmembrane segments or any of the intracellular or extracellular loops and the carboxy terminal intracellular domain, or parts thereof, can be replaced by heterologous domains or subregions. For example, a substrate-binding region can be used that interacts with a different substrate then that which is recognized by the native drug-metabolizing enzyme. Accordingly, a different set of signal transduction components is available as an end-point assay for activation. This allows for assays to be performed in other than the specific host cell from which the drug-metabolizing enzyme is derived.

The drug-metabolizing enzyme polypeptides are also useful in competition binding assays in methods designed to discover compounds that interact with the drug-metabolizing enzyme (e.g. binding partners and/or ligands). Thus, a compound is exposed to a drug-metabolizing enzyme polypeptide under conditions that allow the compound to bind or to otherwise interact with the polypeptide. Soluble drug-metabolizing enzyme polypeptide is also added to the mixture. If the test compound interacts with the soluble drug-metabolizing enzyme polypeptide, it decreases the amount of complex formed or activity from the drug-metabolizing enzyme target. This type of assay is particularly useful in cases in which compounds are sought that interact with specific regions of the drug-metabolizing enzyme. Thus, the soluble polypeptide that competes with the target drug-metabolizing enzyme region is designed to contain peptide sequences corresponding to the region of interest.

To perform cell free drug screening assays, it is sometimes desirable to immobilize either the drug-metabolizing enzyme protein, or fragment, or its target molecule to facilitate separation of complexes from uncomplexed forms of one or both of the proteins, as well as to accommodate automation of the assay.

Techniques for immobilizing proteins on matrices can be used in the drug screening assays. In one embodiment, a fusion protein can be provided which adds a domain that allows the protein to be bound to a matrix. For example, glutathione-S-transferase fusion proteins can be adsorbed onto glutathione sepharose beads (Sigma Chemical, St. Louis, Mo.) or glutathione derivatized microtitre plates, which are then combined with the cell lysates (e.g., $^{35}$S-labeled) and the candidate compound, and the mixture incubated under conditions conducive to complex formation (e.g., at physiological conditions for salt and pH). Following incubation, the beads are washed to remove any unbound label, and the matrix immobilized and radiolabel determined directly, or in the supernatant after the complexes are dissociated. Alternatively, the complexes can be dissociated from the matrix, separated by SDS-PAGE, and the level of drug-metabolizing enzyme-binding protein found in the bead fraction quantitated from the gel using standard electrophoretic techniques. For example, either the polypeptide or its target molecule can be immobilized utilizing conjugation of biotin and streptavidin using techniques well known in the art. Alternatively, antibodies reactive with the protein but which do not interfere with binding of the protein to its target molecule can be derivatized to the wells of the plate, and the protein trapped in the wells by antibody conjugation. Preparations of a drug-metabolizing enzyme-binding protein and a candidate compound are incubated in the drug-metabolizing enzyme protein-presenting wells and the amount of complex trapped in the well can be quantitated. Methods for detecting such complexes, in addition to those described above for the GST-immobilized complexes, include immunodetection of complexes using antibodies reactive with the drug-metabolizing enzyme protein target molecule, or which are reactive with drug-metabolizing enzyme protein and compete with the target molecule, as well as enzyme-linked assays which rely on detecting an enzymatic activity associated with the target molecule.

Agents that modulate one of the drug-metabolizing enzymes of the present invention can be identified using one or more of the above assays, alone or in combination. It is generally preferable to use a cell-based or cell free system first and then confirm activity in an animal or other model system. Such model systems are well known in the art and can readily be employed in this context.

Modulators of drug-metabolizing enzyme protein activity identified according to these drug screening assays can be used to treat a subject with a disorder mediated by the drug-metabolizing enzyme pathway, by treating cells or tissues that express the drug-metabolizing enzyme. Experimental data as provided in FIG. 1 indicates expression in humans in the stomach, brain (including infant), endometrial tumors, prostate, kidney, adrenal gland tumors, head/neck, sympathetic trunk, breast, and hepatocellular carcinomas. These methods of treatment include the steps of administering a modulator of drug-metabolizing enzyme activity in a pharmaceutical composition to a subject in need of such treatment, the modulator being identified as described herein.

In yet another aspect of the invention, the drug-metabolizing enzyme proteins can be used as "bait proteins" in a two-hybrid assay or three-hybrid assay (see, e.g., U.S. Pat. No. 5,283,317; Zervos et al. (1993) *Cell* 72:223–232; Madura et al. (1993) *J. Biol. Chem.* 268:12046–12054; Bartel et al. (1993) *Biotechniques* 14:920–924; Iwabuchi et al. (1993) *Oncogene* 8:1693–1696; and Brent WO94/10300), to identify other proteins, which bind to or interact with the drug-metabolizing enzyme and are involved in drug-metabolizing enzyme activity. Such drug-metabolizing enzyme-binding proteins are likely to be drug-metabolizing enzyme inhibitors.

The two-hybrid system is based on the modular nature of most transcription factors, which consist of separable DNA-binding and activation domains. Briefly, the assay utilizes two different DNA constructs. In one construct, the gene that codes for a drug-metabolizing enzyme protein is fused to a gene encoding the DNA binding domain of a known transcription factor (e.g., GAL-4). In the other construct, a DNA sequence, from a library of DNA sequences, that encodes an unidentified protein ("prey" or "sample") is fused to a gene that codes for the activation domain of the known transcription factor. If the "bait" and the "prey" proteins are able to interact, in vivo, forming a drug-metabolizing enzyme-dependent complex, the DNA-binding and activation domains of the transcription factor are brought into close proximity. This proximity allows transcription of a reporter gene (e.g., LacZ) which is operably linked to a transcriptional regulatory site responsive to the transcription factor. Expression of the reporter gene can be detected and cell colonies containing the functional transcription factor can be isolated and used to obtain the cloned gene which encodes the protein which interacts with the drug-metabolizing enzyme protein.

This invention further pertains to novel agents identified by the above-described screening assays. Accordingly, it is within the scope of this invention to further use an agent identified as described herein in an appropriate animal model. For example, an agent identified as described herein (e.g., a drug-metabolizing enzyme-modulating agent, an antisense drug-metabolizing enzyme nucleic acid molecule, a drug-metabolizing enzyme-specific antibody, or a drug-metabolizing enzyme-binding partner) can be used in an animal or other model to determine the efficacy, toxicity, or side effects of treatment with such an agent. Alternatively, an agent identified as described herein can be used in an animal or other model to determine the mechanism of action of such an agent. Furthermore, this invention pertains to uses of novel agents identified by the above-described screening assays for treatments as described herein.

The drug-metabolizing enzyme proteins of the present invention are also useful to provide a target for diagnosing a disease or predisposition to disease mediated by the peptide. Accordingly, the invention provides methods for detecting the presence, or levels of, the protein (or encoding mRNA) in a cell, tissue, or organism. Experimental data as provided in FIG. 1 indicates expression in humans in the stomach, brain (including infant), endometrial tumors, prostate, kidney, adrenal gland tumors, head/neck, sympathetic trunk, breast, and hepatocellular carcinomas. The method involves contacting a biological sample with a compound capable of interacting with the drug-metabolizing enzyme protein such that the interaction can be detected. Such an assay can be provided in a single detection format or a multi-detection format such as an antibody chip array.

One agent for detecting a protein in a sample is an antibody capable of selectively binding to protein. A biological sample includes tissues, cells and biological fluids isolated from a subject, as well as tissues, cells and fluids present within a subject.

The peptides of the present invention also provide targets for diagnosing active protein activity, disease, or predisposition to disease, in a patient having a variant peptide, particularly activities and conditions that are known for other members of the family of proteins to which the present one belongs. Thus, the peptide can be isolated from a biological sample and assayed for the presence of a genetic mutation that results in aberrant peptide. This includes amino acid substitution, deletion, insertion, rearrangement, (as the result of aberrant splicing events), and inappropriate post-translational modification. Analytic methods include altered electrophoretic mobility, altered tryptic peptide digest, altered drug-metabolizing enzyme activity in cell-based or cell-free assay, alteration in substrate or antibody-binding pattern, altered isoelectric point, direct amino acid sequencing, and any other of the known assay techniques useful for detecting mutations in a protein. Such an assay can be provided in a single detection format or a multi-detection format such as an antibody chip array.

In vitro techniques for detection of peptide include enzyme linked immunosorbent assays (ELISAs), Western blots, immunoprecipitations and immunofluorescence using a detection reagent, such as an antibody or protein binding agent. Alternatively, the peptide can be detected in vivo in a subject by introducing into the subject a labeled anti-peptide antibody or other types of detection agent. For example, the antibody can be labeled with a radioactive marker whose presence and location in a subject can be detected by standard imaging techniques. Particularly useful are methods that detect the allelic variant of a peptide expressed in a subject and methods which detect fragments of a peptide in a sample.

The peptides are also useful in pharmacogenomic analysis. Pharmacogenomics deal with clinically significant hereditary variations in the response to drugs due to altered drug disposition and abnormal action in affected persons. See, e.g., Eichelbaum, M. (*Clin. Exp. Pharmacol. Physiol.* 23(10–11):983–985 (1996)), and Linder, M. W. (*Clin. Chem.* 43(2):254–266(1997)). The clinical outcomes of these variations result in severe toxicity of therapeutic drugs in certain individuals or therapeutic failure of drugs in certain individuals as a result of individual variation in metabolism. Thus, the genotype of the individual can determine the way a therapeutic compound acts on the body or the way the body metabolizes the compound. Further, the activity of drug metabolizing enzymes effects both the intensity and duration of drug action. Thus, the pharmacogenomics of the individual permit the selection of effective compounds and effective dosages of such compounds for prophylactic or therapeutic treatment based on the individual's genotype. The discovery of genetic polymorphisms in some drug metabolizing enzymes has explained why some patients do not obtain the expected drug effects, show an exaggerated drug effect, or experience serious toxicity from standard drug dosages. Polymorphisms can be expressed in the phenotype of the extensive metabolizer and the phenotype of the poor metabolizer. Accordingly, genetic polymorphism may lead to allelic protein variants of the drug-metabolizing enzyme protein in which one or more of the drug-metabolizing enzyme functions in one population is different from those in another population. The peptides thus allow a target to ascertain a genetic predisposition that can affect treatment modality. Thus, in a ligand-based treatment, polymorphism may give rise to amino terminal extracellular domains and/or other substrate-binding regions that are more or less active in substrate binding, and drug-metabolizing enzyme activation. Accordingly, substrate dosage would necessarily be modified to maximize the therapeutic effect within a given population containing a polymorphism. As an alternative to genotyping, specific polymorphic peptides could be identified.

The peptides are also useful for treating a disorder characterized by an absence of, inappropriate, or unwanted expression of the protein. Experimental data as provided in FIG. 1 indicates expression in humans in the stomach, brain (including infant), endometrial tumors, prostate, kidney, adrenal gland tumors, head/neck, sympathetic trunk, breast, and hepatocellular carcinomas. Accordingly, methods for treatment include the use of the drug-metabolizing enzyme protein or fragments.

Antibodies

The invention also provides antibodies that selectively bind to one of the peptides of the present invention, a protein comprising such a peptide, as well as variants and fragments thereof. As used herein, an antibody selectively binds a target peptide when it binds the target peptide and does not significantly bind to unrelated proteins. An antibody is still considered to selectively bind a peptide even if it also binds to other proteins that are not substantially homologous with the target peptide so long as such proteins share homology with a fragment or domain of the peptide target of the antibody. In this case, it would be understood that antibody binding to the peptide is still selective despite some degree of cross-reactivity.

As used herein, an antibody is defined in terms consistent with that recognized within the art: they are multi-subunit proteins produced by a mammalian organism in response to an antigen challenge. The antibodies of the present invention include polyclonal antibodies and monoclonal antibodies, as well as fragments of such antibodies, including, but not limited to, Fab or F(ab')$_2$, and Fv fragments.

Many methods are known for generating and/or identifying antibodies to a given target peptide. Several such methods are described by Harlow, Antibodies, Cold Spring Harbor Press, (1989).

In general, to generate antibodies, an isolated peptide is used as an immunogen and is administered to a mammalian organism, such as a rat, rabbit or mouse. The full-length protein, an antigenic peptide fragment or a fusion protein can be used. Particularly important fragments are those covering functional domains, such as the domains identified in FIG. 2, and domain of sequence homology or divergence amongst the family, such as those that can readily be identified using protein alignment methods and as presented in the Figures.

Antibodies are preferably prepared from regions or discrete fragments of the drug-metabolizing enzyme proteins. Antibodies can be prepared from any region of the peptide as described herein. However, preferred regions will include those involved in function/activity and/or drug-metabolizing enzyme/binding partner interaction. FIG. 2 can be used to identify particularly important regions while sequence alignment can be used to identify conserved and unique sequence fragments.

An antigenic fragment will typically comprise at least 8 contiguous amino acid residues. The antigenic peptide can comprise, however, at least 10, 12, 14, 16 or more amino acid residues. Such fragments can be selected on a physical property, such as fragments correspond to regions that are located on the surface of the protein, e.g., hydrophilic regions or can be selected based on sequence uniqueness (see FIG. 2).

Detection on an antibody of the present invention can be facilitated by coupling (i.e., physically linking) the antibody to a detectable substance. Examples of detectable substances include various enzymes, prosthetic groups, fluorescent materials, luminescent materials, bioluminescent materials, and radioactive materials. Examples of suitable enzymes include horseradish peroxidase, alkaline phosphatase, β-galactosidase, or acetylcholinesterase; examples of suitable prosthetic group complexes include streptavidin/biotin and avidin/biotin; examples of suitable fluorescent materials include umbelliferone, fluorescein, fluorescein isothiocyanate, rhodamine, dichlorotriazinylamine fluorescein, dansyl chloride or phycoerythrin; an example of a luminescent material includes luminol; examples of bioluminescent materials include luciferase, luciferin, and aequorin, and examples of suitable radioactive material include $^{125}$I, $^{131}$I, $^{35}$S or $^3$H.

Antibody Uses

The antibodies can be used to isolate one of the proteins of the present invention by standard techniques, such as affinity chromatography or immunoprecipitation. The antibodies can facilitate the purification of the natural protein from cells and recombinantly produced protein expressed in host cells. In addition, such antibodies are useful to detect the presence of one of the proteins of the present invention in cells or tissues to determine the pattern of expression of the protein among various tissues in an organism and over the course of normal development. Experimental data as provided in FIG. 1 indicates that drug-metabolizing enzyme proteins of the present invention are expressed in humans in the stomach, brain (including infant), endometrial tumors, prostate, kidney, adrenal gland tumors, head/neck, sympathetic trunk, breast, and hepatocellular carcinomas, as indicated by virtual northern blot analysis. PCR-based tissue screening panels also indicate expression in the brain. Further, such antibodies can be used to detect protein in situ, in vitro, or in a cell lysate or supernatant in order to evaluate the abundance and pattern of expression. Also, such antibodies can be used to assess abnormal tissue distribution or abnormal expression during development or progression of a biological condition. Antibody detection of circulating fragments of the full length protein can be used to identify turnover.

Further, the antibodies can be used to assess expression in disease states such as in active stages of the disease or in an individual with a predisposition toward disease related to the protein's function. When a disorder is caused by an inappropriate tissue distribution, developmental expression, level of expression of the protein, or expressed/processed form, the antibody can be prepared against the normal protein. Experimental data as provided in FIG. 1 indicates expression in humans in the stomach, brain (including infant), endometrial tumors, prostate, kidney, adrenal gland tumors, head/neck, sympathetic trunk, breast, and hepatocellular carcinomas. If a disorder is characterized by a specific mutation in the protein, antibodies specific for this mutant protein can be used to assay for the presence of the specific mutant protein.

The antibodies can also be used to assess normal and aberrant subcellular localization of cells in the various tissues in an organism. Experimental data as provided in FIG. 1 indicates expression in humans in the stomach, brain (including infant), endometrial tumors, prostate, kidney, adrenal gland tumors, head/neck, sympathetic trunk, breast, and hepatocellular carcinomas. The diagnostic uses can be applied, not only in genetic testing, but also in monitoring a treatment modality. Accordingly, where treatment is ultimately aimed at correcting expression level or the presence of aberrant sequence and aberrant tissue distribution or developmental expression, antibodies directed against the protein or relevant fragments can be used to monitor therapeutic efficacy.

Additionally, antibodies are useful in pharmacogenomic analysis. Thus, antibodies prepared against polymorphic proteins can be used to identify individuals that require modified treatment modalities. The antibodies are also useful as diagnostic tools as an immunological marker for aberrant protein analyzed by electrophoretic mobility, isoelectric point, tryptic peptide digest, and other physical assays known to those in the art.

The antibodies are also useful for tissue typing. Experimental data as provided in FIG. 1 indicates expression in humans in the stomach, brain (including infant), endometrial tumors, prostate, kidney, adrenal gland tumors, head/neck, sympathetic trunk, breast, and hepatocellular carcinomas. Thus, where a specific protein has been correlated with expression in a specific tissue, antibodies that are specific for this protein can be used to identify a tissue type.

The antibodies are also useful for inhibiting protein function, for example, blocking the binding of the drug-metabolizing enzyme peptide to a binding partner such as a substrate. These uses can also be applied in a therapeutic context in which treatment involves inhibiting the protein's function. An antibody can be used, for example, to block binding, thus modulating (agonizing or antagonizing) the peptides activity. Antibodies can be prepared against specific fragments containing sites required for function or against intact protein that is associated with a cell or cell membrane. See FIG. 2 for structural information relating to the proteins of the present invention.

The invention also encompasses kits for using antibodies to detect the presence of a protein in a biological sample. The kit can comprise antibodies such as a labeled or labelable antibody and a compound or agent for detecting protein in a biological sample; means for determining the amount of protein in the sample; means for comparing the amount of protein in the sample with a standard; and instructions for use. Such a kit can be supplied to detect a single protein or epitope or can be configured to detect one of a multitude of epitopes, such as in an antibody detection array. Arrays are described in detail below for nucleic acid arrays and similar methods have been developed for antibody arrays.

Nucleic Acid Molecules

The present invention further provides isolated nucleic acid molecules that encode a drug-metabolizing enzyme peptide or protein of the present invention (cDNA, transcript and genomic sequence). Such nucleic acid molecules will consist of, consist essentially of, or comprise a nucleotide sequence that encodes one of the drug-metabolizing enzyme peptides of the present invention, an allelic variant thereof, or an ortholog or paralog thereof.

As used herein, an "isolated" nucleic acid molecule is one that is separated from other nucleic acid present in the natural source of the nucleic acid. Preferably, an "isolated" nucleic acid is free of sequences that naturally flank the nucleic acid (i.e., sequences located at the 5' and 3' ends of the nucleic acid) in the genomic DNA of the organism from which the nucleic acid is derived. However, there can be some flanking nucleotide sequences, for example up to about 5 KB, 4 KB, 3 KB, 2 KB, or 1 KB or less, particularly contiguous peptide encoding sequences and peptide encoding sequences within the same gene but separated by introns in the genomic sequence. The important point is that the nucleic acid is isolated from remote and unimportant flanking sequences such that it can be subjected to the specific manipulations described herein such as recombinant expression, preparation of probes and primers, and other uses specific to the nucleic acid sequences.

Moreover, an "isolated" nucleic acid molecule, such as a transcript/cDNA molecule, can be substantially free of other cellular material, or culture medium when produced by recombinant techniques, or chemical precursors or other chemicals when chemically synthesized. However, the nucleic acid molecule can be fused to other coding or regulatory sequences and still be considered isolated.

For example, recombinant DNA molecules contained in a vector are considered isolated. Further examples of isolated DNA molecules include recombinant DNA molecules maintained in heterologous host cells or purified (partially or substantially) DNA molecules in solution. Isolated RNA molecules include in vivo or in vitro. RNA transcripts of the isolated DNA molecules of the present invention. Isolated nucleic acid molecules according to the present invention further include such molecules produced synthetically.

Accordingly, the present invention provides nucleic acid molecules that consist of the nucleotide sequence shown in FIG. 1 or 3. (SEQ ID NO:1, transcript sequence and SEQ ID NO:3, genomic sequence), or any nucleic acid molecule that encodes the protein provided in FIG. 2, SEQ ID NO:2. A nucleic acid molecule consists of a nucleotide sequence when the nucleotide sequence is the complete nucleotide sequence of the nucleic acid molecule.

The present invention further provides nucleic acid molecules that consist essentially of the nucleotide sequence shown in FIG. 1 or 3 (SEQ ID NO:1, transcript sequence and SEQ ID NO:3, genomic sequence), or any nucleic acid molecule that encodes the protein provided in FIG. 2, SEQ ID NO:2. A nucleic acid molecule consists essentially of a nucleotide sequence when such a nucleotide sequence is present with only a few additional nucleic acid residues in the final nucleic acid molecule.

The present invention further provides nucleic acid molecules that comprise the nucleotide sequences shown in FIG. 1 or 3 (SEQ ID NO:1, transcript sequence and SEQ ID NO:3, genomic sequence), or any nucleic acid molecule that encodes the protein provided in FIG. 2, SEQ ID NO:2. A nucleic acid molecule comprises a nucleotide sequence when the nucleotide sequence is at least part of the final nucleotide sequence of the nucleic acid molecule. In such a fashion, the nucleic acid molecule can be only the nucleotide sequence or have additional nucleic acid residues, such as nucleic acid residues that are naturally associated with it or heterologous nucleotide sequences. Such a nucleic acid molecule can have a few additional nucleotides or can comprises several hundred or more additional nucleotides. A brief description of how various types of these nucleic acid molecules can be readily made/isolated is provided below.

In FIGS. 1 and 3, both coding and non-coding sequences are provided. Because of the source of the present invention, humans genomic sequence (FIG. 3) and cDNA/transcript sequences (FIG. 1), the nucleic acid molecules in the Figures will contain genomic intronic sequences, 5' and 3' non-coding sequences, gene regulatory regions and non-coding intergenic sequences. In general such sequence features are either noted in FIGS. 1 and 3 or can readily be identified using computational tools known in the art. As discussed below, some of the non-coding regions, particularly gene regulatory elements such as promoters, are useful for a variety of purposes, e.g. control of heterologous gene expression, target for identifying gene activity modulating compounds, and are particularly claimed as fragments of the genomic sequence provided herein.

The isolated nucleic acid molecules can encode the mature protein plus additional amino or carboxyl-terminal amino acids, or amino acids interior to the mature peptide (when the mature form has more than one peptide chain, for instance). Such sequences may play a role in processing of a protein from precursor to a mature form, facilitate protein trafficking, prolong or shorten protein half-life or facilitate manipulation of a protein for assay or production, among other things. As generally is the case in situ, the additional amino acids may be processed away from the mature protein by cellular enzymes.

As mentioned above, the isolated nucleic acid molecules include, but are not limited to, the sequence encoding the drug-metabolizing enzyme peptide alone, the sequence encoding the mature peptide and additional coding sequences, such as a leader or secretory sequence (e.g., a pre-pro or pro-protein sequence), the sequence encoding the mature peptide, with or without the additional coding sequences, plus additional non-coding sequences, for example introns and non-coding 5' and 3' sequences such as transcribed but non-translated sequences that play a role in transcription, mRNA processing (including splicing and polyadenylation signals), ribosome binding and stability of mRNA. In addition, the nucleic acid molecule may be fused to a marker sequence encoding, for example, a peptide that facilitates purification.

Isolated nucleic acid molecules can be in the form of RNA, such as mRNA, or in the form DNA, including cDNA and genomic DNA obtained by cloning or produced by chemical synthetic techniques or by a combination thereof. The nucleic acid, especially DNA, can be double-stranded or single-stranded. Single-stranded nucleic acid can be the coding strand (sense strand) or the non-coding strand (anti-sense strand).

The invention further provides nucleic acid molecules that encode fragments of the peptides of the present invention as well as nucleic acid molecules that encode obvious variants of the drug-metabolizing enzyme proteins of the present invention that are described above. Such nucleic acid molecules may be naturally occurring, such as allelic variants (same locus), paralogs (different locus), and orthologs (different organism), or may be constructed by recombinant DNA methods or by chemical synthesis. Such non-naturally occurring variants may be made by mutagenesis techniques, including those applied to nucleic acid molecules, cells, or organisms. Accordingly, as discussed above, the variants can contain nucleotide substitutions, deletions, inversions and insertions. Variation can occur in either or both the coding and non-coding regions. The variations can produce both conservative and non-conservative amino acid substitutions.

The present invention further provides non-coding fragments of the nucleic acid molecules provided in FIGS. 1 and 3. Preferred non-coding fragments include, but are not limited to, promoter sequences, enhancer sequences, gene modulating sequences and gene termination sequences. Such fragments are useful in controlling heterologous gene expression and in developing screens to identify gene-modulating agents. A promoter can readily be identified as being 5' to the ATG start site in the genomic sequence provided in FIG. 3.

A fragment comprises a contiguous nucleotide sequence greater than 12 or more nucleotides. Further, a fragment could at least 30, 40, 50, 100, 250 or 500 nucleotides in length. The length of the fragment will be based on its intended use. For example, the fragment can encode epitope bearing regions of the peptide, or can be useful as DNA probes and primers. Such fragments can be isolated using the known nucleotide sequence to synthesize an oligonucleotide probe. A labeled probe can then be used to screen a cDNA library, genomic DNA library, or mRNA to isolate nucleic acid corresponding to the coding region. Further, primers can be used in PCR-reactions to clone specific regions of gene.

A probe/primer typically comprises substantially a purified oligonucleotide or oligonucleotide pair. The oligonucleotide typically comprises a region of nucleotide sequence that hybridizes under stringent conditions to at least about 12, 20, 25, 40, 50 or more consecutive nucleotides.

Orthologs, homologs, and allelic variants can be identified using methods well known in the art. As described in the Peptide Section, these variants comprise a nucleotide sequence encoding a peptide that is typically 60–70%, 70–80%, 80–90%, and more typically at least about 90–95% or more homologous to the nucleotide sequence shown in the Figure sheets or a fragment of this sequence. Such nucleic acid molecules can readily be identified as being able to hybridize under moderate to stringent conditions, to the nucleotide sequence shown in the Figure sheets or a fragment of the sequence. Allelic variants can readily be determined by genetic locus of the encoding gene. The gene encoding the novel drug-metabolizing protein of the present invention is located on a genome component that has been mapped to human chromosome 1 (as indicated in FIG. 3), which is supported by multiple lines of evidence, such as STS and BAC map data.

FIG. 3 provides SNP information that has been found in the gene encoding the drug-metabolizing proteins of the present invention. SNPs, including insertion/deletion variants ("indels"), were identified at 45 different nucleotide positions. Changes in the amino acid sequence caused by these SNPs can readily be determined using the universal genetic code and the protein sequence provided in FIG. 2 as a reference. Positioning of each SNP in exons, introns, or outside the ORF can readily be determined using the DNA positions given for each SNP and the start/stop, exon, and intron coordinates given in the features.

As used herein, the term "hybridizes under stringent conditions" is intended to describe conditions for hybridization and washing under which nucleotide sequences encoding a peptide at least 60–70% homologous to each other typically remain hybridized to each other. The conditions can be such that sequences at least about 60%, at least about 70%, or at least about 80% or more homologous to each other typically remain hybridized to each other. Such stringent conditions are known to those skilled in the art and can be found in Current Protocols in Molecular Biology, John Wiley & Sons, New York (1989), 6.3.1–6.3.6. One example of stringent hybridization conditions are hybridization in 6×sodium chloride/sodium citrate (SSC) at about 45C, followed by one or more washes in 0.2×SSC, 0.1% SDS at 50–65C. Examples of moderate to low stringency hybridization conditions are well known in the art.

Nucleic Acid Molecule Uses

The nucleic acid molecules of the present invention are useful for probes, primers, chemical intermediates, and in biological assays. The nucleic acid molecules are useful as a hybridization probe for messenger RNA, transcript/cDNA and genomic DNA to isolate full-length cDNA and genomic clones encoding the peptide described in FIG. 2 and to isolate cDNA and genomic clones that correspond to variants (alleles, orthologs, etc.) producing the same or related peptides shown in FIG. 2. As illustrated in FIG. 3, SNPs were identified at 45 different nucleotide positions.

The probe can correspond to any sequence along the entire length of the nucleic acid molecules provided in the Figures. Accordingly, it could be derived from 5' noncoding regions, the coding region, and 3' noncoding regions. However, as discussed, fragments are not to be construed as encompassing fragments disclosed prior to the present invention.

The nucleic acid molecules are also useful as primers for PCR to amplify any given region of a nucleic acid molecule and are useful to synthesize antisense molecules of desired length and sequence.

The nucleic acid molecules are also useful for constructing recombinant vectors. Such vectors include expression vectors that express a portion of, or all of, the peptide sequences. Vectors also include insertion vectors, used to integrate into another nucleic acid molecule sequence, such as into the cellular genome, to alter in situ expression of a gene and/or gene product. For example, an endogenous coding sequence can be replaced via homologous recombination with all or part of the coding region containing one or more specifically introduced mutations.

The nucleic acid molecules are also useful for expressing antigenic portions of the proteins.

The nucleic acid molecules are also useful as probes for determining the chromosomal positions of the nucleic acid molecules by means of in situ hybridization methods. The gene encoding the novel drug-metabolizing protein of the present invention is located on a genome component that has been mapped to human chromosome 1 (as indicated in FIG. 3), which is supported by multiple lines of evidence, such as STS and BAC map data.

The nucleic acid molecules are also useful in making vectors containing the gene regulatory regions of the nucleic acid molecules of the present invention.

The nucleic acid molecules are also useful for designing ribozymes corresponding to all, or a part, of the mRNA produced from the nucleic acid molecules described herein.

The nucleic acid molecules are also useful for making vectors that express part, or all, of the peptides.

The nucleic acid molecules are also useful for constructing host cells expressing a part, or all, of the nucleic acid molecules and peptides.

The nucleic acid molecules are also useful for constructing transgenic animals expressing all, or a part, of the nucleic acid molecules and peptides.

The nucleic acid molecules are also useful as hybridization probes for determining the presence, level, form and distribution of nucleic acid expression. Experimental data as provided in FIG. 1 indicates that drug-metabolizing enzyme proteins of the present invention are expressed in humans in the stomach, brain (including infant), endometrial tumors, prostate, kidney, adrenal gland tumors, head/neck, sympathetic trunk, breast, and hepatocellular carcinomas, as indicated by virtual northern blot analysis. PCR-based tissue screening panels also indicate expression in the brain. Accordingly, the probes can be used to detect the presence of, or to determine levels of, a specific nucleic acid molecule in cells, tissues, and in organisms. The nucleic acid whose level is determined can be DNA or RNA. Accordingly, probes corresponding to the peptides described herein can be used to assess expression and/or gene copy number in a given cell, tissue, or organism. These uses are relevant for diagnosis of disorders involving an increase or decrease in drug-metabolizing enzyme protein expression relative to normal results.

In vitro techniques for detection of mRNA include Northern hybridizations and in situ hybridizations. In vitro techniques for detecting DNA include Southern hybridizations and in situ hybridization.

Probes can be used as a part of a diagnostic test kit for identifying cells or tissues that express a drug-metabolizing enzyme protein, such as by measuring a level of a drug-metabolizing enzyme-encoding nucleic acid in a sample of cells from a subject e.g., mRNA or genomic DNA, or determining if a drug-metabolizing enzyme gene has been mutated. Experimental data as provided in FIG. 1 indicates that drug-metabolizing enzyme proteins of the present invention are expressed in humans in the stomach, brain (including infant), endometrial tumors, prostate, kidney, adrenal gland tumors, head/neck, sympathetic trunk, breast, and hepatocellular carcinomas, as indicated by virtual northern blot analysis. PCR-based tissue screening panels also indicate expression in the brain.

Nucleic acid expression assays are useful for drug screening to identify compounds that modulate drug-metabolizing enzyme nucleic acid expression.

The invention thus provides a method for identifying a compound that can be used to treat a disorder associated with nucleic acid expression of the drug-metabolizing enzyme gene, particularly biological and pathological processes that are mediated by the drug-metabolizing enzyme in cells and tissues that express it. Experimental data as provided in FIG. 1 indicates expression in humans in the stomach, brain (including infant), endometrial tumors, prostate, kidney, adrenal gland tumors, head/neck, sympathetic trunk, breast, and hepatocellular carcinomas. The method typically includes assaying the ability of the compound to modulate the expression of the drug-metabolizing enzyme nucleic acid and thus identifying a compound that can be used to treat a disorder characterized by undesired drug-metabolizing enzyme nucleic acid expression. The assays can be performed in cell-based and cell-free systems. Cell-based assays include cells naturally expressing the drug-metabolizing enzyme nucleic acid or recombinant cells genetically engineered to express specific nucleic acid sequences.

Thus, modulators of drug-metabolizing enzyme gene expression can be identified in a method wherein a cell is contacted with a candidate compound and the expression of mRNA determined. The level of expression of drug-metabolizing enzyme mRNA in the presence of the candidate compound is compared to the level of expression of drug-metabolizing enzyme mRNA in the absence of the candidate compound. The candidate compound can then be identified as a modulator of nucleic acid expression based on this comparison and be used, for example to treat a disorder characterized by aberrant nucleic acid expression. When expression of mRNA is statistically significantly greater in the presence of the candidate compound than in its absence, the candidate compound is identified as a stimulator of nucleic acid expression. When nucleic acid expression is statistically significantly less in the presence of the candidate compound than in its absence, the candidate compound is identified as an inhibitor of nucleic acid expression.

The invention further provides methods of treatment, with the nucleic acid as a target, using a compound identified through drug screening as a gene modulator to modulate drug-metabolizing enzyme nucleic acid expression in cells and tissues that express the drug-metabolizing enzyme. Experimental data as provided in FIG. 1 indicates that drug-metabolizing enzyme proteins of the present invention are expressed in humans in the stomach, brain (including infant), endometrial tumors, prostate, kidney, adrenal gland tumors, head/neck, sympathetic trunk, breast, and hepatocellular carcinomas, as indicated by virtual northern blot analysis. PCR-based tissue screening panels also indicate expression in the brain. Modulation includes both up-regulation (i.e. activation or agonization) or down-regulation (suppression or antagonization) or nucleic acid expression.

Alternatively, a modulator for drug-metabolizing enzyme nucleic acid expression can be a small molecule or drug identified using the screening assays described herein as long as the drug or small molecule inhibits the drug-metabolizing enzyme nucleic acid expression in the cells and tissues that express the protein. Experimental data as provided in FIG. 1 indicates expression in humans in the stomach, brain (including infant), endometrial tumors, prostate, kidney, adrenal gland tumors, head/neck, sympathetic trunk, breast, and hepatocellular carcinomas.

The nucleic acid molecules are also useful for monitoring the effectiveness of modulating compounds on the expression or activity of the drug-metabolizing enzyme gene in clinical trials or in a treatment regimen. Thus, the gene expression pattern can serve as a barometer for the continuing effectiveness of treatment with the compound, particularly with compounds to which a patient can develop resistance. The gene expression pattern can also serve as a marker indicative of a physiological response of the affected cells to the compound. Accordingly, such monitoring would allow either increased administration of the compound or the administration of alternative compounds to which the patient has not become resistant. Similarly, if the level of nucleic acid expression falls below a desirable level, administration of the compound could be commensurately decreased.

The nucleic acid molecules are also useful in diagnostic assays for qualitative changes in drug-metabolizing enzyme nucleic acid expression, and particularly in qualitative changes that lead to pathology. The nucleic acid molecules can be used to detect mutations in drug-metabolizing enzyme genes and gene expression products such as mRNA. The nucleic acid molecules can be used as hybridization probes to detect naturally occurring genetic mutations in the drug-metabolizing enzyme gene and thereby to determine whether a subject with the mutation is at risk for a disorder caused by the mutation. Mutations include deletion, addition, or substitution of one or more nucleotides in the gene, chromosomal rearrangement, such as inversion or transposition, modification of genomic DNA, such as aberrant methylation patterns or changes in gene copy number, such as amplification. Detection of a mutated form of the drug-metabolizing enzyme gene associated with a dysfunction provides a diagnostic tool for an active disease or susceptibility to disease when the disease results from overexpression, underexpression, or altered expression of a drug-metabolizing enzyme protein.

Individuals carrying mutations in the drug-metabolizing enzyme gene can be detected at the nucleic acid level by a variety of techniques. FIG. 3 provides SNP information that has been found in the gene encoding the drug-metabolizing proteins of the present invention. SNPs, including insertion/deletion variants ("indels"), were identified at 45 different nucleotide positions. Changes in the amino acid sequence caused by these SNPs can readily be determined using the universal genetic code and the protein sequence provided in FIG. 2 as a reference. Positioning of each SNP in exons, introns, or outside the ORF can readily be determined using the DNA positions given for each SNP and the start/stop, exon, and intron coordinates given in the features. The gene encoding the novel drug-metabolizing protein of the present invention is located on a genome component that has been mapped to human chromosome 1 (as indicated in FIG. 3), which is supported by multiple lines of evidence, such as STS and BAC map data. Genomic DNA can be analyzed directly or can be amplified by using PCR prior to analysis. RNA or cDNA can be used in the same way. In some uses, detection of the mutation involves the use of a probe/primer in a polymerase chain reaction (PCR) (see, e.g. U.S. Pat. Nos. 4,683,195 and 4,683,202), such as anchor PCR or RACE PCR, or, alternatively, in a ligation chain reaction (LCR) (see, e.g., Landegran et al., *Science* 241:1077–1080 (1988); and Nakazawa et al., *PNAS* 91:360–364 (1994)), the latter of which can be particularly useful for detecting point mutations in the gene (see Abravaya et al., *Nucleic Acids Res.* 23:675–682 (1995)). This method can include the steps of collecting a sample of cells from a patient, isolating nucleic acid (e.g., genomic, mRNA or both) from the cells of the sample, contacting the nucleic acid sample with one or more primers which specifically hybridize to a gene under conditions such that hybridization and amplification of the gene (if present) occurs, and detecting the presence or absence of an amplification product, or detecting the size of the amplification product and comparing the length to a control sample. Deletions and insertions can be detected by a change in size of the amplified product compared to the normal genotype. Point mutations can be identified by hybridizing amplified DNA to normal RNA or antisense DNA sequences.

Alternatively, mutations in a drug-metabolizing enzyme gene can be directly identified, for example, by alterations in restriction enzyme digestion patterns determined by gel electrophoresis.

Further, sequence-specific ribozymes (U.S. Pat. No. 5,498,531) can be used to score for the presence of specific mutations by development or loss of a ribozyme cleavage site. Perfectly matched sequences can be distinguished from mismatched sequences by nuclease cleavage digestion assays or by differences in melting temperature.

Sequence changes at specific locations can also be assessed by nuclease protection assays such as RNase and S1 protection or the chemical cleavage method. Furthermore, sequence differences between a mutant drug-metabolizing enzyme gene and a wild-type gene can be determined by direct DNA sequencing. A variety of automated sequencing procedures can be utilized when performing the diagnostic assays (Naeve, C. W., (1995) *Biotechniques* 19:448), including sequencing by mass spectrometry (see, e.g., PCT International Publication No. WO 94/16101; Cohen et al., *Adv. Chromatogr.* 36:127–162 (1996); and Griffin et al., *Appl. Biochem. Biotechnol.* 38:147–159 (1993)).

Other methods for detecting mutations in the gene include methods in which protection from cleavage agents is used to detect mismatched bases in RNA/RNA or RNA/DNA duplexes (Myers et al., *Science* 230:1242 (1985)); Cotton et al., *PNAS* 85:4397 (1988); Saleeba et al., *Meth. Enzymol.* 217:286–295 (1992)), electrophoretic mobility of mutant and wild type nucleic acid is compared (Orita et al., *PNAS* 86:2766 (1989); Cotton et al., *Mutat. Res.* 285:125–144 (1993); and Hayashi et al., *Genet. Anal. Tech. Appl.* 9:73–79 (1992)), and movement of mutant or wild-type fragments in polyacrylamide gels containing a gradient of denaturant is assayed using denaturing gradient gel electrophoresis (Myers et al., Nature 313:495 (1985)). Examples of other techniques for detecting point mutations include selective oligonucleotide hybridization, selective amplification, and selective primer extension.

The nucleic acid molecules are also useful for testing an individual for a genotype that while not necessarily causing the disease, nevertheless affects the treatment modality. Thus, the nucleic acid molecules can be used to study the relationship between an individual's genotype and the individual's response to a compound used for treatment (pharmacogenomic relationship). Accordingly, the nucleic acid molecules described herein can be used to assess the mutation content of the drug-metabolizing enzyme gene in an individual in order to select an appropriate compound or dosage regimen for treatment. FIG. 3 provides SNP information that has been found in the gene encoding the drug-metabolizing proteins of the present invention. SNPs, including insertion/deletion variants ("indels"), were identified at 45 different nucleotide positions. Changes in the amino acid sequence caused by these SNPs can readily be determined using the universal genetic code and the protein sequence provided in FIG. 2 as a reference. Positioning of each SNP in exons, introns, or outside the ORF can readily be determined using the DNA positions given for each SNP and the start/stop, exon, and intron coordinates given in the features.

Thus nucleic acid molecules displaying genetic variations that affect treatment provide a diagnostic target that can be used to tailor treatment in an individual. Accordingly, the production of recombinant cells and animals containing these polymorphisms allow effective clinical design of treatment compounds and dosage regimens.

The nucleic acid molecules are thus useful as antisense constructs to control drug-metabolizing enzyme gene expression in cells, tissues, and organisms. A DNA antisense nucleic acid molecule is designed to be complementary to a region of the gene involved in transcription, preventing transcription and hence production of drug-metabolizing enzyme protein. An antisense RNA or DNA nucleic acid molecule would hybridize to the mRNA and thus block translation of mRNA into drug-metabolizing enzyme protein.

Alternatively, a class of antisense molecules can be used to inactivate mRNA in order to decrease expression of drug-metabolizing enzyme nucleic acid. Accordingly, these molecules can treat a disorder characterized by abnormal or undesired drug-metabolizing enzyme nucleic acid expression. This technique involves cleavage by means of ribozymes containing nucleotide sequences complementary to one or more regions in the mRNA that attenuate the ability of the mRNA to be translated. Possible regions include coding regions and particularly coding regions corresponding to the catalytic and other functional activities of the drug-metabolizing enzyme protein, such as substrate binding.

The nucleic acid molecules also provide vectors for gene therapy in patients containing cells that are aberrant in drug-metabolizing enzyme gene expression. Thus, recombinant cells, which include the patient's cells that have been engineered ex vivo and returned to the patient, are introduced into an individual where the cells produce the desired drug-metabolizing enzyme protein to treat the individual.

The invention also encompasses kits for detecting the presence of a drug-metabolizing enzyme nucleic acid in a biological sample. Experimental data as provided in FIG. 1 indicates that drug-metabolizing enzyme proteins of the present invention are expressed in humans in the stomach, brain (including infant), endometrial tumors, prostate, kidney, adrenal gland tumors, head/neck, sympathetic trunk, breast, and hepatocellular carcinomas, as indicated by virtual northern blot analysis. PCR-based tissue screening panels also indicate expression in the brain. For example, the kit can comprise reagents such as a labeled or labelable nucleic acid or agent capable of detecting drug-metabolizing enzyme nucleic acid in a biological sample; means for determining the amount of drug-metabolizing enzyme nucleic acid in the sample; and means for comparing the amount of drug-metabolizing enzyme nucleic acid in the sample with a standard. The compound or agent can be packaged in a suitable container. The kit can further comprise instructions for using the kit to detect drug-metabolizing enzyme protein mRNA or DNA.

Nucleic Acid Arrays

The present invention further provides nucleic acid detection kits, such as arrays or microarrays of nucleic acid molecules that are based on the sequence information provided in FIGS. 1 and 3 (SEQ ID NOS:1 and 3).

As used herein "Arrays" or "Microarrays" refers to an array of distinct polynucleotides or oligonucleotides synthesized on a substrate, such as paper, nylon or other type of membrane, filter, chip, glass slide, or any other suitable solid support. In one embodiment, the microarray is prepared and used according to the methods described in U.S. Pat. No. 5,837,832, Chee et al., PCT application WO95/11995 (Chee et al.), Lockhart, D. J. et al. (1996; Nat. Biotech. 14: 1675–1680) and Schena, M. et al. (1996; Proc. Natl. Acad. Sci. 93: 10614–10619), all of which are incorporated herein in their entirety by reference. In other embodiments, such arrays are produced by the methods described by Brown et al., U.S. Pat. No. 5,807,522.

The microarray or detection kit is preferably composed of a large number of unique, single-stranded nucleic acid sequences, usually either synthetic antisense oligonucleotides or fragments of cDNAs, fixed to a solid support. The oligonucleotides are preferably about 6–60 nucleotides in length, more preferably 15–30 nucleotides in length, and most preferably about 20–25 nucleotides in length. For a certain type of microarray or detection kit, it may be preferable to use oligonucleotides that are only 7–20 nucleotides in length. The microarray or detection kit may contain oligonucleotides that cover the known 5', or 3', sequence, sequential oligonucleotides that cover the full length sequence; or unique oligonucleotides selected from particular areas along the length of the sequence. Polynucleotides used in the microarray or detection kit may be oligonucleotides that are specific to a gene or genes of interest.

In order to produce oligonucleotides to a known sequence for a microarray or detection kit, the gene(s) of interest (or an ORF identified from the contigs of the present invention) is typically examined using a computer algorithm which starts at the 5' or at the 3' end of the nucleotide sequence. Typical algorithms will then identify oligomers of defined length that are unique to the gene, have a GC content within a range suitable for hybridization, and lack predicted secondary structure that may interfere with hybridization. In certain situations it may be appropriate to use pairs of oligonucleotides on a microarray or detection kit. The "pairs" will be identical, except for one nucleotide that preferably is located in the center of the sequence. The second oligonucleotide in the pair (mismatched by one)

serves as a control. The number of oligonucleotide pairs may range from two to one million. The oligomers are synthesized at designated areas on a substrate using a light-directed chemical process. The substrate may be paper, nylon or other type of membrane, filter, chip, glass slide or any other suitable solid support.

In another aspect, an oligonucleotide may be synthesized on the surface of the substrate by using a chemical coupling procedure and an ink jet application apparatus, as described in PCT application WO95/251116 (Baldeschweiler et al.) which is incorporated herein in its entirety by reference. In another aspect, a "gridded" array analogous to a dot (or slot) blot may be used to arrange and link cDNA fragments or oligonucleotides to the surface of a substrate using a vacuum system, thermal, UV, mechanical or chemical bonding procedures. An array, such as those described above, may be produced by hand or by using available devices (slot blot or dot blot apparatus), materials (any suitable solid support), and machines (including robotic instruments), and may contain 8, 24, 96, 384, 1536, 6144 or more oligonucleotides, or any other number between two and one million which lends itself to the efficient use of commercially available instrumentation.

In order to conduct sample analysis using a microarray or detection kit, the RNA or DNA from a biological sample is made into hybridization probes. The mRNA is isolated, and cDNA is produced and used as a template to make antisense RNA (aRNA). The aRNA is amplified in the presence of fluorescent nucleotides, and labeled probes are incubated with the microarray or detection kit so that the probe sequences hybridize to complementary oligonucleotides of the microarray or detection kit. Incubation conditions are adjusted so that hybridization occurs with precise complementary matches or with various degrees of less complementarity. After removal of nonhybridized probes, a scanner is used to determine the levels and patterns of fluorescence. The scanned images are examined to determine degree of complementarity and the relative abundance of each oligonucleotide sequence on the microarray or detection kit. The biological samples may be obtained from any bodily fluids (such as blood, urine, saliva, phlegm, gastric juices, etc.), cultured cells, biopsies, or other tissue preparations. A detection system may be used to measure the absence, presence, and amount of hybridization for all of the distinct sequences simultaneously. This data may be used for large-scale correlation studies on the sequences, expression patterns, mutations, variants, or polymorphisms among samples.

Using such arrays, the present invention provides methods to identify the expression of the drug-metabolizing enzyme proteins/peptides of the present invention. In detail, such methods comprise incubating a test sample with one or more nucleic acid molecules and assaying for binding of the nucleic acid molecule with components within the test sample. Such assays will typically involve arrays comprising many genes, at least one of which is a gene of the present invention and or alleles of the drug-metabolizing enzyme gene of the present invention. FIG. 3 provides SNP information that has been found in the gene encoding the drug-metabolizing proteins of the present invention. SNPs, including insertion/deletion variants ("indels"), were identified at 45 different nucleotide positions. Changes in the amino acid sequence caused by these SNPs can readily be determined using the universal genetic code and the protein sequence provided in FIG. 2 as a reference. Positioning of each SNP in exons, introns, or outside the ORF can readily be determined using the DNA positions given for each SNP and the start/stop, exon, and intron coordinates given in the features.

Conditions for incubating a nucleic acid molecule with a test sample vary. Incubation conditions depend on the format employed in the assay, the detection methods employed, and the type and nature of the nucleic acid molecule used in the assay. One skilled in the art will recognize that any one of the commonly available hybridization, amplification or array assay formats can readily be adapted to employ the novel fragments of the Human genome disclosed herein. Examples of such assays can be found in Chard, T, *An Introduction to Radioimmunoassay and Related Techniques*, Elsevier Science Publishers, Amsterdam, The Netherlands (1986); Bullock, G. R. et al., *Techniques in Immunocytochemistry*, Academic Press, Orlando, Fla. Vol. 1 (1982), Vol. 2 (1983), Vol. 3 (1985); Tijssen, P., *Practice and Theory of Enzyme Immunoassays: Laboratory Techniques in Biochemistry and Molecular Biology*, Elsevier Science Publishers, Amsterdam, The Netherlands (1985).

The test samples of the present invention include cells, protein or membrane extracts of cells. The test sample used in the above-described method will vary based on the assay format, nature of the detection method and the tissues, cells or extracts used as the sample to be assayed. Methods for preparing nucleic acid extracts or of cells are well known in the art and can be readily be adapted in order to obtain a sample that is compatible with the system utilized.

In another embodiment of the present invention, kits are provided which contain the necessary reagents to carry out the assays of the present invention.

Specifically, the invention provides a compartmentalized kit to receive, in close confinement, one or more containers which comprises: (a) a first container comprising one of the nucleic acid molecules that can bind to a fragment of the Human genome disclosed herein; and (b) one or more other containers comprising one or more of the following: wash reagents, reagents capable of detecting presence of a bound nucleic acid.

In detail, a compartmentalized kit includes any kit in which reagents are contained in separate containers. Such containers include small glass containers, plastic containers, strips of plastic, glass or paper, or arraying material such as silica. Such containers allows one to efficiently transfer reagents from one compartment to another compartment such that the samples and reagents are not cross-contaminated, and the agents or solutions of each container can be added in a quantitative fashion from one compartment to another. Such containers will include a container which will accept the test sample, a container which contains the nucleic acid probe, containers which contain wash reagents (such as phosphate buffered saline, Tris-buffers, etc.), and containers which contain the reagents used to detect the bound probe. One skilled in the art will readily recognize that the previously unidentified drug-metabolizing enzyme gene of the present invention can be routinely identified using the sequence information disclosed herein can be readily incorporated into one of the established kit formats which are well known in the art, particularly expression arrays.

Vectors/host Cells

The invention also provides vectors containing the nucleic acid molecules described herein. The term "vector" refers to a vehicle, preferably a nucleic acid molecule, which can transport the nucleic acid molecules. When the vector is a nucleic acid molecule, the nucleic acid molecules are covalently linked to the vector nucleic acid. With this aspect of the invention, the vector includes a plasmid, single or double stranded phage, a single or double stranded RNA or DNA viral vector, or artificial chromosome, such as a BAC, PAC, YAC, OR MAC.

A vector can be maintained in the host cell as an extrachromosomal element where it replicates and produces additional copies of the nucleic acid molecules. Alternatively, the vector may integrate into the host cell genome and produce additional copies of the nucleic acid molecules when the host cell replicates.

The invention provides vectors for the maintenance (cloning vectors) or vectors for expression (expression vectors) of the nucleic acid molecules. The vectors can function in prokaryotic or eukaryotic cells or in both (shuttle vectors).

Expression vectors contain cis-acting regulatory regions that are operably linked in the vector to the nucleic acid molecules such that transcription of the nucleic acid molecules is allowed in a host cell. The nucleic acid molecules can be introduced into the host cell with a separate nucleic acid molecule capable of affecting transcription. Thus, the second nucleic acid molecule may provide a trans-acting factor interacting with the cis-regulatory control region to allow transcription of the nucleic acid molecules from the vector. Alternatively, a trans-acting factor may be supplied by the host cell. Finally, a trans-acting factor can be produced from the vector itself. It is understood, however, that in some embodiments, transcription and/or translation of the nucleic acid molecules can occur in a cell-free system.

The regulatory sequence to which the nucleic acid molecules described herein can be operably linked include promoters for directing mRNA transcription. These include, but are not limited to, the left promoter from bacteriophage λ, the lac, TRP, and TAC promoters from *E. coli*, the early and late promoters from SV40, the CMV immediate early promoter, the adenovirus early and late promoters, and retrovirus long-terminal repeats.

In addition to control regions that promote transcription, expression vectors may also include regions that modulate transcription, such as repressor binding sites and enhancers. Examples include the SV40 enhancer, the cytomegalovirus immediate early enhancer, polyoma enhancer, adenovirus enhancers, and retrovirus LTR enhancers.

In addition to containing sites for transcription initiation and control, expression vectors can also contain sequences necessary for transcription termination and, in the transcribed region a ribosome binding site for translation. Other regulatory control elements for expression include initiation and termination codons as well as polyadenylation signals. The person of ordinary skill in the art would be aware of the numerous regulatory sequences that are useful in expression vectors. Such regulatory sequences are described, for example, in Sambrook et al., *Molecular Cloning: A Laboratory Manual*. 2nd. ed., Cold Spring Harbor Laboratory Press, Cold Spring Harbor, N.Y., (1989).

A variety of expression vectors can be used to express a nucleic acid molecule. Such vectors include chromosomal, episomal, and virus-derived vectors, for example vectors derived from bacterial plasmids, from bacteriophage, from yeast episomes, from yeast chromosomal elements, including yeast artificial chromosomes, from viruses such as baculoviruses, papovaviruses such as SV40, Vaccinia viruses, adenoviruses, poxviruses, pseudorabies viruses, and retroviruses. Vectors may also be derived from combinations of these sources such as those derived from plasmid and bacteriophage genetic elements, e.g. cosmids and phagemids. Appropriate cloning and expression vectors for prokaryotic and eukaryotic hosts are described in Sambrook et al., *Molecular Cloning: A Laboratory Manual*. 2nd. ed., Cold Spring Harbor Laboratory Press, Cold Spring Harbor, N.Y., (1989).

The regulatory sequence may provide constitutive expression in one or more host cells (i.e. tissue specific) or may provide for inducible expression in one or more cell types such as by temperature, nutrient additive, or exogenous factor such as a hormone or other ligand. A variety of vectors providing for constitutive and inducible expression in prokaryotic and eukaryotic hosts are well known to those of ordinary skill in the art.

The nucleic acid molecules can be inserted into the vector nucleic acid by well-known methodology. Generally, the DNA sequence that will ultimately be expressed is joined to an expression vector by cleaving the DNA sequence and the expression vector with one or more restriction enzymes and then ligating the fragments together. Procedures for restriction enzyme digestion and ligation are well known to those of ordinary skill in the art.

The vector containing the appropriate nucleic acid molecule can be introduced into an appropriate host cell for propagation or expression using well-known techniques. Bacterial cells include, but are not limited to, *E. coli*, *Streptomyces*, and *Salmonella typhimurium*. Eukaryotic cells include, but are not limited to, yeast, insect cells such as *Drosophila*, animal cells such as COS and CHO cells, and plant cells.

As described herein, it may be desirable to express the peptide as a fusion protein. Accordingly, the invention provides fusion vectors that allow for the production of the peptides. Fusion vectors can increase the expression of a recombinant protein, increase the solubility of the recombinant protein, and aid in the purification of the protein by acting for example as a ligand for affinity purification. A proteolytic cleavage site may be introduced at the junction of the fusion moiety so that the desired peptide can ultimately be separated from the fusion moiety. Proteolytic enzymes include, but are not limited to, factor Xa, thrombin, and enterokinase. Typical fusion expression vectors include pGEX (Smith et al., *Gene* 67:31–40 (1988)), pMAL (New England Biolabs, Beverly, Mass.) and pRIT5. (Pharmacia, Piscataway, N.J.) which fuse glutathione S-transferase (GST), maltose E binding protein, or protein A, respectively, to the target recombinant protein. Examples of suitable inducible non-fusion *E. coli* expression vectors include pTrc (Amann et al., *Gene* 69:301–315 (1988)) and pET 11d (Studier et al., *Gene Expression Technology: Methods in Enzymology* 185:60–89 (1990)).

Recombinant protein expression can be maximized in host bacteria by providing a genetic background wherein the host cell has an impaired capacity to proteolytically cleave the recombinant protein. (Gottesman, S., *Gene Expression Technology: Methods in Enzymology* 185, Academic Press, San Diego, Calif. (1990)119–128). Alternatively, the sequence of the nucleic acid molecule of interest can be altered to provide preferential codon usage for a specific host cell, for example *E. coli*. (Wada et al., *Nucleic Acids Res.* 20:2111–2118 (1992)).

The nucleic acid molecules can also be expressed by expression vectors that are operative in yeast. Examples of vectors for expression in yeast e.g., *S. cerevisiae* include pYepSec1 (Baldari, et al., *EMBO J.* 6:229–234(1987)), pMFa (Kur jan et al., *Cell* 30:933–943(1982)), pJRY88 (Schultz et al., *Gene* 54:113–123 (1987)), and pYES2 (Invitrogen Corporation, San Diego, Calif.).

The nucleic acid molecules can also be expressed in insect cells using, for example, baculovirus expression vectors.

Baculovirus vectors available for expression of proteins in cultured insect cells (e.g., Sf9 cells) include the pAc series (Smith et al., *Mol. Cell Biol.* 3:2156–2165 (1983)) and the pVL series (Lucklow et al., *Virology* 170:31–39 (1989)).

In certain embodiments of the invention, the nucleic acid molecules described herein are expressed in mammalian cells using mammalian expression vectors. Examples of mammalian expression vectors include pCDM8 (Seed, B. *Nature* 329:840(1987)) and pMT2PC (Kaufman et al., *EMBO J.* 6:187–195 (1987)).

The expression vectors listed herein are provided by way of example only of the well-known vectors available to those of ordinary skill in the art that would be useful to express the nucleic acid molecules. The person of ordinary skill in the art would be aware of other vectors suitable for maintenance propagation or expression of the nucleic acid molecules described herein. These are found for example in Sambrook, J., Fritsh, E. F., and Maniatis, T. *Molecular Cloning: A Laboratory Manual.* 2nd, ed., Cold Spring Harbor Laboratory, Cold Spring Harbor Laboratory Press, Cold Spring Harbor, N.Y., 1989.

The invention also encompasses vectors in which the nucleic acid sequences described herein are cloned into the vector in reverse orientation, but operably linked to a regulatory sequence that permits transcription of antisense RNA. Thus, an antisense transcript can be produced to all, or to a portion, of the nucleic acid molecule sequences described herein, including both coding and non-coding regions. Expression of this antisense RNA is subject to each of the parameters described above in relation to expression of the sense RNA (regulatory sequences, constitutive or inducible expression, tissue-specific expression).

The invention also relates to recombinant host cells containing the vectors described herein. Host cells therefore include prokaryotic cells, lower eukaryotic cells such as yeast, other eukaryotic cells such as insect cells, and higher eukaryotic cells such as mammalian cells.

The recombinant host cells are prepared by introducing the vector constructs described herein into the cells by techniques readily available to the person of ordinary skill in the art. These include, but are not limited to, calcium phosphate transfection, DEAE-dextran-mediated transfection, cationic lipid-mediated transfection, electroporation, transduction, infection, lipofection, and other techniques such as those found in Sambrook, et al. (*Molecular Cloning: A Laboratory Manual.* 2nd, ed., Cold Spring Harbor Laboratory, Cold Spring Harbor Laboratory Press, Cold Spring Harbor, N.Y., 1989).

Host cells can contain more than one vector. Thus, different nucleotide sequences can be introduced on different vectors of the same cell. Similarly, the nucleic acid molecules can be introduced either alone or with other nucleic acid molecules that are not related to the nucleic acid molecules such as those providing trans-acting factors for expression vectors. When more than one vector is introduced into a cell, the vectors can be introduced independently, co-introduced or joined to the nucleic acid molecule vector.

In the case of bacteriophage and viral vectors, these can be introduced into cells as packaged or encapsulated virus by standard procedures for infection and transduction. Viral vectors can be replication-competent or replication-defective. In the case in which viral replication is defective, replication will occur in host cells providing functions that complement the defects.

Vectors generally include selectable markers that enable the selection of the subpopulation of cells that contain the recombinant vector constructs. The marker can be contained in the same vector that contains the nucleic acid molecules described herein or may be on a separate vector. Markers include tetracycline or ampicillin-resistance genes for prokaryotic host cells and dihydrofolate reductase or neomycin resistance for eukaryotic host cells. However, any marker that provides selection for a phenotypic trait will be effective.

While the mature proteins can be produced in bacteria, yeast, mammalian cells, and other cells under the control of the appropriate regulatory sequences, cell-free transcription and translation systems can also be used to produce these proteins using RNA derived from the DNA constructs described herein.

Where secretion of the peptide is desired, appropriate secretion signals are incorporated into the vector. The signal sequence can be endogenous to the peptides or heterologous to these peptides.

Where the peptide is not secreted into the medium, the protein can be isolated from the host cell by standard disruption procedures, including freeze thaw, sonication, mechanical disruption, use of lysing agents and the like. The peptide can then be recovered and purified by well-known purification methods including ammonium sulfate precipitation, acid extraction, anion or cationic exchange chromatography, phosphocellulose chromatography, hydrophobic-interaction chromatography, affinity chromatography, hydroxylapatite chromatography, lectin chromatography, or high performance liquid chromatography.

It is also understood that depending upon the host cell in recombinant production of the peptides described herein, the peptides can have various glycosylation patterns, depending upon the cell, or maybe non-glycosylated as when produced in bacteria. In addition, the peptides may include an initial modified methionine in some cases as a result of a host-mediated process.

Uses of Vectors and Host Cells

The recombinant host cells expressing the peptides described herein have a variety of uses. First, the cells are useful for producing a drug-metabolizing enzyme protein or peptide that can be further purified to produce desired amounts of drug-metabolizing enzyme protein or fragments. Thus, host cells containing expression vectors are useful for peptide production.

Host cells are also useful for conducting cell-based assays involving the drug-metabolizing enzyme protein or drug-metabolizing enzyme protein fragments, such as those described above as well as other formats known in the art. Thus, a recombinant host cell expressing a native drug-metabolizing enzyme protein is useful for assaying compounds that stimulate or inhibit drug-metabolizing enzyme protein function.

Host cells are also useful for identifying drug-metabolizing enzyme protein mutants in which these functions are affected. If the mutants naturally occur and give rise to a pathology, host cells containing the mutations are useful to assay compounds that have a desired effect on the mutant drug-metabolizing enzyme protein (for example, stimulating or inhibiting function) which may not be indicated by their effect on the native drug-metabolizing enzyme protein.

Genetically engineered host cells can be further used to produce non-human transgenic animals. A transgenic animal is preferably a mammal, for example a rodent, such as a rat or mouse, in which one or more of the cells of the animal include a transgene. A transgene is exogenous DNA which is integrated into the genome of a cell from which a transgenic animal develops and which remains in the genome of the mature animal in one or more cell types or tissues of the transgenic animal. These animals are useful for studying the function of a drug-metabolizing enzyme protein and identifying and evaluating modulators of drug-metabolizing enzyme protein activity. Other examples of transgenic animals include non-human primates, sheep, dogs, cows, goats, chickens, and amphibians.

A transgenic animal can be produced by introducing nucleic acid into the male pronuclei of a fertilized oocyte, e.g., by microinjection, retroviral infection, and allowing the oocyte to develop in a pseudopregnant female foster animal. Any of the drug-metabolizing enzyme protein nucleotide sequences can be introduced as a transgene into the genome of a non-human animal, such as a mouse.

Any of the regulatory or other sequences useful in expression vectors can form part of the transgenic sequence. This includes intronic sequences and polyadenylation signals, if not already included. A tissue-specific regulatory sequence (s) can be operably linked to the transgene to direct expression of the drug-metabolizing enzyme protein to particular cells.

Methods for generating transgenic animals via embryo manipulation and microinjection, particularly animals such as mice, have become conventional in the art and are described, for example, in U.S. Pat. Nos. 4,736,866 and 4,870,009, both by Leder et al., U.S. Pat. No. 4,873,191 by Wagner et al. and in Hogan, B., *Manipulating the Mouse Embryo,* (Cold Spring Harbor Laboratory Press, Cold Spring Harbor, N.Y., 1986). Similar methods are used for production of other transgenic animals. A transgenic founder animal can be identified based upon the presence of the transgene in its genome and/or expression of transgenic mRNA in tissues or cells of the animals. A transgenic founder animal can then be used to breed additional animals carrying the transgene. Moreover, transgenic animals carrying a transgene can further be bred to other transgenic animals carrying other transgenes. A transgenic animal also includes animals in which the entire animal or tissues in the animal have been produced using the homologously recombinant host cells described herein.

In another embodiment, transgenic non-human animals can be produced which contain selected systems that allow for regulated expression of the transgene. One example of such a system is the cre/loxP recombinase system of bacteriophage P1. For a description of the cre/loxP recombinase system, see, e.g., Lakso et al. *PNAS* 89:6232–6236 (1992). Another example of a recombinase system is the FLP recombinase system of *S. cerevisiae* (O'Gorman et al. *Science* 251:1351–1355 (1991). If a cre/loxP recombinase system is used to regulate expression of the transgene, animals containing transgenes encoding both the Cre recombinase and a selected protein is required. Such animals can be provided through the construction of "double" transgenic animals, e.g., by mating two transgenic animals, one containing a transgene encoding a selected protein and the other containing a transgene encoding a recombinase.

Clones of the non-human transgenic animals described herein can also be produced according to the methods described in Wilmut, I. et al. *Nature* 385:810–813 (1997) and PCT International Publication Nos. WO 97/07668 and WO 97/07669. In brief, a cell, e.g., a somatic cell, from the transgenic animal can be isolated and induced to exit the growth cycle and enter $G_o$ phase. The quiescent cell can then be fused, e.g., through the use of electrical pulses, to an enucleated oocyte from an animal of the same species from which the quiescent cell is isolated. The reconstructed oocyte is then cultured such that it develops to morula or blastocyst and then transferred to pseudopregnant female foster animal. The offspring born of this female foster animal will be a clone of the animal from which the cell, e.g., the somatic cell, is isolated.

Transgenic animals containing recombinant cells that express the peptides described herein are useful to conduct the assays described herein in an in vivo context. Accordingly, the various physiological factors that are present in vivo and that could effect substrate binding, drug-metabolizing enzyme protein activation, and signal transduction, may not be evident from in vitro cell-free or cell-based assays. Accordingly, it is useful to provide non-human transgenic animals to assay in vivo drug-metabolizing enzyme protein function, including substrate interaction, the effect of specific mutant drug-metabolizing enzyme proteins on drug-metabolizing enzyme protein function and substrate interaction, and the effect of chimeric drug-metabolizing enzyme proteins. It is also possible to assess the effect of null mutations, that is mutations that substantially or completely eliminate one or more drug-metabolizing enzyme protein functions.

All publications and patents mentioned in the above specification are herein incorporated by reference. Various modifications and variations of the described method and system of the invention will be apparent to those skilled in the art without departing from the scope and spirit of the invention. Although the invention has been described in connection with specific preferred embodiments, it should be understood that the invention as claimed should not be unduly limited to such specific embodiments. Indeed, various modifications of the above-described modes for carrying out the invention which are obvious to those skilled in the field of molecular biology or related fields are intended to be within the scope of the following claims.

What is claimed is:

1. An isolated polypeptide consisting of SEQ ID NO:2.
2. An isolated polypeptide comprising SEQ ID NO:2.
3. A composition comprising the polypeptide of claim 1 and a carrier.
4. A composition comprising the polypeptide of claim 2 and a carrier.

* * * * *

SEQUENCE LISTING

<160> NUMBER OF SEQ ID NOS: 4

<210> SEQ ID NO 1
<211> LENGTH: 2327
<212> TYPE: DNA
<213> ORGANISM: Human

<400> SEQUENCE: 1
cgcgcctgcc tcctctcccc aggcctgagc tgccctccc actgcctttc cttcttcccg      60

```
cgagtcagaa gcttcgcgag ggcccagaga ggcggtgggg tgggcgaccc tacgccagct      120
ccgggcggga gaaagcccac cctctcccgc gccccaggaa accgccggcg ttcggcgctg      180
cgcagagcca tggaattctc ctggctggag acgcgctggg cgcggccctt ttacctggcg      240
ttcgtgttct gcctggccct ggggctgctg caggccatta agctgtacct gcggaggcag      300
cggctgctgc gggacctgcg ccccttccca gcgccccca cccactggtt ccttgggcac       360
cagaagttta ttcaggatga taacatggag aagcttgagg aaattattga aaataccct      420 cgtgccttcc ctttctggat tgggcccttt caggcatttt tctgtatcta tgacccagac      480
tatgcaaaga cacttctgag cagaacagat cccaagtccc ggtacctgca gaaattctca      540
cctccacttc ttggaaaagg actagcggct ctagacggac ccaagtggtt ccagcatcgt      600
cgcctactaa ctcctggatt ccattttaac atcctgaaag catacattga ggtgatggct      660
cattctgtga aaatgatgct ggataagtgg gagaagattt gcagcactca ggacacaagc      720
gtggaggtct atgagcacat caactcgatg tctctggata taatcatgaa atgcgctttc      780
agcaaggaga ccaactgcca gacaaacagc acccatgatc cttatgcaaa agccatattt      840
gaactcagca aaatcatatt tcaccgcttg tacagtttgt tgtatcacag tgacataatt      900
ttcaaactca gccctcaggg ctaccgcttc cagaagttaa gccgagtgtt gaatcagtac      960
acagatacaa taatccagga agaaagaaa tccctccagg ctgggtaaa gcaggataac      1020 actccgaaga ggaagtacca ggattttctg gatattgtcc tttctgccaa ggatgaaagt      1080
ggtagcagct tctcagatat tgatgtacac tctgaagtga gcacattcct gttggcagga      1140
catgacacct tggcagcaag catctcctgg atcctttact gcctggctct gaaccctgag      1200
catcaagaga gatgccggga ggaggtcagg gcatcctgg gggatgggtc ttctatcact      1260
tgggaccagc tgggtgagat gtcgtacacc acaatgtgca tcaaggagac gtgccgattg      1320
attcctgcag tcccgtccat ttccagagat ctcagcaagc cacttacctt cccagatgga      1380
tgcacattgc ctgcagggat caccgtggtt cttagtattt ggggtcttca ccacaaccct      1440
gctgctgtct ggaaaaaccc aaaggtcttt gacccctga ggttctctca ggagaattct       1500
gatcagagac accctatgc ctacttacca ttctcagctg atcaaggaa ctgcattggg        1560 caggagtttg ccatgattga gttaaaggta accattgcct tgattctgct ccacttcaga      1620
gtgactccag accccaccag gcctcttact ttccccaacc attttatcct caagcccaag      1680
aatgggatgt atttgcacct gaagaaactc tctgaatgtt agatctcagg gtacaatgat      1740
taaacgtact ttgttttcg aagttaaatt tacagctaat gatccaagca gatagaaagg       1800
gatcaatgta tggtgggagg attggaggtt ggtgggatag gggtctctgt gaagagatcc      1860
aaaatcattt ctaggtacac agtgtgtcag ctagatctgt ttctatataa ctttgggaga      1920
ttttcagatc ttttctgtta aactttcact actattaatg ctgtatacac caatagactt      1980
tcatatattt tctgttgttt ttaaaatagt tttcagaatt atgcaagtaa taagtgcatg      2040
tatgctcact gtcaaaaatt cccaacacta gaaaatcatg tagaataaaa attttaaatc      2100
tcacttcact tagccgacat tccatgccct gaccaatcct actgcttttc ctaaaaacag      2160
aataatttgg tgtgcattct ttcagacttt ttcctataca ttttatatgt agaaatgtag      2220
caatgtattt gtatagatgt gatcattcct atattgttat tgatttttt cacttaataa      2280 aaattcacct tattccttaa aaaaaaaaaa aaaaaaaaa aaaaaaa              2327
```

<210> SEQ ID NO 2

-continued

```
<211> LENGTH: 510
<212> TYPE: PRT
<213> ORGANISM: Human

<400> SEQUENCE: 2

Met Glu Phe Ser Trp Leu Glu Thr Arg Trp Ala Arg Pro Phe Tyr Leu
 1               5                  10                  15

Ala Phe Val Phe Cys Leu Ala Leu Gly Leu Leu Gln Ala Ile Lys Leu
            20                  25                  30

Tyr Leu Arg Arg Gln Arg Leu Leu Arg Asp Leu Arg Pro Phe Pro Ala
        35                  40                  45

Pro Pro Thr His Trp Phe Leu Gly His Gln Lys Phe Ile Gln Asp Asp
    50                  55                  60

Asn Met Glu Lys Leu Glu Glu Ile Ile Glu Lys Tyr Pro Arg Ala Phe
65                  70                  75                  80

Pro Phe Trp Ile Gly Pro Phe Gln Ala Phe Phe Cys Ile Tyr Asp Pro
                85                  90                  95

Asp Tyr Ala Lys Thr Leu Leu Ser Arg Thr Asp Pro Lys Ser Arg Tyr
            100                 105                 110

Leu Gln Lys Phe Ser Pro Pro Leu Leu Gly Lys Gly Leu Ala Ala Leu
        115                 120                 125

Asp Gly Pro Lys Trp Phe Gln His Arg Arg Leu Leu Thr Pro Gly Phe
    130                 135                 140

His Phe Asn Ile Leu Lys Ala Tyr Ile Glu Val Met Ala His Ser Val
145                 150                 155                 160

Lys Met Met Leu Asp Lys Trp Glu Lys Ile Cys Ser Thr Gln Asp Thr
                165                 170                 175

Ser Val Glu Val Tyr Glu His Ile Asn Ser Met Ser Leu Asp Ile Ile
            180                 185                 190

Met Lys Cys Ala Phe Ser Lys Glu Thr Asn Cys Gln Thr Asn Ser Thr
        195                 200                 205

His Asp Pro Tyr Ala Lys Ala Ile Phe Glu Leu Ser Lys Ile Ile Phe
    210                 215                 220

His Arg Leu Tyr Ser Leu Leu Tyr His Ser Asp Ile Ile Phe Lys Leu
225                 230                 235                 240

Ser Pro Gln Gly Tyr Arg Phe Gln Lys Leu Ser Arg Val Leu Asn Gln
                245                 250                 255

Tyr Thr Asp Thr Ile Ile Gln Glu Arg Lys Lys Ser Leu Gln Ala Gly
            260                 265                 270

Val Lys Gln Asp Asn Thr Pro Lys Arg Lys Tyr Gln Asp Phe Leu Asp
        275                 280                 285

Ile Val Leu Ser Ala Lys Asp Glu Ser Gly Ser Ser Phe Ser Asp Ile
    290                 295                 300

Asp Val His Ser Glu Val Ser Thr Phe Leu Leu Ala Gly His Asp Thr
305                 310                 315                 320

Leu Ala Ala Ser Ile Ser Trp Ile Leu Tyr Cys Leu Ala Leu Asn Pro
                325                 330                 335

Glu His Gln Glu Arg Cys Arg Glu Val Arg Gly Ile Leu Gly Asp
            340                 345                 350

Gly Ser Ser Ile Thr Trp Asp Gln Leu Gly Glu Met Ser Tyr Thr Thr
        355                 360                 365

Met Cys Ile Lys Glu Thr Cys Arg Leu Ile Pro Ala Val Pro Ser Ile
    370                 375                 380
```

Ser Arg Asp Leu Ser Lys Pro Leu Thr Phe Pro Asp Gly Cys Thr Leu
385                 390                 395                 400

Pro Ala Gly Ile Thr Val Leu Ser Ile Trp Gly Leu His His Asn
                405                 410                 415

Pro Ala Ala Val Trp Lys Asn Pro Lys Val Phe Asp Pro Leu Arg Phe
            420                 425                 430

Ser Gln Glu Asn Ser Asp Gln Arg His Pro Tyr Ala Tyr Leu Pro Phe
            435                 440                 445

Ser Ala Gly Ser Arg Asn Cys Ile Gly Gln Glu Phe Ala Met Ile Glu
450                 455                 460

Leu Lys Val Thr Ile Ala Leu Ile Leu Leu His Phe Arg Val Thr Pro
465                 470                 475                 480

Asp Pro Thr Arg Pro Leu Thr Phe Pro Asn His Phe Ile Leu Lys Pro
            485                 490                 495

Lys Asn Gly Met Tyr Leu His Leu Lys Lys Leu Ser Glu Cys
            500                 505                 510

<210> SEQ ID NO 3
<211> LENGTH: 31208
<212> TYPE: DNA
<213> ORGANISM: Human
<220> FEATURE:
<221> NAME/KEY: misc_feature
<222> LOCATION: (1)...(31208)
<223> OTHER INFORMATION: n = A,T,C or G

<400> SEQUENCE: 3

```
ccagcctctc ttaggctcct aaatatagtg caaaaagttc cagagttcct ttgttaccca      60
tgaaagcaca tggaacggtg ctggacaggg gcaactggcc ctggagcaga ggagtaactg     120
catagaactg tccaagcctc agagggagtc acaccaccag caagaacctg ggtgggagta     180
ggtgagccaa ggggttccca ggctctgacc ctgccaagag aactcattag aaggtcacca     240
accacacata ctattcctcg gtctcatgaa gaacccaggg accggaccag caagatatc      300
acaaagctga gtttcagct ctggggcaga gcatggatct gaggtctttg gccctaccac     360
catgcgatca tatgagggcc atcatacaac catcatgatt tggggagga ataggcata      420
gaggaatcat atgaaaagct gaaatgccat gagttaccca gaagaagctg tgtaagccag     480
aggattctga ccctgtcaa ataacaaca tctagttgaa ggttggagtt aggtaggagg     540
tagggaagtc tgggaaagaa ggagctgaaa cacttgctgt gtgtggctta atggaacatg     600
caagggcca ggacgaactt ggtccagatg aagtcaccac ccctggggc ctgtcttttt     660
tttttttttt tttttttttt tgagacggag tctcactctg tcaccaggct ggagtgcagt     720
ggcgcgatct cggctcactg caatctttgc ctctcgggtt caagcgattc tcctgcctca     780
gcctcctgag tagctgggat tacaggcgcg cgccaccacg cccagctaat tttagtactg     840
ttagtagaga tggggtttca ccatcttggc caggatggtc ttgatccctt gacctcgtga     900
tccgcccgcc tcggcctccc aaattgctgg gattacaggc gtgagccacc gcgcccggcc     960
ccctggagcc tgtcttaatc acttacccgc caaataaaat ctggctccag agagtggagc    1020
gtaggcttaa ggaattgggg gcggaagggc ggggaaggtg ggggagggac agtgataggg    1080
agaacaggga attgtagcag aaattgggtt tattgttcag agctgtcaat gaacacttaa    1140
catatgcctg tcttagccta aatcaatgaa taaatgaatg aataaataaa tgaatgaaat    1200
gtgggcaatg cctataaaga ttgctgggac agggaggtgg ggggagacac cagcttggga    1260
```

```
agtcaggcct gttagatcct agttcaccac ctgatacgtt acaaatacta aaaccatcac   1320
tttcaaatta ttttttactac attttcctgt tatctgtact cgagtttatt tatgtttctg   1380
gcatctagag tcagcccttc atgggcatga gacccaagca gccacacgag gctctgaacc   1440
cagaagagca tatgctcggt ttaatggtct gtcatcttag aattgttaat aaagttttta   1500
tcccgcattt tcattttgca ctgagattca taaattatat agcaggccct gactgtacct   1560
gtatagtgga attactatat gatggtacgc tactgtgcat atcttcccccg ttcagtgttc   1620
agtgccctcg tatcggcagc ttgaactagc tcatggtaca cgctgggaat cagggtggga   1680
atcagttgta aaccatttac cggaacacca ctaggcaggc cacaggataa aggaataatg   1740
atggtacacc tcccccctacc tctaccacct gggaattttg gtagaatgcc agaatggaaa   1800
agaaaatctc ttgcatagcc atttataatt tgtgataagg aagaaaaaca atgacctcag   1860
cttttagcatt attttacaat ataaattcag atcccgtgac tgaaaactgt tggacttaaa   1920
agaggacgct ccaggagcgc aaaagcagtt gggccgaacg aagcgtgcgc gctttggtaa   1980
ccggctagaa atcccgcacg cgcgcctgcc tcctctcccc aggcctgagc tgcccctccc   2040
actgccttttc cttcttcccg cgagtcagaa gcttcgcgag ggcccagaga ggcggtgggg   2100
gtgggcgacc ctacgccagc tccgggcggg agaaagccca ccctctcccg cgccccatga   2160
aaccgccggc gttcggcgct gcgcagagcc atggaattct cctggctgga gacgcgctgg   2220
gcgcggccct tttacctggc gttcgtgttc tgcctggccc tggggctgct gcaggccatt   2280
aagctgtacc tgcggaggca gcggctgctg cgggacctgc gccccttccc agcgcccccc   2340
acccactggt tccttgggca ccagaaggta aatggaaggg aaaaaggnta gaaaaggagg   2400
aagagggggg cggaggagga tgcggcagag gagcccagcc ggcagagaga cgcagctttc   2460
ttccatccct ggggaccctc cggcttgcac cggccttttcc agcccggcct gtggctctta   2520
gcatcatttt tccttgctct ggagaattgc tttcccgcag ccccacaggg aaaggtcaca   2580
aaagaggaag ctttgggggc tgggagagag ctatttaaag aacctgaata tggaaaaaga   2640
aagcgagctg taactcaagt ctgtctctca ttgcttcacc aagccttcca catgtgttgc   2700
tttaaaaata gcatgttatt ctaaataact tattagttgc agaaaatatg caaaatctat   2760
cccaatcgtt ggcaccctta gtccatttta acaagagaaa attttctttt cctaagattc   2820
ttgtgaagta aggagcagcc ccagccagcc actcgagaaa tactgattga tggaaatttg   2880
taaagggaga ctgttagctt ttggtctctc ccgttttttta aatccactcc caccccctaat   2940
taaggttttt attcattcaa ccgactctga gtggcaattg tgtgataggt actaagatta   3000
caaagagaag ctaagtccct cccctgcacc acccaagtca ggtgcagact taggccacag   3060
agagaaaatg aaaatttaag gcaatgggtg ctttactaga ggcctagaga caagggaata   3120
tctgtcggag gaaagtatac atctccgcct agagaaggaa ggaaagtctg tgaagggctg   3180
agcagagtct taaaggatgg ttgggtggtg tggggaaggc attccagcag agctactaca   3240
cgatcctttg gtttccccac tttctagtct ttcttatata aagcaaccac tttcaactct   3300
tttatcggtt tcttctggta tttaaatact tatttgtaaa atagtattac catattgcat   3360
ctattaattt aataagttta gacatctgct gtggtttaga tatggtttgt tcgtccccac   3420
caagcctcat gttgaaattt gattcccaat gttggaggtg ggatctgatg ggagatcttt   3480
gggtcattgg gatggatccc tcatgaatgt cttggtgcag ctgtctcctt cataagttct   3540
cactctctta gtccctcttc aaccccccaga actgattgtt gaaagagcc tgccacctcc   3600
tcccctctct cttcctgtct ctcaccatgt ggtctctgca cacaactgct cctgttcact   3660
```

-continued

```
tccactatga gtggaagcag tctgagatcc tccgcagatg cagatgccaa tgccatgctt    3720
cttgtacagc ctgcagaatt gtaacccaaa taatcctctt tgtgaatgac ccagcctcag    3780
gtattccttt acagcaacac aaatgtacta agacaacatc cacctatgaa cttctttatg    3840
acaggcaatc acttacactt catattccac tgtcccagta actatatagt attgtatttt    3900
ttaaatagaa aaacttctat ttgtattatt tttattatgc aaatgttatt tactgctgat    3960
ctaaatggtc ctcttttcatt ttatttcctt ttctcataga acttttttccc caccccacca    4020 gtattgnnnn nnnnnnnnn nnnnnnnnnn nnnnnnnnnn nnnnnnnnnn nnnnnnnnnn    4080
nnnnnnnnnn nnnnnnnnnn nnnnnnnnnn nnnnnnnnnn nnnnnnnnnn nnnnnnnnnn    4140
nnnnnnnnnn nnnnnnnnnn nnnnnnnnnn nnnnnnnnnn nnnnnnnnnn nnnnnnnnnn    4200
nnnnnnnnnn nnnnnnnnnn ntgttatgta tctctactgt ctcatgaata ctatgtcgtc    4260
tgttgtttta attgaattgt tttggcatcc ttgtcaaaaa tcaattgacc ataaatgtca    4320
aggtctattt ctgagtcttc aattctaatc cattgatcta tatgtctatc ctaactcatg    4380
gacacagaga gtagaaggat ggttaccaaa ggctgggaag gatagagggg agctggggga    4440
ggaggtaggg aaggttaatg ggtacaaaaa aaatagaaag aatgaataac acctactatt    4500
tgatagcata gcagggtggc tatagtcaat aataactgta cacttttaaa taaagagtgt    4560
aataggattg tttgcaactc aatggataaa tgcttgaggg gatgggtacc ccattcttca    4620
tgatgtgcct atttcacatt gcatgcctgt atcaaaaaca tctcatttac tccataaata    4680
tatacaccta ctatgtatcc acaagtatta aaaattataa ataaataaat tatatagcta    4740
tccttatgct agtaccacac tgccttactg ttgctttgta gtaagctttg aaatcaggaa    4800
gtatgagtcc cccgcacttt ggtattttcc aagattattt tggctgtttg gaatccttga    4860
tttctataca aattttagac tcagcctatc aatttctaca aggaaaccag ctagggttct    4920
gcttgggatt gcactgaatc tgtagatcag tttggggatt attgccatct taagaatatt    4980
aggtcttctg atccatgaac acagaaagcc tttccgttta gttaggtcat cttaattttt    5040
ttttgttgtt ttttttgtt ttttgagaca gagtcctgct ctgtcgccca ggctggagtg    5100
cagtgacgca atctcggctc actgcaacct ccgcctctcg gattcaagcg attctcctgc    5160
ctcagcctcc caagcagctg ggactacagg cacatgccac cacaccaact aattttttgta    5220 ttttcagtag agacggggtt tcaccatatt ggccaggcta gtctcgaact cctgacctcg    5280
tgatccaccc gcctcaccct cccaaagtgc tgggattaca ggcgtgagcc accactcccg    5340
gctttcttta atttttttta acgatgtttt tgtatttttc aaagtataca tcttgcattt    5400
cttttgttaa atttatttgt tttgttcttt taatttcat ttcagactat ttattgcatt    5460
catagtgttt tagagtccac attccctctt gactgtcact aagttttttt ttttctgttt    5520
ttgagaggtt tctatcagaa ttttgcagat cagagatgac ggacatgtca aactgtctaa    5580
tattaccaac cctcccccatt tatcagatca ggatcctttt ggtgattcac catgcaggga    5640
aatctagtat ctaaggctca aaaggtgata ctgttttaca taggcagtaa cattttattg    5700
ctacataata actacatatt tatggagtac ctgtgatatt ttgatacgtg catacaatgt    5760
gcagtgatca aatcagggtg tttagggtat tcatcacttc taacatttat tatttatttg    5820
tgtttggaac atttcaagtc tcttcaagct cttcagaaat attcaataca ttattgttaa    5880
cagtgctatt gaacactgga acttattcct tctatctaaa gacagtaaca ttttaagtat    5940
agtcataagg ttacagaagg ataaagtgtg tatagggaaa attccctaca agatgagaat    6000
```

| | |
|---|---|
| ttcattcctt actcttagta atacaggtct tcaaacatgc caaggatatt cctcccttgg | 6060 |
| agctttgaac atgcacgtct gtggttatat tgctctccct gcaaattatt cctaaaagag | 6120 |
| gcttgccctg accattcaga ctaaaatagc acctctagta ctctctatct ccaaccctat | 6180 |
| tattattatc ttggcccctta tcactctctg acactatact gtatactctt ttgcttgttc | 6240 |
| gtttattatc caccactaac tacaatataa aatctgtgag aggtaggatc tttgtttgcc | 6300 |
| actataaacc tagtgcatgg tacagttcct ggtgcataat aggtgctcaa taaatccttt | 6360 |
| gttgaatgca taaatatatt aggtgctgag aaaatttatt tattcaaaga tcaatttact | 6420 |
| gcatagaata ggccaggtgg tttgacattt attcaatagc caacatatgg gacctaggat | 6480 |
| gtacatatgc aagtgtgtgt gtgtatgtgt gtgtgcatct gcatgtgtac ttggatgtac | 6540 |
| tgcagagaac atctatgtag ctaagtagta taaagcactt gggctccaga gttaaactgg | 6600 |
| agtttgaatc ctcattagtg gttgccagct gtacacactt gggcagatca tttaacctag | 6660 |
| tctgtagggc tcaatttcct catctctaaa gtagggattg taatcatatc tacttcatag | 6720 |
| ggttcttgat gtaaatatta aataacatag aacatggaaa gcatttagca gcacctagtt | 6780 |
| catagcagtg cttgataaat gttcgctgtt gctatttggg ggcactatgc attttctgaa | 6840 |
| catttctgaa caatgtttac taaatatatg tagtacccgt tttcaagtgt atttagatgc | 6900 |
| ttctctgggg atgaagaaat ataaattaaa tatagtacag tattcacaac agttttctgt | 6960 |
| cctttttgtc tagtcaggag ttacaaaaag tataatgaaa tactttcata tggctggggt | 7020 |
| gtttatgaaa attttttacc taaacaaaca attgtcatat tagtttacaa tattcatgag | 7080 |
| ggcaaaggcc ttgtcttcct tatatttctc tgtatctcta ccacctggta cgtgtgatag | 7140 |
| acaataaata cttgtgtgtt tattgtttgt aaatgaataa atgaaaaaat attcacattg | 7200 |
| ttgaaaacca ctactctgga tagtcagtgg gtgcttatca ctggcttgat tatggcaaca | 7260 |
| ttaacaaaaa agtgcagtat tttagaaact aggtttcaag actctcaacc tttcagtggc | 7320 |
| cttgaactat ccagagaaca ctttatgggt taaaattgct aaatgataac agagaaaaat | 7380 |
| gggagccaga gttgtccacc tctccagagg atgagagcaa acaatcctgc agcagatacc | 7440 |
| gtgtgattgg tcacacgagg aaaaatctgg cagccttaag attactttgc agcgggggac | 7500 |
| tcccaccatc atgctcaagt gtgtagatgg gcacaccaaa acacacacat gcaggtgccc | 7560 |
| tccactttac acaagaagca aatgtaaatg aatcttgttt tcagtgattt agagaaacaa | 7620 |
| tttaagtgag ccattactca tctgcttcta aaagcaaaaa ctccttctct ggtggtagta | 7680 |
| tttgcactct catttgtaaa tgttggaagc tgaaagtttt gtatttgagt ttgctttaag | 7740 |
| attcacacat ctgtgtaaat ggaccttctg ttgttggggg gagaatttgg atttctttta | 7800 |
| tagatagagt tggcaatttt ttagagagaa gcatttactg ctaagtcatg agaaataatc | 7860 |
| actggtgcat aattagagag aggaacagga agaagaaatg gtgagctgga tgtagggtca | 7920 |
| tgccccattt agtaactgtt agtttcccac ataggaaata cttcttttta gcttccagat | 7980 |
| cccactccaa tctgagtgtg tgatgttggc aagtgaggca gagagtgtga ctcggctcac | 8040 |
| cctctattgg gacaagagtt cacagtaaat gtcattcaac agtgacttgg tctgggggta | 8100 |
| caggatatat taatattgag aagataaata cactaacttt gtttagagaa ttatccccca | 8160 |
| agcttagaag tcccaaagaa agcatgttat gtcacttcca gaaagtctc aggctcctct | 8220 |
| gcttgtgtga ccttatcagg tcctgaactc agcttgtgtc tataagaggg gacaggtcca | 8280 |
| gcttggctgg ctaattactt ttactttttt cactgcagtt tattcaggat gataacatgg | 8340 |
| agaagcttga ggaaattatt gaaaaatacc ctcgtgcctt ccctttctgg attgggccct | 8400 |

```
ttcaggcatt tttctgtatc tatgacccag actatgcaaa gacacttctg agcagaacag   8460
gtaagaagag ggggaaagct ctgggaccta ttcctcctag aagtgaaatg cataaaaccc   8520
ataggcaaga ttccaaagca aagattggtt tggggccttt aagagacaca gcagcaagta   8580
tggggaggtg acaggtttcc taccaatact gaaggggatt cccatatcct ccccagtccc   8640
ttgtcttgtt caggtatgca tgggcacgtt gaagtcggta taacttaaag cctagctggc   8700
attaccagac ttgccaggca aggcttccct tggcctctgt gggttttatg acttcagtgt   8760
cagcaacact tcccactcct acccctggtc tcgagcataa gtctcaagag ggtgggaaat   8820
cagcagtaac tctacctctg ctggttcagt atgaaagcct gaatgctaga tcattaattt   8880
acccatcaga cctcttgatn nnnnnnnnn nnnnnnnnnn nnnnnnnnnn nnnnnnnnnn   8940
nnnnnnnnnn nnnnnnnnnn nnnnnnnnnn nnnnnnnnnn nnnnnnnnnn nnnnnnnnnn   9000
nnnnnnnnnn nnnnnnnnnn nnnnnnnnnn nnnnnnnnnn nnnnnnnnnn nnnnnnnnnn   9060
nnnnnnnnnn nnnnnnnnnn nnnnnnnnnn nnnnnnnnnn nnnnnnnnnn nnnnnnnnnn   9120
nnnnnnnnnn nnnnnnnnnn nnnnnnnnnn nnnnnnnnnn nnnnnnnnnn nnnnnnnnnn   9180
nnnnnnnnnn nnnnnnnnnn nnnnnnnnnn nnnnnnnnnn nnnnnnnnnn nnnnnnnnnn   9240
nnnnnnnnnn nnnnnnnnnn nnnnnnnnnn nnnnnnnnnn nnnnnnnnnn nnnnnnnnnn   9300
nnnnnnnnnn nnnnnnnnnn nnnnnnnnnn nnnnnnnnnn nnnnnnnnnn nnnnnnnnnn   9360
nnnnnnnnnn nnnnnnnnnn nnnnnnnnnn nnnnnnnnnn nnnnnnnnnn nnnnnnnnnn   9420
nnnnnnnnnn nnnnnnnnnn nnnnnnnnnn nnnnnnnnnn nnnnnnnnnn nnnnnnnnnn   9480
nnnnnnnnnn nnnnnnnnnn nnnnnnnnnn nnnnnnnnnn nnnnnnnnnn nnnnnnnnnn   9540
nnnnnnnnnn nnnnnnnnnn nnnnnnnnnn nnnnnnnnnn nnnnnnnnnn nnnnnnnnnn   9600
nnnnnnnnnn nnnnnnnnnn nnnnnnnnnn nnnnnnnnnn nnnnnnnnnn nnnnnnnnnn   9660
nnnnnnnnnn nnnnnnnnnn nnnnnnnnnn nnnnnnnnnn nnnnnnnnnn nnnnnnnnnn   9720
nnnnnnnnnn nnnnnnnnnn nnnntctgct tgactctgca gatcccaagt cccagtacct   9780
gcagaaattc tcacctccac ttcttggtat gtatgtgcaa atgagaggta taacccactc   9840
tcattcaaag tcccctttcc atagtagagc atgccaaaga aactgaaatc tgaattcaaa   9900
agcacaaaga gtgcaaggta gagctatact gaacgttatc tagggaaag attgaagggg    9960 agctctaagg tcaacacacc accacttccc agaaagcttc ttcatccgtt tctctcccac   10020
aaagtcttat tctcaaggca gcagatacat gaatctgtcc cctctctctt taaaactaca   10080
gccttggcca ggcacagtga ctcatgcatg taatcccagc actttgggag gccaaggtgg   10140
gaggatcact tgaggtcaag atttcaagac cagctgggcc aacatggtga atcccatct    10200 ctactaaaaa tacaaaaatt agccaggcat ggtagcatgt aggcctgtag tcccactact   10260
tgggaggctg agacatgaga atcgcttgaa cctaggaggt ggaggttgcc gtgagctcag   10320
attgtgccac tgcactccag actaggtgac agagcaaaac tctgtccgca gcccccaaca   10380
acaaaaaaaa aactacccaa actgcagtct caccatccct attcttgttt tctttatcct   10440
tctctcgttt tcttggatgt tttcctttct ttttggagtt cctttatttc cacatgcgag   10500
tcagtaaaat tttgctctag agtttggcaa tattctgtca gcagataaac taagctcttt   10560
aattacataa ttggtattta tgttaaacaa gacatgaatg aaagaaaaga ataggctt    10620 gtattaggaa ccacttaaat ttgaatcttg cccctcctg cattgactag ttaaatatga    10680
tcttggggaa gtcatttaat ctctccctat ctcagtttcc tcatctttga caataaggat   10740
```

```
gagactcaca ttgctgggct gttatgagga ttaaatgaaa tacatatttt tagcactaca   10800
tgtaatggcc accattgtat gagtgacaga tcatgcatca tgagcctgga atgttgtaag   10860
cattcaatga atggtatcaa ttatgtatta ataaactta aagtccttt aaagccaaat    10920
cctaatgacc agtctggcaa tagaagattg tgaagcatta gccttggtaa gtatttccac   10980
atagtatcat tcatagacct gggctcaagg aggaaatatc aggggacaga gtggacactc   11040
ttgtctcttt ccttgtgaat ttatgttcat catatagttt atggattggt ttggagtgga   11100
aaggaattca cttgctctgt tactagtgtg agctagggag taggttggct accttatgta   11160
ttcactttca gttaacctcc acagcaacac agggaaaaag gtatttagta tcatagttca   11220
ttattgagaa aagtaaacct caggaagatt gagtcactta ttcagttact acataggtag   11280
taactggtga tttcaggatt agcgtgctaa tcttataagg ctttgaaatt tattagactt   11340
tgaaactgtt tctcacaata ttaaatacat ccatcccaga ggtaagcttc taaattcacc   11400
ttcatctatt aaattgcatt gcacattaat acgagtacta ctttgatact ccactgttgc   11460
atgactgcct gtgggtcatg gttactccac gctgcctgtg ttcctcatct atccttcatc   11520
tcatctaatt aaatggcata aggttttctg cctttattt ctcaaggaaa aggactagcg    11580
gctctagacg gacccaagtg gttccagcat cgtcgcctac taactcctgg attccatttt   11640
aacatcctga aagcatacat tgaggtgatg gctcattctg tgaaaatgat gctggtaagt   11700
aaaggggggaa agtgctctgt gcattgcgaa atgctcccag caatggacag tattaggtat   11760
gtgtttttgtg ggccatgaaa ataaaaaatc agtttctaaa aatttaacca atgtacacgt   11820
acttattgaa caataggtgt ctgtaaaaaa tttgttatgt tctttgagtg ataatattaa   11880
taaaaagatc tggtcctctg tcttagatat attttgagat tttatggcag caaaccaagt   11940
accaaatggt gatagttaga tagtaagtgc tgtagatgtg tttcatggag ggcgggtctg   12000
tacaaaccta ccccaaagtc tgaggaaact gagaggctga agaaaaaggc tgacagtttc   12060
ttaaaaagaa acattcaata gaggctttca aacaaaaacc atnnnnnnnn nnnnnnnnnn   12120
nnnnnnnnnn nnnnnnnnnn nnnnnnnnnn nnnnnnnnnn nnnnnnnnnn nnnnnnnnnn   12180
nnnnnnnnnn nnnnnnnnnn nnnnnnnnnn nnnnnnnnnn nnnnnnnnnn nnnnnnnnnn   12240
nnnnnnnnnn nnnnnnnnnn nnnnnnnnnn nnnnnnnnnn nnnnnnnnnn nnnnnnnnnn   12300
nnnnnnnnnn nnnnnnnnnn nnnnnnnnnn nnnnnnnnnn nnnnnnnnnn nnnnnnnnnn   12360
nnnnnnnnnn nnnnnnnnnn nnnnnnnnnn nnnnnnnnnn nnnnnnnnnn nnnnnnnnnn   12420
nnnnnnnnnn nnnnnnnnnn nnnnnnnnnn nnnnnnnnnn nnnnnnnnnn nnnnnnnnnn   12480
nnnnnnnnnn nnnnnnnnnn nnnnnnnnnn nnnnnnnnnn nnnnnnnnnn nnnnnnnnnn   12540
nnnnnnnnnn nnnnnnnnnn nnnnnnnnnn nnnnnnnnnn nnnnnnnnnn nnnnnnnnnn   12600
nnnnnnnnnn nnnnnnnnnn nnnnnnnnnn nnnnnnnnnn nnnnnnnnnn nnnnnnnnnn   12660
nnnnnnnnnn nnnnnnnnnn nnnnnnnnnn nnnnnnnnnn nnnnnnnnnn nnnnnnnnnn   12720
nnnnnnnnnn nnnnnnnnnn nnnnnnnnnn nnnnnnnnnn nnnnnnnnnn nnnnnnnnnn   12780
nnnnnnnnnn nnnnnnnnnn nnnnnnnnnn nnnnnnnnnn nnnnnnnnnn nnnnnnnnnn   12840
nnnnnnnnnn nnnnnnnnnn nnnnnnnnnn nnnnnnnnnn nnnnnnnnnn nnnnnnnnnn   12900
nnnnnnnnnn nnnnnnnnnn nnnnnnnnnn nnnnnnnnnn nnnnnnnnnn nnnnnnnnnn   12960
nnnnnnnnnn nnnnnnnnnn nnnnnnnnnn nnnnnnnnnn nnnnnnnnnn nnnnnnnnnn   13020
nnnnnnnnnn nnnnnnnnnn nnnnnnnnnn nnnnnnnnnn nnnnnnnnnn nnnnnnnnnn   13080
nnnnnnnnnn nnnnnnnnnn nnnnnnnnnn nnnnnnnnnn nnnnnnnnnn nnnnnnnnnn   13140
```

```
nnnnnnnnnn nnnnnnnnnn nnnnnnnnnn nnnnnnnnnn nnnnnnnnnn nnnnnnnnnn    13200
nnnnnnnnnn nnnnnnnnnn nnnnnnnnnn nnnnnnnnnn nnnnnnnnnn nnnnnnnnnn    13260
nnnnnnnnnn nnnnnnnnnn nnnnnnnnnn nnnnnnnnnn nnnnnnnnnn nnnnnnnnnn    13320
nnnnnnnnnn nnnnnnnnnn nnnnnnnnnn nnnnnnnnnn nnnnnnnnnn nnnnnnnnnn    13380
nnnnnnnnnn nnnnnnnnnn nnnnnnnnnn nnnnnnnnnn nnnnnnnnnn nnnnnnnnnn    13440
nnnnnnnnnn nnnnnnnnnn nnnnnnnnnn nnnnnnnnnn nnnnnnnnnn nnnnnnnnnn    13500
nnnnnnnnnn nnnnnnnnnn nnnnnnnnnn nnnnnnnnnn nnnnnnnnnn nnnnnnnnnn    13560
nnnnnnnnnn nnnnnnnnnn nnnnnnnnnn nnnnnnnnnn nnnnnnnnnn nnnnnnnnnn    13620
nnnnnnnnnn nnnnnnnnnn nnnnnnnnnn nnnnnnnnnn nnnnnnnnnn nnnnnnnnnn    13680
nnnnnnnnnn nnnnnnnnnn nnnnnnnnnn nnnnnnnnnn nnnnnnnnnn nnnnnnnnnn    13740
nnnnnnnnnn nnnnnnnnnn nnnnnnnnng gtcaggcttt gctggggca gctccctgca    13800 acagctcctc tccacacttg ctctgtttct cacttttgaa tccaaacgtt tttgaaaatg    13860
ttctgagttt attttaaaat gtggctatgg tggttgagag cagtggcagg gtacctagca    13920
agtttggaat tgaagttgga ggaagccctg ggtaaaccc cttgtaatta tgggtcttgt    13980
gtcaatgatt gctttaatgg aactctggtc tgtttgaaag cagagttatg gtaataattg    14040
aaaagccgca gatctttaac tcagccattt accatatatg cagttttctc catgctcctt    14100
ctcactccgc tgggtgtatt tttcccttcc tcgtgccctg tgtaagcaca tggcttattt    14160
actcatgtga tctttggttc ctgctgggtc agggttgtct ccattagatc ataaaaacag    14220
ggccaggcag gagccttcaa atgaaggcaa tttggtcatg gtggtggtga tgatgttggt    14280
cttgacctcc tgtgccagga taagtgggag aagatttgca gcactcagga cacaagcgtg    14340
gaggtctatg agcacatcaa ctcgatgtct ctggatataa tcatgaaatg cgctttcagc    14400
aaggagacca actgccagac aaacaggtca gtggtgggag agcaaaaag atatttcttc    14460 acattttcta agttgtttat taacacatta tcccaacttt ctcttctagc acccatgatc    14520
cttatgcaaa agccatattt gaactcagca aaatcatatt tcaccgcttg tacagtttgt    14580
tgtatcacag tgacataatt ttcaaactca gccctcaggg ctaccgcttc cagaagttaa    14640
gccgagtgtt gaatcagtac acaggtattt gttgggtttg ggttgcccac gtccatacgc    14700
tgccatgatt gtactgtgtc tgtctagagg gataaacctt aatatgacaa gagaaagaat    14760
ctttgttatt aatggagctt ttatatagac actgctccaa agaaatttga cttgagtcct    14820
ttataagact ttgcttcaac catagcagta ttatcagaat ttttatatat atatatatac    14880 actatttta ttatggacaa ttattattaa tacaaatata gtaggcact taagagttcc    14940 agacatacat ggaatatggc ttttgcaca gcgattgcag taataataat gacaagctaa    15000
aaacattcat gcaacatagg aatggagagt ggaacagagt aaacatggac atgcacccga    15060
aagaatattg attcaaaaac agttttagca agcataaaca caaaagttga aatagattaa    15120 gcttttaag caattcaaca ttacttgtca tgaatgccat aatggagaat acttatcaag    15180
cagtgaatta atccttcatc agcttcacca cttactagca gttactagta agttacttac    15240
tgctttgttt cagtgtcatc tataaaatgg agattaaaa agaacctatc tcatacattt    15300
gttgttacga tgagtgggtt aatatatata aagcatttag gacagtgcct ggcactgaat    15360
agatgttaaa tgtaaagtat agttatgtca aatgtctttg cttccaggaa ttttgcaaga    15420
cacaccaaca tatgcacact tacacataca tatatgcata catgcacata gatattataa    15480
```

```
agaggacact cagagaagca ggttataaac aatttaaggc ataaatgggc attataaata    15540
gcagcagttc ccaagtcttt ctgcatcatt gcacacacag aaaatgttaa tgtttttgtg    15600
cttcattgga gtaaacagga atggatttgg gggaagctat acagaacttt gtaaaaaaaa    15660
atctttactt tttaaatatt atacaattat gatgaaaaag caaaatgcaa agtgttaggg    15720
aaaatattaa atgttaaatt tattcaaaac ttaaaacctt ttcaattttt tttttttttt    15780 tttttttgaga tggagtctct atcactcagg ctggagcgca gtggtgtgat ctcagctcac    15840
tacaacctcc acctcccagg ttcaggcaat tctcctacct cagccttctg agtagctggg    15900
attacaggca ctgccaccac acctggctaa ttttttttaaa ttgtttattt ttatttagtc    15960
aaatatatca atattttatt ttattgcatc tggatttta gtaatcacaa aaagccattc    16020
tctattccag ggtttctcaa ccctcagcac taatggcttc ttagattaga taagtccttg    16080
ttgtcaagat gtgtgcattg taggatgttt agctacatcc ctgacatcta cccactcgat    16140
gtagtagagc tctgatagtt atagcaacca taaataactc cagacattat tgaatgttcc    16200
cagggccccc agttgagaac cactgccctg tacccaggtt gtagagaaaa ttatttatgt    16260
tttcttgtag tacttgtata atttcattat tttcatattt aaatcagaga tctaaactcc    16320
atttagaatt tattcctata tatggtgtga ggtattgatc taattttttcc aaatgtttat    16380 ccagttgtcc catcaccatt atttaaaagt ttatcttttc aagtgatttg agataaccat    16440
cacattctaa acggatacat gtactggtat ctgttttgga taagagtata tttggatgtt    16500
ctcgtgtatt ccattgatct atctaccaat gtaccagaat cacactgttt taattaagga    16560
gattttgtgg cttttttcaa cattaataga ccttatttt agaaaagttt taggtttgca    16620
gaaaaattca gcagaaagta cagagagttc tcatattacc catgtaacaa acctgtacat    16680
gtacccctgt atctaaaata aaagttgaaa ttttttaaat agtaaataaa tattacctct    16740
gttccatatt tttgttttgt tttttttctc tcagctcctt caattataaa tatattggca    16800
tttctttgcc tgtcttctat ttcattccat tttatttaat aacttttccg tgaagataaa    16860
atattagact gaggaagaaa agaataattg gtcacttgca tctaaacttg aaatcatctt    16920 aatttattg cccacatact gatggaaact atgtttttta tttgtgttgt ttatctttgg    16980
agctttaatc aaaagtccct ttgatgagaa aataaaccat ctgtgaaaat tagatctatt    17040
taaacgtctg gaaatcaggc aagatttgaa gctattcact aaccatggct tgctttataa    17100
tttatttgac tttgccatca ctttggtaat tggaaactat ttttctaccc agatacaata    17160
atccaggaaa gaaagaaatc cctccaggct ggggtaaagc aggataacac tccgaagagg    17220
aagtaccagg attttctgga tattgtcctt tctgccaagg taaatcttct aaatttctaa    17280
gcctgctcaa gtgaccagtt aattatgtaa gtaggtgggt aagtgggaat gggatgggga    17340
gacaagaata aaaccgattg actaaattta actgtacttt gaattgatga gcagcttcat    17400
gcaatttgag acaaagagag aattctgcaa ctgtgtcgct agaggagggt tagtaaagac    17460
taaacgaacg atttgacaag atttgaggat tgtcatatgg atacatggat tttagggcat    17520
catgaaaaaa tggtcacatg gataaacgta aaaattatga tgataaggtc ctgggaaatc    17580
tgggagtttg aagagaattt ctagggcctg ttgatcgagg gccctttgtg caaggcctgc    17640
ttttcttatc taaccttggt tctcctttat gctttgggca gaatatggtt tataccacat    17700
atttgttgaa ctgaattaaa atttaaaccc ctatttaaag ctctgatttt tcccctcaaa    17760
tcattattgt ggttgtatct ccaaacattt ataaactggc attttatta aaatatttgt    17820 attgtacttt ctaggatgaa agtggtagca gcttctcaga tattgatgta cactctgaag    17880
```

```
tgagcacatt cctgttggca ggacatgaca ccttggcagc aagcatctcc tggatccttt    17940
actgcctggc tctgaaccct gagcatcaag agagatgccg ggaggaggtc aggggcatcc    18000
tgggggatgg gtcttctatc acttggtaag atctgcaccc ctaaattttc ctgctagttt    18060 tcccctgag  atttgcttt attttttgcg ctggtacctt agtgaccta  gtgcctcagg    18120
```

```
tgtctcttca ctatgttgat tgtttccttt gttgtgcaga agcttttag  tttgctgcaa    20280 aaccatttat ctatttttc  ttctgttgac tatacttcca gagttgtatc caaaaaatca    20340
ttgccaagaa taatatcaag aagcttttct ctatgttttt ttctagtagt tttatagttt    20400
caggtcatat gtttaaatct ttaatccatt tttagttgat ttttgtatat ggagtgagat    20460
aaaggtccac ttttattctt ctactagtgc atatccagtt ttctcaacac catttattga    20520
agatactgcc ctttcaccac tgtatgttac tggaacctt  gtagatcagt tgacaataaa    20580
tgtgtgggtg tatttctgga ctctttatcc tgttttatta gtttatatgt ctcttttttt    20640
agaagctcta tgctgttttg gtgactagag ctctgtagtc aatttcagat caggtagtat    20700
gatgcactcc agctttgctc ttttgctca  aaattgcttt ggctatttga gttttttat     20760 tccatacgaa ttttagggct tttttttttt ttcgattact gtgaataatg ccattggaat    20820
tttgatggag attgcattga atctttgggt agtatggata ttttaacagt attaatgctt    20880
ccaattaatg aacacagggt attttgcaat ttgtgttttc ttcaatttct ttcaccagtg    20940
tttttttctt aatttaattg ttttatttcc atagggtttg ggtaacaggt ggtgtttggt    21000
tatgagtaag ttctttagtg gtgatttgtg agattttgat gcacccatca cctaagcagt    21060
atacactgta cccaatttgt agtcttgtat ccctcacctc cctcccacca tttcccccaa    21120
gtccccaaag tccattgtat cattcttatg cctttgcatc ctcatagctt agctcccact    21180
tatgagtgag aacatataat gtttggttct ccatttctga gttacttcat ttagaatatt    21240
ggtctccaat tccatccaga ttgctgcgaa tgcctttatt ttgttccttt tcatggctga    21300
gtagtattcc atagtatata catcccacaa tttctttatc cattcttgat tgatgggcat    21360
ttggactggt tccatgtctt tacaattgcg aattgtgctg ctacaaacat gcaggtgcaa    21420
gtgtcttttt catataatga cttctcttcc tctgggtaga taccctgtag tgggattgct    21480
ggatcaaatg gtagttctac ttttagttct ttaaggaatc tccacactgt tttccatagt    21540
ggttgtacta gtttacattc ccaccaacag tgtagaagtg ttccctgttc actgtatcca    21600
caccatcatc tattattatt tgatttttg  attatggcca ttcttgcagg agtaaggtgg    21660
tattgcactg tggttttgat ttgcatttcc ctgatcatta gtgatgttga gcattttttc    21720
atatatttgt tggccatttg tacatcttct tttgagaatt gtctattcat gtcctttgtc    21780 catttttga  tgggattatt tgtttttttc ttgctaattt gagttccctg tagattctgg    21840
atattagacc tttgtggat  gtgtaggttg tgaagatttt ctcccactct ttgggttgtc    21900
tgtttactct gctgattatt tcttttgctg tgcagaaact tttagttta  attaagtccc    21960 acctatttat cttttcgttg ttgttgtttt ttggggttgt tttgttttgg cttggttttg    22020
catctgcttt tgggttcttg gtcatgaagt ctttgcctaa gccaatatct agaagggttt    22080
ttctgatgtt ctagaatttt tatggttcag gtcttagatt taagtccttg atccatcttg    22140
agttgatttt tgtataaggt gagagatgag gatccagttt catgcttcta catgtggctt    22200
gccaattatc ccagtacaat ttgttgaata gggttaatat ttaaagcttt atatatttag    22260
gtgttcctat tttgggtaca tatttattta caactatcat atcctcctga tggattgacc    22320
cctttctcat tatataatgg tcttcttgtc tctttttaca gttttgtct  taaagcctaa    22380 tttgtctgat aaaagttcag ctaccttgc  tctcttttgg tttctatttg catggaatat    22440 tttttttccaa cccttcgcat tcactctatg tgtgttctta aagatgaaat gagatgctgt    22500 agggcatat  gcttgggtct tgttttattc attcattcag ccaccctttt gattagagaa    22560
tttaattcat ttgtattcaa ggtaattatt gacagacaag gacttactac tgccattttg    22620
```

```
ttaattgttt tcttgatgtt ttatagatct tttgttcctt tcatcctctc ttactctttt    22680
cctttgtgat taggtgcttt tctctagtgg tgtactttga tttttacttt ttatcttttg    22740
ttgctctact ataggttttt gctttgtggt taccatgagg gttacataaa gcatagttat    22800
aaaaggctat tttaaactga taacagctta actttcaaca cttaaaaaaa ctatacactt    22860
ttactctacc aactgccctc cattttatgt ctttgatgtc ataatttacc tagttttgga    22920
gatgtgtccc cttattgtgt atcccttaac aaattattgt agcaacagtc attttaata    22980 gttttggctt ttaactttat actagagata gaattaatta acataccacc actacattat    23040
tagggtattc taaattgact atgtatttac ctttatcagt gagattttg ttttcaattt    23100 tcatgttgtt aattagtatt ctttcatttc aacttggaga attcacatta gcatttttg    23160 taagatgggt ctagtagtgg tgaacaccct caacttttgt ttatctggag atgtctttac    23220
ctctgcttca ttttgaaata taactttgt tccatgattg aaatggacaa aattgttttt    23280
ttaattatgc aaagtgccag ggtaagcaga attactcttt ttttttttt ctgagaccga    23340 gtttcactct tgttgcccag gctggagtgc agtggcgcaa tctctcagct taccgcaacc    23400
tctgcctccc aggttcaagc gattcttctg cctcagcctt cctgagtagc tgggattaca    23460
ggcatgcacc accatgctcg gctaattttg cattttagt agagacgggg tttctccatg    23520
ttggtcaggc tggtcttgaa cacccgacct cagatgatcc gcccacctag gcctcccaaa    23580
gtgctgggat tgcaggtgtg agccactgcg cctggccaga attactctta tttatcctga    23640
gcttgaggaa gaaagaattc aaaattaaaa tttcacatta cctaatggcc aaagcctgca    23700
ttcaaaataa gtaatcagaa aaacatataa aaacacaata agataaacag actaaatata    23760
tgcagtcatt ttatggaacc aatctgacta gattggatgc agactaggta ggatgcaaat    23820
ttaaaaaaaa ctttattctt cttccactta taaactttaa acctgctttg tggagcaagt    23880 tcttttatc tctggggaaa gatcctgagt aagtctcata gagttctcat tcatttaaat    23940
cacaagaaca atcttaggtc agtaattaaa ctatctggcc cagtgtaata ctgaaacttt    24000
caaatactta tccacttgag ctcttctttc catcccagct tggtacttct ttggtcctag    24060
aagccagcag tggtttatca tcgacttatt cttactgact agctccccaa tacccagtag    24120
ctgctgtttc tggcccctcc aggaatggtt ttaggaggaa aggggataag gagtaaaggg    24180
ctggtactat tgtgatcatg ccaaagggct tggtggatat tccatgcttc cctttctctc    24240
aagaggaaac tcccttttctt ggagactctc tcactagaac tttccagagg tgattcaggg    24300
gacaagagaa taattgtcct taggcagact cttttttcaag ctggtcccag agctttccct    24360
cttgccagtt aattggttta aggacacagt tgcacatcct tgccttgcct ctgctgctgt    24420
cctctgcctt tctgtctgtt ctgagttata gcctttcaca tcagtcctgt actccccaaa    24480
ctccaaggag cacaagtcag atcatctaag tgatcctctt gaagcctctt gtttaagatg    24540
ggggaagcac ccttcctttt ccatggcact ctggcattcc aacaacactt taaataattt    24600
tttctctcaa aattcttaag cctctcctct ttaatccttc gccatttta tgtattatta    24660 ctttatatga tgagctaaga gttacaaaac tggttttag aaatctcctt agcaaatgtt    24720
ttactgctag tttagcagct cactttataa taaggatata tgatatattt ctttggttcc    24780
tctgcctctg ggacctcagc tcatcctgag gcagagagtc ccattttaac attctgttac    24840
ataaaccagt ggcaaaatgg ctttaacctg agggtaataa ttaccaggaa caaacagaaa    24900
acagaaaaaa agtaaactgg ttatgatatc tgagtccctt ccctccctca tcctcacagg    24960
```

-continued

```
gaccagctgg gtgagatgtc gtacaccaca atgtgcatca aggagacgtg ccgattgatt      25020
cctgcagtcc cgtccatttc cagagatctc agcaagccac ttaccttccc agatggatgc      25080
acattgcctg caggtcttta cattcttttc ctaagcagtt cttagaggct atgggatcct      25140
ggagaccaca gtgacaaaga ttagtgagtc tcttagcact tggagaagtc aaaagataat      25200
gctaacatgt gacttaggtt ttatcaccta tgaggagctc agaggataat gctttggtca      25260
gacatgaatt tcaatgactt tcccaaaggc acatagccaa ttgcagcaaa gctaagccca      25320
gaatccatgt ctctggaatc ccagcccagg gtctcttcca ttgtgggaca tcatttctaa      25380
gataatcttt gtttggctga gtttgagacc gagctgaaac ttcatggaaa atagcaccag      25440
catctttatc tgaaagacca agggggatct ttggcctcat catcataata tcacccttat      25500
aaatatacaa catttaatag ttaatataga gccttcagac ccattatctc attttcccc       25560
ttggaatcca atgttaacag atgcttatac aatgatttac agttcactga acacttttaa      25620
gtactttcaa tgtggcccaa atccagagg cagccccaat gtgtagatga cattaactga       25680
tgtgagcaga gctagaactt gtgcggagac cctgagtctg gagcctagag ttcttcggaa      25740
caacacaggt ttctgagcag ggcttatagg aagcagaggg gtcatgtgag acatattatc      25800
tgattcaatg ttctattaat tcatgtctta ggaagcaagc caacaggatt gcttctggca      25860
aacacctaca gcctgttact gtaactttgc tgacagaccc agaattaatt tctggaagct      25920
agaattattt ctggaaacca ataaccctc acattctctc cctttgttt tgtactctgt         25980
ttctccccaa accacatgga tatttgccaa aattctccac tttccatatg tgaatagcac      26040
caatggaaat ttgtcatggg atctgcatga cagaatcaca gttctgtgtg tgtgtgtgtg      26100
cgttttcctc tcaagacaga gtcttgctat gtagcccagg ctggagtaca gtggcgtaat      26160
ctcggctcac tgcaacctct gcctcccagg tttaagcagt tctcctgcct cagcctcccg      26220
agtagctggg attacaggtg cacaccacgc ctggcaaatt tttgtatttt tattagagat      26280
ggggtttcac catgttggcc aggctagtct caagctcctg atctcgagac cagccctcct      26340
cagcctccca aagcgctggg actacagcca tgagccactg cacccagcca gttctgtgct      26400
tttataccta aattgtctcc aggagtgctt aatagtccat taataggtat ttaggccagg      26460
cacagtggct gacgcatata atcccaatat tttgtgacac caaggtggga agactgcttg      26520
aagttaggag tctgagacta gcctgggcaa catagggaga ccctgtcttt acaaaaaaaa      26580
aaaagagaga gatagccagg catggtgttg catgcttgta ttcctgccta cttgggggac      26640
tgaggcagga ggatcacttg agctcagaag ttcaaggtta ccgtgagcaa tgttcacgcc      26700
actgctctcc agcctgattg acaggccaga ccctgactct aaacaaaaac aaaaaacaaa      26760
tatttaagta atttccaaac atagcagaaa atataagcat ggtttatcac tttgatatga      26820
caccaacagc tacttaagat agagtcatga attcagtaaa ttgttgtgtg gaaagctaag      26880
gtgccaaccc aagccgcatc ttcttaggtg ctcctcactg gtgtcatcag ctacagcagg      26940
cagagcattg ccaggagcta gctcttccct tcaagaacaa aagtcttgtt taagagcaca      27000
gtagcccaca acttgctctt tctcctgcag tctcttttat ttccctcctt tcttagggat      27060
caccgtggtt cttagtattt ggggtcttca ccacaaccct gctgtctgga aaacccaaa       27120
ggtatgattc tctcttgtac ataaatactt ccaagaacta atgctgtgca agtcactttt      27180
tggtagctaa gcacagaagt ggctatataa ttaagggaaa tgacacaaat taaacaaaaa      27240
taaacataaa agccaaaaga aatgtaaaac tattctatgt tcttgaaaca ctcttgacgt      27300
gtatcagtga tttctttcat gtaagccact aaggtttaag atctattact tgtaacagga      27360
```

```
agctggagta tatgtctctg taataattgg ccacatcatc attttgactt gatttctaag   27420
tggatgcaca tccatttcta agtggatgta tctccatagt gaaaataata ccacttgcca   27480
tagtattttt gtttgcctgg gtatcagaca aatcagctgt gaagctgcaa ggtctgcagg   27540
tctgaaggta cactgcccag tgtagtagcc acgggccaca tacggctact gagcacatga   27600
catgtggcca gttggaattg agttgtgctg taagtttaaa atacgtgctg gattttgaag   27660
acatagtacc ctaaaaaaat gtgaaacatt tcctttttagt aattatttat attgattaca   27720
ggttggaatg gtaattttttg gttaaataaa ctctattaag attaacttca cctttttaaaa   27780 atgtgaccac cagaacattt taaattacac atgtagatca cattatattt ctattgatcg   27840
gtgctaggtg gtaggtgaag aaatgtgttc atgttgtttg ggggatggtg ttggggttgt   27900
cctctcattt caggtctttg acccccttgag gttctctcag gagaattctg atcagagaca   27960
cccctatgcc tacttaccat tctcagctgg atcaaggtga gaacaatttg aagttgctga   28020
aagtacccaa agatgtttac ttgagagtag tttattcctt tcagctcctc agctctatac   28080
attcttccag ggaaccgtag atcttggtgc ctatttgagc cccaaaggat cagttagttt   28140
tacaaaggac aatcgtattc tctgtcacat ccttttttggc catgcctcaa aagcagtccc   28200
acaatgtaag ctactgctca taggctcaat gcagtccacc ttcaaagcaa gagaaataat   28260
ttcatgagta actccaactg ccgccttgtt atagggaagg catcatgttg gagcctccca   28320
gctcaaattc tcacagtgaa caatttaagt ctaaagttca aaagtttcaa tggcatttgg   28380
tggaaaaaat atcactttac tgtgtacttc agacttcttg tactagtatt ttactatagt   28440
cagaagaaac atcattttttt caagtatcac tttctttccc tcttgtcttc aggaactgca   28500
ttgggcagga gtttgccatg attgagttaa aggtaaccat tgccttgatt ctgctccact   28560
tcagagtgac tccagacccc accaggcctc ttactttccc caaccatttt atcctcaagc   28620
ccaagaatgg gatgtatttg cacctgaaga aactctctga atgttagatc tcagggtaca   28680
atgattaaac gtactttgtt tttcgaagtt aaatttacag ctaatgatcc aagcagatag   28740
aaagggatca atgtatggtg ggaggattgg aggttggtgg gataggggtc tctgtgaaga   28800
gatccaaaat catttctagg tacacagtgt gtcagctaga tctgtttcta tataactttg   28860
ggagattttc agatcttttc tgttaaactt tcactactat taatgctgta tacaccaata   28920
gactttcata tattttctgt tgttttttaaa atagtttttca gaattatgca agtaataagt   28980
gcatgtatgc tcactgtcaa aaattcccaa cactagaaaa tcatgtagaa taaaaatttt   29040
aaatctcact tcacttagcc gacattccat gccctgacca atcctactgc ttttcctaaa   29100
aacagaataa tttggtgtgc attctttcag acttttttcct atacatttta tatgtagaaa   29160
tgtagcaatg tatttgtata gatgtgatca ttcctatatt gttattgatt tttttcactt   29220
aataaaaatt caccttattc cttatcattg ctttatggta ttctgtaata tgaatgtact   29280
ataatttatt taactatttt ccttattggg catttaagtt atttctagtt ttaaaaacat   29340
gcttgtcaat ggcaacaaaa gccaaaattg acaaatggga tctaattaaa ctaaagagct   29400
tctgcacagc aaaacaaact accatcacac tgaatgggca gcctacagaa tgggagaaaa   29460
tttttgcaac ctactcatct gacaaaggcc taatatccag aatctacaat gaactcaaac   29520
aaatgtacaa gaaaaaaaca accccatcaa aaagtgggtg aaggatatga acagacactt   29580
ctcaaaagaa gacatttacg cagccaaaag acacatgaaa aaatgcctat cgtcactggc   29640
catcagagaa atgcaaatca aaaccacaat gagataccat ctcacaccag ttagaatggc   29700
```

-continued

```
aatcattaaa aagtcaggaa acaacaggtg ctggagagga tgtggagaaa taggaagact    29760
tttacactgt tggtggcagg agaatcactt gaacccggga gggggaggtt gcagtgagcc    29820
gaggtggcgc cactgcactc cagcctgggc gacagaacga gtactccatc tcaaaaaaaa    29880
aaaaaaagga caccaaactt ctcaatctta atgttgtcat ctatgtggta tcttccataa    29940
tctctctcag acagagtcat cttttgctga tatgatctta cagtattttt tgtttatacc    30000
attataatct cattaattgc agcaacacaa atgacaaaag acaactgatt tctcccttg    30060
gatgacctaa tttgctttca ctcttccatc atcacttata acatgatgat tctcaaattc    30120
atctacctaa aatctatata taaaaaaatc cctcccttga attccagatc cttggagaca    30180
aacacccacg tctaaaacca aatttgttta acactggacc agtcgtcctg tgtgactttc    30240
cattttgtca ctattttgtc agctggtata ccaatatcca cccagttaaa caatatttcc    30300
ttgtttttt ctggtacaaa cccaataaa ttacaaacat caataaaagt aaaattctaa    30360
aataactcac tttctctata tatctccttc ttgctggaaa aatgggttag gttagttctt    30420
taaaagcatg catgataaat tgtactgaat acaatattca ggtctggaca tactaggtat    30480
aattttctgt gtctctgggg tcttacctat ttggggtcaa aataaacaag tttattaagc    30540
ttattaatat tcaatttcat tatcttcttt aacaattatg ttccctggta gtttcattgc    30600
caataattta tttgtcaggt tgccaggtgc ttctaaactt ctgtgtattt tttcatatcc    30660
aatttactt taaatatttt tagaaaagag gtctgttaaa tttcctaata attattatat    30720
tattgttttt tcactgacat tttgtgaatt gaaaacccctt aaaaatatga aatcattttt    30780
tcgaaatatg tgccacagac aattttgtta ataagaaga cagaaacagg gcattatcaa    30840
gagataaata ttcaatatac cttatatttc tgtcacacat ttttatacca actgtgccaa    30900
aaattgtata tcatataaat gataacaagt tcacaaaggc attcctttat cccttaactc    30960
tcaaattaga aactttcata ggtaggaagt aggggaagca tatattccct ttgaaaggtg    31020
caagaaaatg tcattggcat tcaccatggt actcttcaag cttaaaaaaa atggactgca    31080
aaacatttac aaacatagca tatttattgg gtacctttat gtttacataa atattgaaga    31140
tatctcacat acctctttca atcagattat ctcactgaca tttattgacc actttctatg    31200
gggaaaac                                                            31208
```

<210> SEQ ID NO 4
<211> LENGTH: 489
<212> TYPE: PRT
<213> ORGANISM: Human

<400> SEQUENCE: 4

```
Val Ala Ala Leu Leu Gly Leu Leu Leu Leu Leu Lys Ala Ala Gln
 1               5                  10                  15

Leu Tyr Leu His Arg Gln Trp Leu Leu Arg Ala Leu Gln Gln Phe Pro
            20                  25                  30

Cys Pro Pro Phe His Trp Leu Leu Gly His Ser Arg Glu Phe Gln Asn
        35                  40                  45

Asp Gln Glu Leu Glu Arg Ile Gln Lys Trp Val Glu Lys Phe Pro Gly
    50                  55                  60

Ala Cys Pro Trp Trp Leu Ser Gly Asn Lys Ala Arg Leu Leu Val Tyr
65                  70                  75                  80

Asp Pro Asp Tyr Leu Lys Val Ile Leu Gly Arg Ser Asp Pro Lys Ala
                85                  90                  95
```

-continued

```
Pro Arg Asn Tyr Lys Leu Met Thr Pro Trp Ile Gly Tyr Gly Leu Leu
                100                 105                 110
Leu Leu Asp Gly Gln Thr Trp Phe Gln His Arg Arg Met Leu Thr Pro
            115                 120                 125
Ala Phe His Tyr Asp Ile Leu Lys Pro Tyr Val Gly Leu Met Val Asp
        130                 135                 140
Ser Val Gln Ile Met Leu Asp Arg Trp Glu Gln Leu Ile Ser Gln Asp
145                 150                 155                 160
Ser Ser Leu Glu Ile Phe Gln His Val Ser Leu Met Thr Leu Asp Thr
                165                 170                 175
Ile Met Lys Cys Ala Phe Ser Tyr Gln Gly Ser Val Gln Leu Asp Arg
            180                 185                 190
Asn Ser His Ser Tyr Ile Gln Ala Ile Asn Asp Leu Asn Asn Leu Val
        195                 200                 205
Phe Tyr Arg Ala Arg Asn Val Phe His Gln Ser Asp Phe Leu Tyr Arg
    210                 215                 220
Leu Ser Pro Glu Gly Arg Leu Phe His Arg Ala Cys Gln Leu Ala His
225                 230                 235                 240
Glu His Thr Asp Arg Val Ile Gln Gln Arg Lys Ala Gln Leu Gln Gln
                245                 250                 255
Glu Gly Glu Leu Glu Lys Val Arg Arg Lys Arg Arg Leu Asp Phe Leu
            260                 265                 270
Asp Val Leu Leu Phe Ala Lys Met Glu Asn Gly Ser Ser Leu Ser Asp
        275                 280                 285
Gln Asp Leu Arg Ala Glu Val Asp Thr Phe Met Phe Glu Gly His Asp
    290                 295                 300
Thr Thr Ala Ser Gly Val Ser Trp Ile Phe Tyr Ala Leu Ala Thr His
305                 310                 315                 320
Pro Glu His Gln His Arg Cys Arg Glu Glu Ile Gln Gly Leu Leu Gly
                325                 330                 335
Asp Gly Ala Ser Ile Thr Trp Glu His Leu Asp Gln Met Pro Tyr Thr
            340                 345                 350
Thr Met Cys Ile Lys Glu Ala Leu Arg Leu Tyr Pro Pro Val Pro Ser
        355                 360                 365
Val Thr Arg Gln Leu Ser Lys Pro Val Thr Phe Pro Asp Gly Arg Ser
    370                 375                 380
Leu Pro Lys Gly Val Ile Leu Phe Leu Ser Ile Tyr Gly Leu His Tyr
385                 390                 395                 400
Asn Pro Lys Val Trp Gln Asn Pro Glu Val Phe Asp Pro Phe Arg Phe
                405                 410                 415
Ala Pro Asp Ser Ala Tyr His Ser His Ala Phe Leu Pro Phe Ser Gly
            420                 425                 430
Gly Ala Arg Asn Cys Ile Gly Lys Gln Phe Ala Met Arg Glu Leu Lys
        435                 440                 445
Val Ala Val Ala Leu Thr Leu Leu Arg Phe Glu Leu Leu Pro Asp Pro
    450                 455                 460
Thr Arg Val Pro Ile Pro Ile Ala Arg Val Val Leu Lys Ser Lys Asn
465                 470                 475                 480
Gly Ile His Leu Arg Leu Arg Lys Leu
                485
```